(12) United States Patent
Bartels et al.

(10) Patent No.: US 10,730,881 B2
(45) Date of Patent: Aug. 4, 2020

(54) FUSED PYRIMIDINE DERIVATIVES

(71) Applicant: Hoffmann-La Roche Inc., Little Falls, NJ (US)

(72) Inventors: Bjoern Bartels, Basel (CH); Roland Jakob-Roetne, Basel (CH); Anja Limberg, Basel (CH); Werner Neidhart, Basel (CH); Hasane Ratni, Basel (CH); Michael Reutlinger, Basel (CH); Sandra Steiner, Basel (CH)

(73) Assignee: HOFFMANN-LA ROCHE, INC., Little Falls, NJ (US)

( * ) Notice: Subject to any disclaimer, the term of this patent is extended or adjusted under 35 U.S.C. 154(b) by 0 days.

(21) Appl. No.: 16/244,405

(22) Filed: Jan. 10, 2019

(65) Prior Publication Data

US 2019/0177329 A1    Jun. 13, 2019

Related U.S. Application Data

(63) Continuation of application No. PCT/EP2017/067323, filed on Jul. 11, 2017.

(30) Foreign Application Priority Data

Jul. 14, 2016 (EP) ..................... 16179501

(51) Int. Cl.
*A61K 31/519* (2006.01)
*A61P 25/28* (2006.01)
*C07D 471/04* (2006.01)
*C07D 487/04* (2006.01)

(52) U.S. Cl.
CPC .......... *C07D 487/04* (2013.01); *C07D 471/04* (2013.01)

(58) Field of Classification Search
CPC ..... A61K 31/519; A61P 25/28; C07D 471/04; C07D 487/04
See application file for complete search history.

(56) References Cited

FOREIGN PATENT DOCUMENTS

| EP | 2 050 749 A1 | 4/2009 |
|---|---|---|
| WO | 2006/056863 A1 | 6/2006 |
| WO | 2012/116965 A1 | 9/2012 |

OTHER PUBLICATIONS

Bai et al., "An atomic structure of human γ-secretase" Nature 525:212-217 (Sep. 10, 2015).
Beher et al., "Selected Non-steriodal Anti-inflammatory Drugs and Their Derivatives Target γ-Secretase at a Novel Site" Journal of Biological Chemistry 279(42):43419-43426 ( 2004).
Bian et al., "Synthesis of 2-[2H]-2-(1-methylalkyl)succinic acids" Chinese Chemical Letters 26(5):619-622 (May 2015).
Bursavich et al., "Gamma Secretase Modulators: New Alzheimer's Drugs on the Horizon?" Journal of Medicinal Chemistry 59:7389-7409 ( 2016).

(Continued)

*Primary Examiner* — Brenda L Coleman
(74) *Attorney, Agent, or Firm* — Genentech, Inc.; Richard G. A. Bone

(57) ABSTRACT

The present invention relates to a compound of formula I

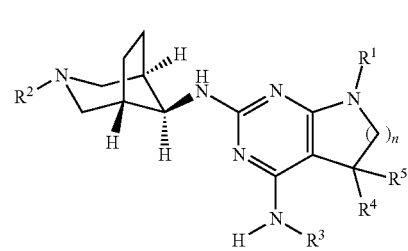

wherein
$R^1$ is phenyl, lower alkyl, $C_{3-6}$-cycloalkyl, —$CH_2$—$C_{3-6}$-cycloalkyl or bridged $C_{4-6}$-cycloalkyl, substituted by one, two or three halogen atoms, or by lower alkyl or lower alkyl substituted by halogen;
$R^2$ is a five or six membered heteroaryl group, selected from

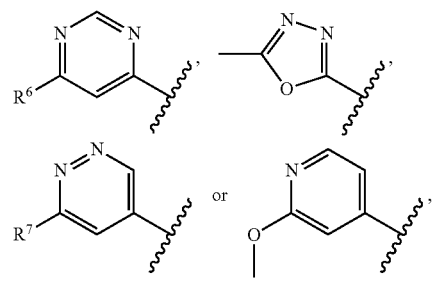

wherein
$R^6$ is hydrogen, lower alkyl, halogen or lower alkoxy; and
$R^7$ is hydrogen, lower alkoxy or halogen;
$R^3$ is lower alkyl or lower alkyl substituted by hydroxy:
$R^4$ is hydrogen or lower alkyl;
$R^5$ is hydrogen or lower alkyl;
n is 1 or 2;
-( )$_n$- is —$CH_2$— or —$CH_2CH_2$— for n being 1 or 2;
or to a pharmaceutically active acid addition salt thereof, to a racemic mixture or to its corresponding enantiomer and/or optical isomer and/or stereoisomer thereof
The compounds may be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

13 Claims, No Drawings

(56) References Cited

OTHER PUBLICATIONS

Clarke et al., "Intra- or Intercomplex Binding to the γ-Secretase Enzyme" Journal of Biological Chemistry 281(42):31279-31289 (Oct. 20, 2006).
Crump et al., "Development and Mechanism of γ-Secretase Modulators for Alzheimer's Disease" Biochemistry 52:3197-3216 ( 2013).
Ebke et al., "Novel γ-Secretase Enzyme Modulators Directly Target Presenilin Protein*S" Journal of Biological Chemistry 286(43):37181-37186 (Oct. 28, 2011).
Hall et al., γ-Secretase Modulators: Current Status and Future Directions Progress in Medicinal Chemistry 53:101-145 ( 2014).
ISR and Written Opinion for PCT/EP2017/067323 (dated Sep. 13, 2017).
Jantzen et al., "Microglial Activation and b-Amyloid Deposit Reduction Caused by a Nitric Oxide-Releasing Nonsteroidal Anti-Inflammatory Drug in Amyloid Precursor Protein Plus Presenilin-1 Transgenic Mice" Journal of Neuroscience 22:2246-2254 (Mar. 15, 2002).
Kukar et al., "Diverse compounds mimic Alzheimer disease-causing mutations by augmenting Ab42 production" Nature Medcine 11:545-550 (May 2005).
Lleo et al., "Nonsteroidal anti-inflammatory drugs lower Ab42 and change presenilin 1 conformation" Nature Medicine 10:1065-1066 (Oct. 2004).
Morihara et al., "Selective inhibition of Aβ42 production by NSAID R-enantiomers" Journal of Neurochemistry 83:1009-1012 ( 2002).
Narlawar et al., "Scaffold of the Cyclooxygenase-2 (COX-2) Inhibitor Carprofen Provides Alzheimer G-Secretase Modulators" Journal of Medicinal Chemistry 49:7588-7591 ( 2006).
Oehlrich et al., "γ-Secretase Modulators as Potential Disease Modifying Anti-Alzheimer's Drugs" Journal of Medicinal Chemistry 54:669-698 ( 2011).
Peretto et al., "Synthesis and Biological Activity of Flurbiprofen Analogues as Selective Inhibitors of B-Amyloidl-42 Secretion" Journal of Medicinal Chemistry 48:5705-5720 ( 2005).
Stock et al., "The geminal dimethyl analogue of Flurbiprofen as a novel Ab42 inhibitor and potential Alzheimer's disease modifying agent" Bioorganic & Medicinal Chemistry Letters 16:2219-2223 ( 2006).
Takahashi et al., "Sulindae Sulfide Is a Noncompetitive γ-Secretase Inhibitor That Preferentially Reduces Ab42 Generation*" Journal of Biological Chemistry 278(20):18664-18670 ( 2003).
Weggen et al., "A subset of NSAIDs lower amyloidogenic Aβ42 independently of cyclooxygenase activity" Nature 414:212-216 (Nov. 8, 2001).

FUSED PYRIMIDINE DERIVATIVES

CROSS-REFERENCE TO RELATED APPLICATIONS

This application is a continuation of, and claims priority to, International Patent Application No. PCT/EP2017/067323, filed on Jul. 11, 2017. This application also claims priority to European Patent Application No. 16179501.8, filed on Jul. 14, 2016. The entire contents of each of the above patent applications are hereby incorporated by reference.

The present invention relates to a compound of formula I,

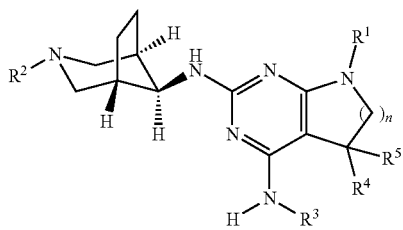

wherein
$R^1$ is phenyl, lower alkyl, $C_{3-6}$-cycloalkyl, —$CH_2$—$C_{3-6}$-cycloalkyl or bridged $C_{4-7}$-cycloalkyl, substituted by one, two or three halogen atoms, or by lower alkyl or lower alkyl substituted by halogen;
$R^2$ is a five or six membered heteroaryl group, selected from

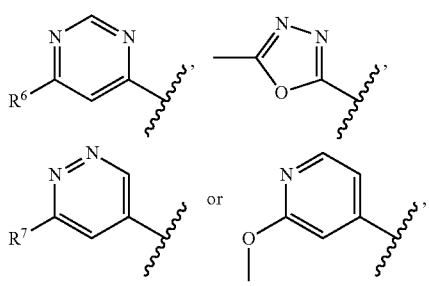

wherein
$R^6$ is hydrogen, lower alkyl, halogen or lower alkoxy; and
$R^7$ is hydrogen, lower alkoxy or halogen;
$R^3$ is lower alkyl or lower alkyl substituted by hydroxy;
$R^4$ is hydrogen or lower alkyl;
$R^5$ is hydrogen or lower alkyl;
n is 1 or 2;
-$()_n$- is —$CH_2$— or —$CH_2CH_2$— for n being 1 or 2;
or to a pharmaceutically active acid addition salt thereof, to a racemic mixture or to its corresponding enantiomer and/or an optical isomer and/or stereoisomer thereof.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, 525, pages 212-217. The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al., Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on γ-secretase modulation, for example the following publications:
Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Oehlich, Gijsen et al, J. Med. Chem., 54 (2011) 669-698
Li et al., Biochemistry, 52 (2013) 3197-3216
Hall et al, Progress in Med. Chem., 53 (2014) 101-145
Bursavich et al, J. Med. Chem., 59 (2016) 7389-7409
The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$, and the like. The preferred group is $CF_3$.

As used herein, the term "lower alkyl substituted by hydroxy" denotes an alkyl group as defined above, wherein at least one hydrogen atom is replaced by hydroxy, for example —$(CH_2)_2OH$.
The term "lower alkoxy" denotes a lower alkyl group as defined above, which group is connected via an O atom.

The term "halogen" denotes chlorine, iodine, fluorine and bromine.

The term "$C_{3-6}$-cycloalkyl" is an alkyl ring system, containing 3 to 6 ring-carbon atoms, for example cyclopropyl, cyclobutyl, cyclopentyl or cyclohexyl.

The term "bridged $C_{4-7}$-cycloalkyl" is an alkyl ring system, containing 4 to 7 ring-carbon atoms, in which two carbon atoms of a basic $C_{3-6}$-cycloalkyl ring system as defined above are bridged by a single bond, —$CH_2$— or —$CH_2CH_2$—.
for example

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

Further objects of the present invention are all forms of optically pure enantiomers, racemates or diastereometric mixtures for compounds of formula I.

One object of the present invention is a compound of formula I-1,

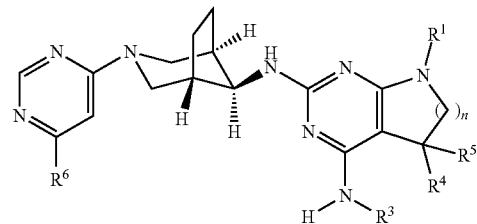

wherein
$R^1$ is phenyl, lower alkyl, $C_{3-6}$-cycloalkyl, —$CH_2$—$C_{3-6}$-cycloalkyl or bridged $C_{4-7}$-cycloalkyl, substituted by one, two or three halogen atoms, or by lower alkyl or lower alkyl substituted by halogen;
$R^3$ is lower alkyl or lower alkyl substituted by hydroxy:
$R^4$ is hydrogen or lower alkyl;
$R^5$ is hydrogen or lower alkyl;
$R^6$ is hydrogen, lower alkyl, halogen or lower alkoxy; and
n is 1 or 2;
-( )$_n$- is —$CH_2$— or —$CH_2CH_2$— for n being 1 or 2;
or a pharmaceutically active acid addition salt thereof, a racemic mixture or its corresponding enantiomer and/or an optical isomer and/or a stereoisomer thereof, for example the following compounds
7-(4-Fluorophenyl)-N4,5,5-trimethyl-N2-((1R,5 S,8s)-3-(6-methylpyrimidin-4-yl)-3-azabicyclo[3.2.1]octan-8-yl)-6,7-dihydro-5H-pyrrolo[2,3-d]pyrimidine-2,4-diamine,
N2-((1R,5S,8s)-3-(6-Chloropyrimidin-4-yl)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine,
7-(4-Fluorophenyl)-N2-((1R,5S,8s)-3-(6-methoxypyrimidin-4-yl)-3-azabicyclo[3.2.1]octan-8-yl)-N4,5,5-trimethyl-6,7-dihydro-5H-pyrrolo[2,3-d]pyrimidine-2,4-diamine,
7-(3,4-Difluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine,
7-(4-Fluorophenyl)-N4-methyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine,
7-(3,3-Difluorocyclobutyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine,
7-(2,4-Difluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine,
N4,5,5-Trimethyl-N2-((1R,5 S,8s)-3-(6-methylpyrimidin-4-yl)-3-azabicyclo[3.2.1]octan-8-yl)-7-(3-(trifluoromethyl)bicyclo[1.1.1]pentan-1-yl)-6,7-dihydro-5H-pyrrolo[2,3-d]pyrimidine-2,4-diamine, 2-((7-(4-Fluorophenyl)-5,5-dimethyl-2-(((1R,5S,8s)-3-(6-methylpyrimidin-4-yl)-3-azabicyclo[3.2.1]octan-8-yl)amino)-6,7-dihydro-5H-pyrrolo[2,3-d]pyrimidin-4-yl)amino)ethanol, 8-(4-Fluorophenyl)-N4,5,5-trimethyl-N2-((1R,5S,8s)-3-(6-methylpyrimidin-4-yl)-3-azabicyclo[3.2.1]octan-8-yl)-5,6,7,8-tetrahydropyrido[2,3-d]pyrimidine-2,4-diamine, 7-(2,3-Difluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine, (R)-7-(4-Fluorophenyl)-N4,5-dimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine, or (S)-7-(4-Fluorophenyl)-N4,5-dimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine.

One further object of the present invention is a compound of formula I-2,

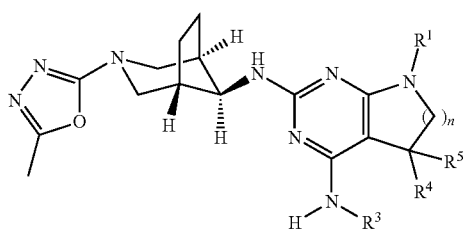

I-2 wherein $R^1$ is phenyl, lower alkyl, $C_{3-6}$-cycloalkyl, —$CH_2$—$C_{3-6}$-cycloalkyl or bridged $C_{4-7}$-cycloalkyl, substituted by one, two or three halogen atoms, or by lower alkyl or lower alkyl substituted by halogen;

$R^3$ is lower alkyl or lower alkyl substituted by hydroxy:

$R^4$ is hydrogen or lower alkyl;

$R^5$ is hydrogen or lower alkyl;

n is 1 or 2;

-( )$_n$- is —$CH_2$— or —$CH_2CH_2$— for n being 1 or 2;

or a pharmaceutically active acid addition salt thereof, a racemic mixture or its corresponding enantiomer and/or an optical isomer and/or stereoisomer thereof, for example the following compounds 7-(4-Fluorophenyl)-N4,5,5-trimethyl-N2-((1R,5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine, 7-(3,4-Difluorophenyl)-N4,5,5-trimethyl-N2-((1R,5 S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine, 7-(3,3-Difluorocyclobutyl)-N4,5,5-trimethyl-N2-((1R,5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine or 7-(2,4-Difluorophenyl)-N4,5,5-trimethyl-N2-((1R,5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine.

One object of the present invention is a compound of formula I-3,

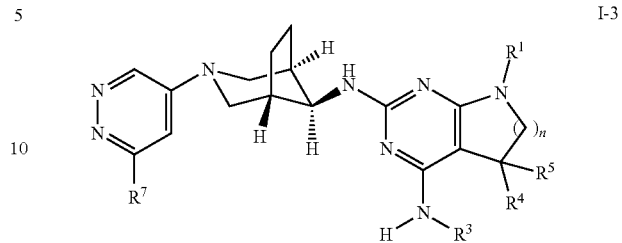

I-3 wherein $R^1$ is phenyl, lower alkyl, $C_{3-6}$-cycloalkyl, —$CH_2$—$C_{3-6}$-cycloalkyl or bridged $C_{4-7}$-cycloalkyl, substituted by one, two or three halogen atoms, or by lower alkyl or lower alkyl substituted by halogen;

$R^3$ is lower alkyl or lower alkyl substituted by hydroxy:

$R^4$ is hydrogen or lower alkyl;

$R^5$ is hydrogen or lower alkyl;

$R^7$ is hydrogen, halogen or lower alkoxy; and n is 1 or 2;

-( )$_n$- is —$CH_2$— or —$CH_2CH_2$— for n being 1, 2 or 3;

or a pharmaceutically active acid addition salt thereof, a racemic mixture or its corresponding enantiomer and/or an optical isomer and/or a stereoisomer thereof, for example the following compounds 7-(4-Fluorophenyl)-N2-((1R,5S,8s)-3-(6-methoxypyridazin-4-yl)-3-azabicyclo[3.2.1]octan-8-yl)-N4,5,5-trimethyl-6,7-dihydro-5H-pyrrolo[2,3-d]pyrimidine-2,4-diamine, N2-((1R,5 S,8s)-3-(6-Chloropyridazin-4-yl)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine, 7-(3,4-Difluorophenyl)-N2-((1R,5S,8s)-3-(6-methoxypyridazin-4-yl)-3-azabicyclo[3.2.1]octan-8-yl)-N4,5,5-trimethyl-6,7-dihydro-5H-pyrrolo[2,3-d]pyrimidine-2,4-diamine, 7-(4-Fluorophenyl)-N4,5,5-trimethyl-N2-((1R,5S,8s)-3-(pyridazin-4-yl)-3-azabicyclo[3.2.1]octan-8-yl)-6,7-dihydro-5H-pyrrolo[2,3-d]pyrimidine-2,4-diamine, N2-((1R,5S,8s)-3-(6-Methoxypyridazin-4-yl)-3-azabicyclo[3.2.1]octan-8-yl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine, 7-(2,4-Difluorophenyl)-N2-((1R,5S,8s)-3-(6-methoxypyridazin-4-yl)-3-azabicyclo[3.2.1]octan-8-yl)-N4,5,5-trimethyl-6,7-dihydro-5H-pyrrolo[2,3-d]pyrimidine-2,4-diamine, 2-((7-(4-Fluorophenyl)-2-(((1R,5S,8s)-3-(6-methoxypyridazin-4-yl)-3-azabicyclo[3.2.1]octan-8-yl)amino)-5,5-dimethyl-6,7-dihydro-5H-pyrrolo[2,3-d]pyrimidin-4-yl)amino)ethanol, 8-(4-Fluorophenyl)-N2-((1R,5S,8s)-3-(6-methoxypyridazin-4-yl)-3-azabicyclo[3.2.1]octan-8-yl)-N4,5,5-trimethyl-5,6,7,8-tetrahydropyrido[2,3-d]pyrimidine-2,4-diamine, or 7-(2,3-Difluorophenyl)-N4,5,5-trimethyl-N2-((1R,5S,8s)-3-(6-methoxypyridazin-4-yl)-3-azabicyclo[3.2.1]octan-8-yl)-6,7-dihydro-5H-pyrrolo[2,3-d]pyrimidine-2,4-diamine.

One object of the present invention is a compound of formula I-4,

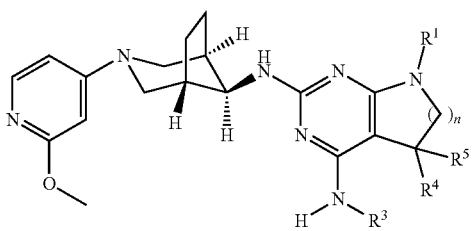

I-4 wherein
R¹ is phenyl, lower alkyl, $C_{3-6}$-cycloalkyl, —CH₂—$C_{3-6}$-cycloalkyl or bridged $C_{4-7}$-cycloalkyl, substituted by one, two or three halogen atoms, or by lower alkyl or lower alkyl substituted by halogen;
R³ is lower alkyl or lower alkyl substituted by hydroxy:
R⁴ is hydrogen or lower alkyl;
R⁵ is hydrogen or lower alkyl;
n is 1 or 2;
-( )ₙ- is —CH₂— or —CH₂CH₂— for n being 1 or 2;
or a pharmaceutically active acid addition salt thereof, a racemic mixture or its corresponding enantiomer and/or an optical isomer and/or a stereoisomer thereof, for example the following compound
7-(4-Fluorophenyl)-N2-((1R,5 S,8s)-3-(2-methoxypyridin-4-yl)-3-azabicyclo[3.2.1]octan-8-yl)-N4,5,5-trimethyl-6,7-dihydro-5H-pyrrolo[2,3-d]pyrimidine-2,4-diamine, or
7-(2,3-Difluorophenyl)-N4,5,5-trimethyl-N2-((1R,5S,8s)-3-(2-methoxypyridin-4-yl)-3-azabicyclo[3.2.1]octan-8-yl)-6,7-dihydro-5H-pyrrolo[2,3-d]pyrimidine-2,4-diamine.

The present compounds of formula I and their pharmaceutically acceptable salts can be prepared by methods known in the art, for example, by processes described below, which processes comprise a) reacting a compound of formula II

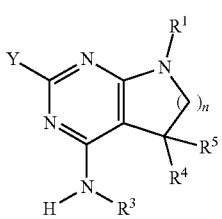

II with a compound of formula III

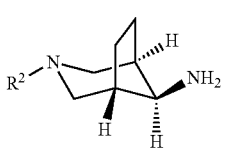

III to a compound of formula I

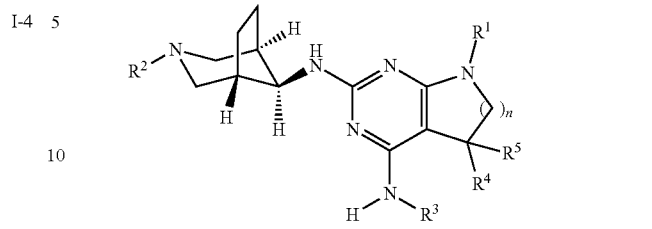

I wherein the substituents have the meaning as described above, and Y is halogen, and, if desired, converting the compounds obtained into pharmaceutically acceptable acid addition salts;
or
b) reacting a compound of formula VI

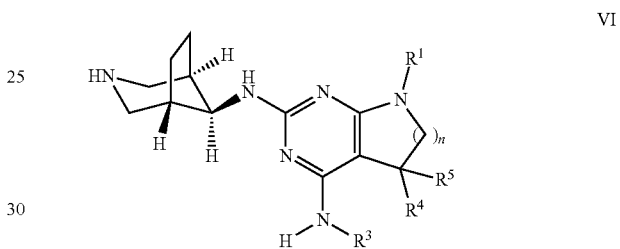

VI with a compound of formula

R²—X to a compound of formula

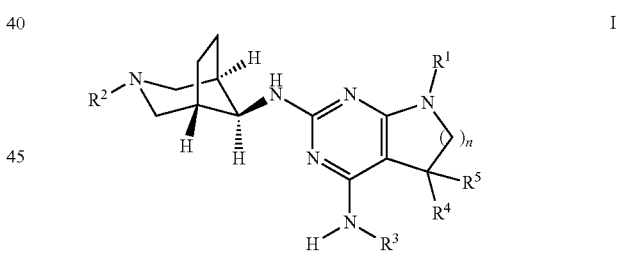

I wherein the groups have the meaning as described above, and X is halogen, or if desired converting the compounds obtained into pharmaceutically acceptable acid addition salts or c) reacting a compound of formula VIII

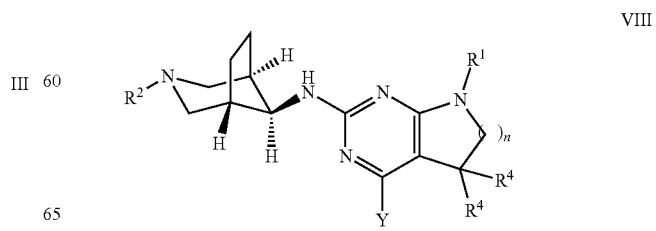

VIII with a compound of formula

to a compound of formula

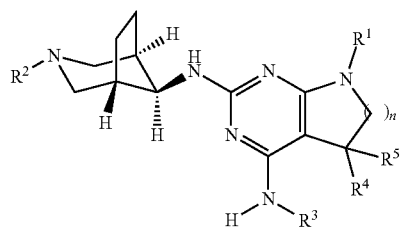

I wherein the groups have the meaning as described above and Y is halogen, or if desired converting the compounds obtained into pharmaceutically acceptable acid addition salts.

In more detail, compounds of formula I and their intermediates may be prepared by schemes 1-11 and by the description of 23 specific examples.

Scheme 1

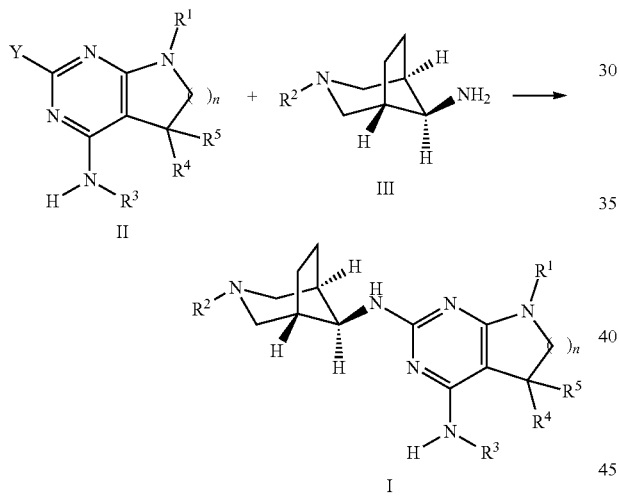

An intermediate of formula II, wherein n, $R^1$, $R^3$, $R^4$, $R^5$ are as defined above and Y is halogen, preferably chorine or bromine, is reacted with a compound of formula III, wherein $R^2$ is as defined above, in the presence of catalytic or stoichiometric amounts of a suitable transition metal complex, e.g. bis(dibenzylideneacetone)palladium(0) or tris(dibenzylideneacetone)di-palladium(0), and, respectively, catalytic or stoichiometric amounts of a suitable phosphine ligand, e.g. 2-dicyclohexylphosphino-2'-(N,N-dimethylamino)biphenyl or Xantphos, and, furthermore, in the presence of a suitable base, e.g. alkali carbonate, alkali tertbutoxide, or alkaliphosphate, e.g. cesium carbonate or sodium tertbutoxide. The reaction can be carried out in a polar, aprotic solvent, e.g. N-methylpyrrolidinone, 1,4-dioxane or dimethylformamide, at temperatures between 100° C. and 170° C., preferably between 140° C. and 160° C., optionally under microwave radiation in a closed vial.

Alternatively, the transformation of intermediates of formula II into compounds of formula I can be achieved under thermal conditions by reacting the intermediates formula II with intermediates of formula III in an appropriate polar protic or aprotic, high-boiling solvent, such as N-methylpyrrolidinone, optionally in the presence of a suitable base, such as a trialkyl amine, e.g. diisopropylethyl amine, at elevated temperatures between 80° C. and 200° C., preferably 130° C. and 160° C.

Scheme 2

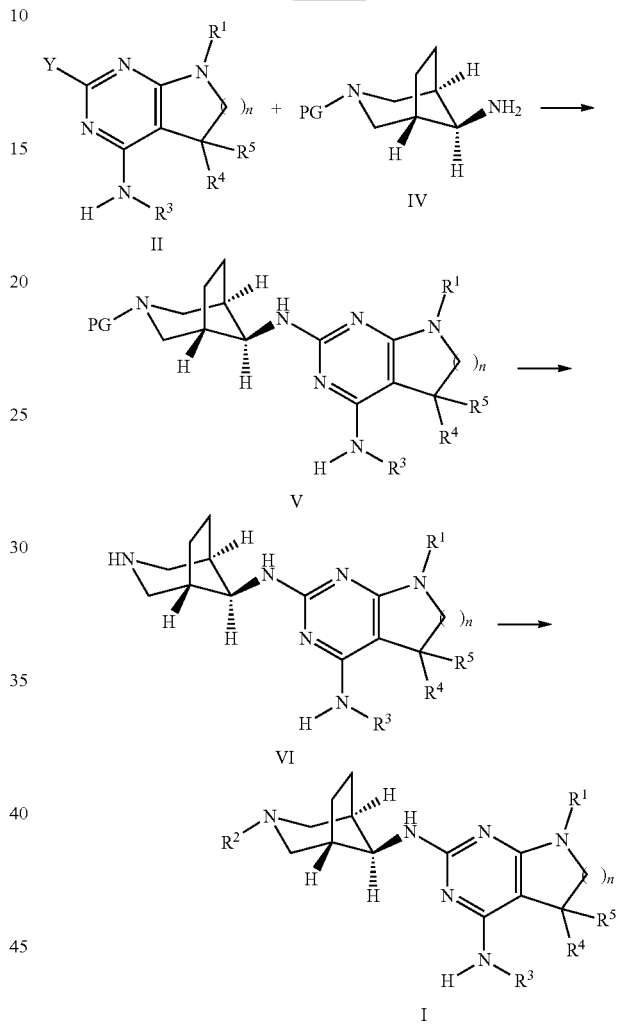

Alternatively, compounds of formula I, wherein n, $R^1$, $R^2$, $R^3$, $R^4$, $R^5$ are as defined above, can be accessed as outlined in Scheme 2. In analogy to the reaction depicted in Scheme 1, an intermediate of formula II, wherein n, $R^1$, $R^3$, $R^4$, $R^5$, are as defined above and Y is halogen, preferably chorine or bromine, can be reacted with a compound of formula IV, wherein PG is a suitable protecting group, e.g. tert-butoxycarbonyl (Boc) in the presence of catalytic or stoichiometric amounts of a suitable transition metal complex, e.g. bis(dibenzylideneacetone)-palladium(0) or tris(dibenzylideneacetone)dipalladium(0), and, respectively, catalytic or stoichiometric amounts of a suitable phosphine ligand, e.g. 2-dicyclohexylphosphino-2'-(N,N-dimethylamino)biphenyl or Xantphos, and, furthermore, in the presence of a suitable base, e.g. alkali carbonate, alkali tertbutoxide, or alkaliphosphate, e.g. cesium carbonate or sodium tertbutoxide. The reaction can be carried out in a polar, aprotic solvent, e.g. N-methylpyrrolidinone, 1,4-dioxane or dimethylformamide, at temperatures between 100° C. and 170° C., preferably between 140° C. and 160° C., optionally under microwave radiation in a closed vial.

Alternatively, the transformation of intermediates of formula II into compounds of formula V can be achieved under thermal conditions by reacting the intermediates formula II with intermediates of formula IV in an appropriate polar protic or aprotic, high-boiling solvent, such as N-methylpyrrolidinone, optionally in the presence of a suitable base, such as a trialkyl amine, e.g. diisopropylethyl amine, at elevated temperatures between 80° C. and 200° C., preferably 130° C. and 160° C.

Next, the protecting group PG can be cleaved using methods known in the art. In case PG is Boc, the deprotection can be achieved by stirring the intermediate of formula V in the presence of a strong acid, such as triflouroacetic acid (TFA) or hydrochloric acid (HCl) as solution in dioxane or water, optionally in the presence of a suitable solvent, e.g. dichloromethane. The resulting intermediate of formula VI can be transformed into a compound of formula I by reaction with (het)aryl halide $R^2$—X, wherein $R^2$ is as defined above and X is halogen, preferably chlorine or bromine, in the presence of a suitable base, such as a trialkyl amine, e.g. triethyl amine, in an appropriate polar protic or aprotic solvent, e.g. ethanol, at temperatures between 50° C. and 130° C., preferably 70° C. to 100° C.

Alternatively, compounds of formula I can be synthesised as shown in Scheme 3 in a two step process.

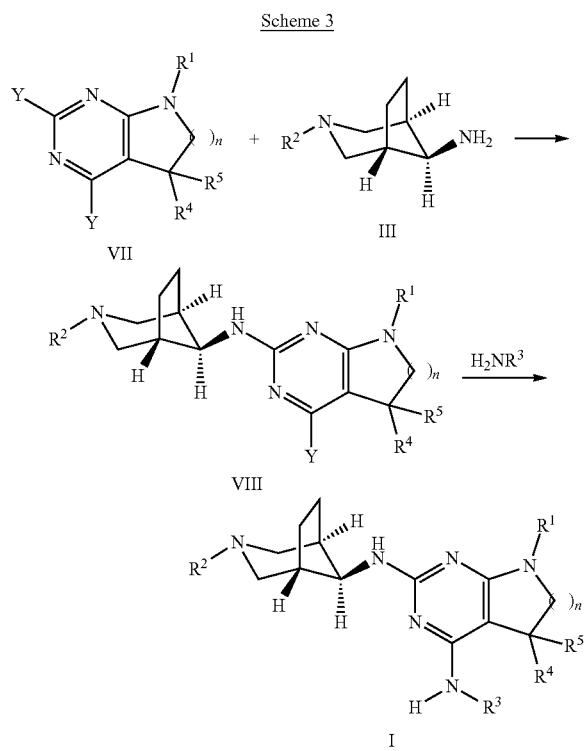

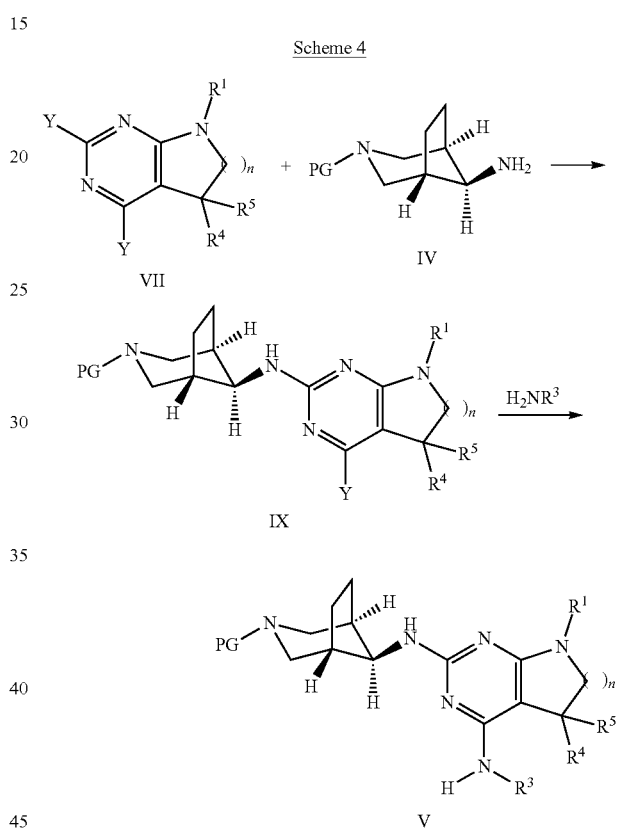

In the first step, an intermediate of formula VII, Y is each independently selected from halogen, preferably chorine, is reacted with a compound of formula III, wherein $R^2$ is as defined above, optionally in the presence of a suitable base, e.g. trialkylamine, such as triethylamine or diisopropylethyl amine, in a polar protic or aprotic solvent, e.g. N-methylpyrrolidinone or ethanol, or a mixture thereof, at elevated temperatures between 80° and 160° C., preferably between 110° C. and 130° C. The second step, reaction of intermediate VIII with an amine of formula $H_2NR^3$, wherein $R^7$ is as defined above, can be carried out using an excess of amine $H_2NR^3$, optionally as solution in a suitable solvent, such as ethanol or methanol. The transformation can be carried out at elevated temperatures of 100° C. to 140° C., preferably between 110° C. and 130° C., in a polar protic or aprotic solvent, e.g. N-methylpyrrolidinone or ethanol, or mixtures thereof. For amines having a low boiling point, such as methylamine or ethylamine, the reaction is best carried out in a closed pressure vial or autoklave at high concentrations.

Alternatively, in analogy to the sequence depicted in Scheme 3 a compound of formula VII, wherein n, $R^1$, $R^4$, $R^5$ are as defined above and Y is each independently selected from halogen, preferably chorine, can be transformed to a compound of formula V wherein n, $R^1$, $R^3$, $R^4$, $R^5$ are as defined above by reaction with a compound of formula IV, wherein PG is a suitable protecting group, such as tertbutoxycarbonyl (Boc), using similar reaction conditions as described above. The resulting compound of formula V can then be transformed into compounds of formula I, as already outlined in Scheme 2.

Alternatively, the single steps, depicted in Scheme 4 and Scheme 2, can be exchanged as appropriate. Likewise, as example, a compound of formula IX can be deprotected, then reacted with a compound of formula $R^2$—X, wherein $R^2$ is as defined above and X is halogen, preferably chlorine or bromine, and finally reacted with an amine of formula $R^3$—$NH_2$, wherein $R^3$ is as defined above, to give access to final compounds of formula I.

Scheme 5

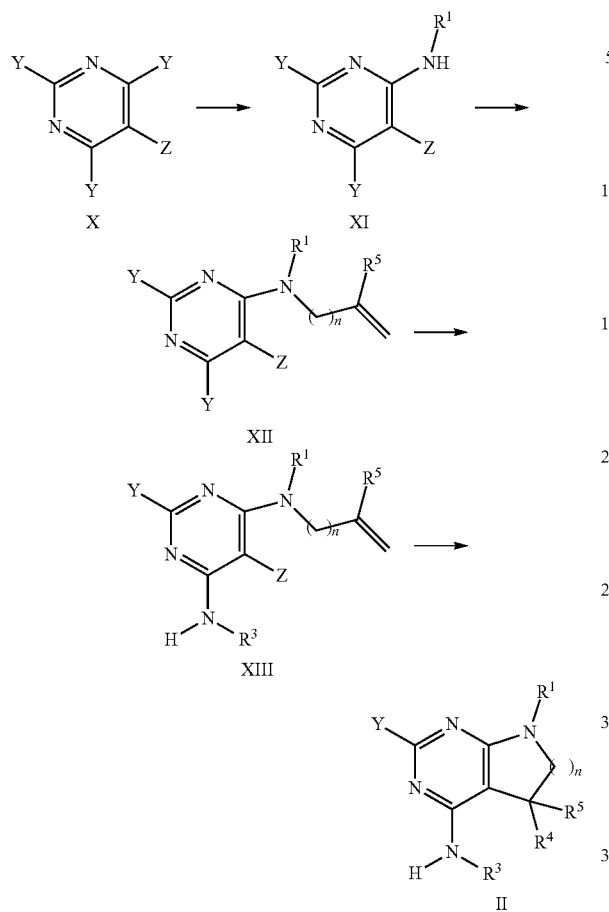

The intermediates of formula II can be prepared by methods known in the art. For example, intermediates of formula II, wherein $R^1$, $R^3$, $R^4$ and $R^5$ are as defined above with the exception $R^5$ is not hydrogen, and $R^4$ is methyl, can be accessed using the synthetic sequence depicted in Scheme 5. Pyrimidines of formula X, wherein Y is each individually selected from halogen, preferably chlorine, and Z is selected from halogen, preferably bromine, can be reacted with amines of formula $H_2NR^1$, wherein $R^1$ is as defined above, in the presence of a non-nucleophilic base, such as sodium acetate or trialkylamine, e.g. triethyl amine or N,N-diisopropylethyl amine, or alkali hexamethyldisilazide, e.g. lithiumhexamethyldisilazide, in a suitable polar solvent, such as, e.g., tetrahydrofuran, acetonitrile or dichloromethane. Thereafter, the intermediate of formula XI can be reacted with an appropriate alkylating agent LG-[CH$_2$]$_n$C(R$^5$)=CH$_2$, wherein n is 1, 2, 3, preferably 1, and the leaving group LG is halogen or sulfonate OSO$_2$R', e.g. bromine, methylsulfonate, trifluoromethylsulfonate or tolylsulfonate, preferably bromine, and $R^5$ is as defined above, with the exception $R^5$ is not hydrogen, in the presence of a suitable non-nucleophilic base, e.g. sodium hydride, in a polar solvent, e.g. dimethylformamide or N-methylpyrrolidinone, at temperatures of 0° C. to 100° C., preferably between 30° C. and 60° C. Next, the intermediate of formula XII can be transformed into an intermediate of formula XIII by reaction with an amine $H_2NR^3$ in an appropriate polar solvent, e.g. tetrahydrofuran. The resulting mixture of regioisomers can be separated by chromatography or, alternatively, the mixture can be used in the next step and the resulting products separated at this stage. In the next step, the intermediate of formula XIII is cyclised to the intermediate of formula II by means of a Heck reaction. For example, the intermediate of formula XIII can be reacted with substoichiometric or stoichiometric amounts of a suitable transition metal containing compound, e.g. palladium (II) acetate, optionally in the presence of a suitable phosphine ligand, for example triphenyl phosphine, furthermore in the presence of a suitable base, such as a trialkyl amine, e.g. triethyl amine, and in the presence of a suitable reducing agent, e.g. sodium formate. The reaction can take place in an appropriate polar solvent, e.g. dimethylformamide, N-methylpyrrolidinone, or methanol, optionally in the presence of a suitable tetraalkyl ammonium salt, e.g. tetrabutylammonium chloride, at elevated temperatures of 40° C. to 100° C., preferably 70° C. to 90° C.

Scheme 6

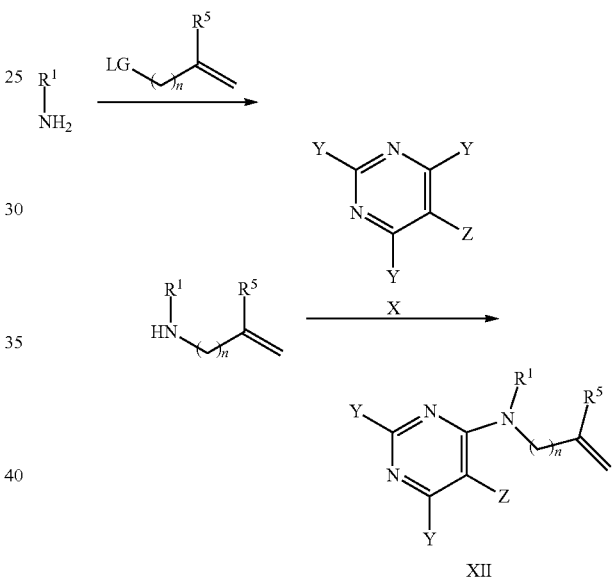

Alternatively, as depicted in Scheme 6, an intermediate of formula XII, wherein Y is each individually selected from halogen, preferably chlorine, and Z is selected from halogen, preferably bromine, n is 1, 2 or 3, and $R^1$, $R^5$ are as defined above with the exception $R^5$ is not hydrogen, can be synthesised by reaction of amines of formula $H_2NR^1$, wherein $R^1$ is as defined above, with an appropriate alkylating agent LG-[CH$_2$]$_n$C(R$^5$)=CH$_2$, wherein n is 1, 2, 3, preferably 1, and the leaving group LG is halogen or sulfonate OSO$_2$R', wherein R' is lower alkyl, optionally substituted by 1-7 fluorine, or phenyl, optionally substituted by 1-2 halogen, nitro or lower alkyl, e.g. bromine, methylsulfonate, trifluoromethylsulfonate or tolylsulfonate, preferably bromine, and $R^5$ is as defined above, with the exception $R^5$ is not hydrogen, in the presence of a suitable base, e.g. alkali carbonate, such as potassium carbonate, or sodium hydride, in an appropriate polar solvent, e.g. dimethylformamide or N-methylpyrrolidinone, at temperatures between 20° C. and 120° C., preferably between 70° C. and 90° C. Next, the resulting intermediate of formula XIV can be reacted with a building block of formula X, wherein Y, Z are as defined above, in the presence of a non nucleophilic base, such as sodium acetate, in a suitable solvent, e.g. tetrahydrofuran, acetonitrile, water, or in a mixture thereof.

Alternatively, a more general access to intermediates of formula VII (n=1) is outlined in Scheme 8.

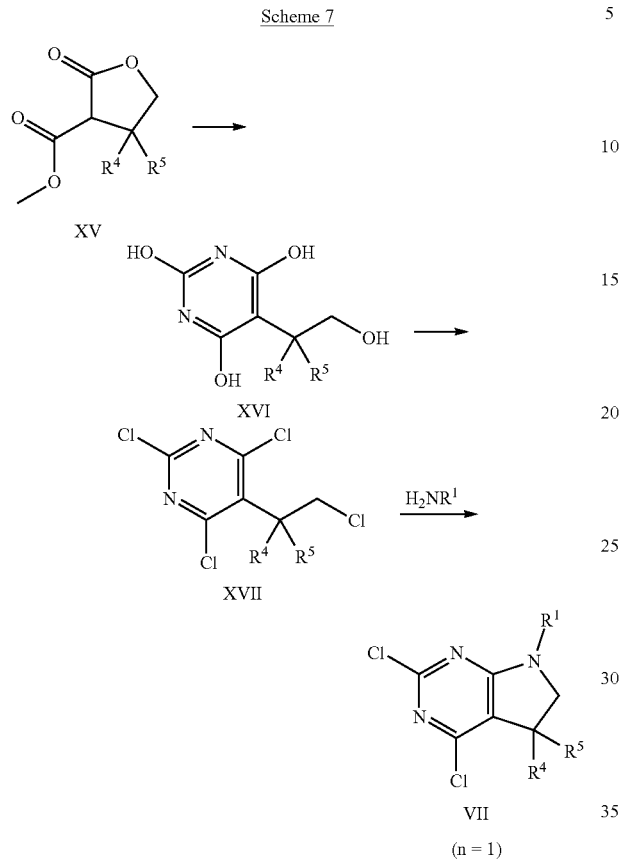

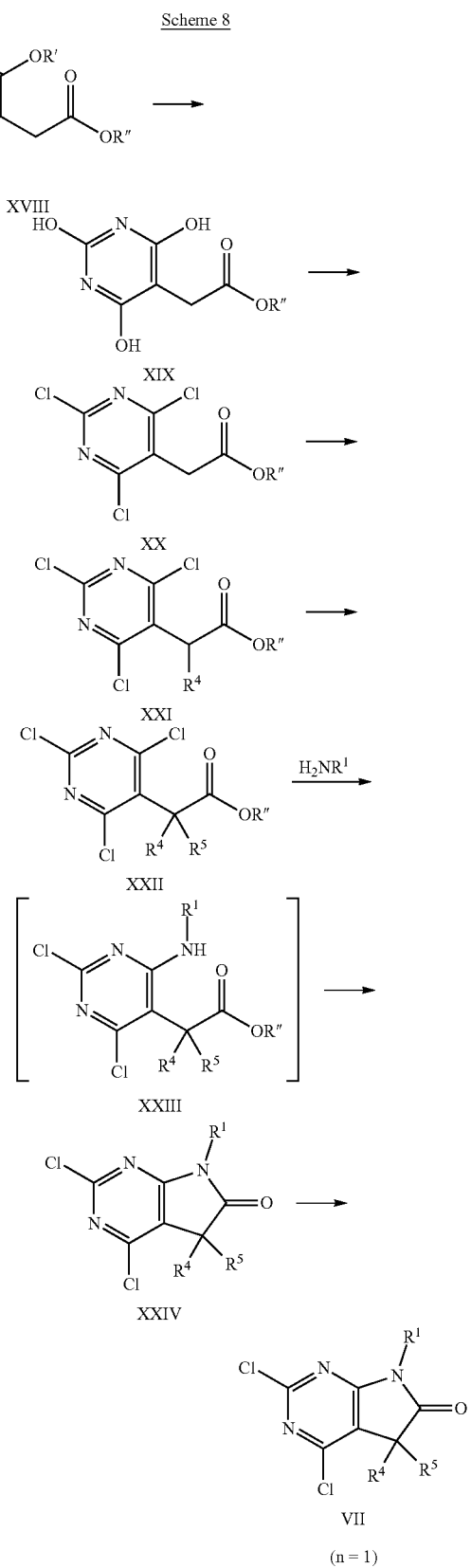

An intermediate of formula VII, wherein n is 1, $R^1$ is as defined above, and $R^4$, $R^5$ are as defined above, preferably hydrogen, can be synthesised according to the sequence depicted in Scheme 7. A compound of formula XV, that is either commercially available or can be accessed as described, e.g., in patent EP2050749 (2009), can be reacted with urea in the presence of at least 1 equivalent, preferably, 2-3 equivalents of a suitable base, such as alkali alkoxide, e.g. sodium ethoxide, in an appropriate polar protic or aprotic solvent, e.g. ethanol, at elevated temperatures of 30° C. to 120° C., preferably 60° C. to 80° C. The crude product of formula XVI, that can be isolated as sodium salt, can thereafter be reacted with a chlorinating agent, such as phosphorus oxychloride, phosphorus pentachloride, or thionyl chloride, optionally in the presence of stoichiometric amounts of N,N-dimethylaniline, at temperatures between 60° C. and 110° C., preferably between 90° C. and 100° C. The resulting intermediate of formula XVII can then be converted into an intermediate of formula VII (n=1, Y=Cl) by reaction with a suitable amine $H_2NR^1$, wherein $R^1$ is as defined above, in the presence of a suitable base, such as trialkyl amine, e.g. diisopropylethyl amine or triethyl amine, in an appropriate polar, aprotic solvent, such as acetonitrile, at temperatures of 30° C. to 70° C., preferably 40° C. to 60° C.

An intermediate of formula XVIII, wherein R', R" are selected from lower alkyl, preferably methyl or ethyl, that is either commercially available or can be synthesised using methods known in the art, e.g. as described in *Chinese Chemical Letters* 2015, 26, pages 619-622, can be condensed with urea in the presence of a suitable base, such as alkali alkoxide, e.g. sodium ethoxide, in an appropriate polar protic or aprotic solvent, e.g. ethanol. Next, the intermediate of formula XIX can be converted into the trichloropyrimidine of formula XX under standard chlorination conditions known in the art, for example by treatment with phosphorus oxychloride, phosphorus pentachloride, or thionyl chloride e.g. by treatment with phosphorus oxychloride, in the presence of a suitable base, e.g. a trialkyl amine, such as diisopropylethyl amine, optionally in the presence of an appropriate solvent, e.g. toluene, at elevated temperatures of 60° C. to 130° C., preferably 80° C. to 110° C. The resulting intermediate of formula XX can thereafter be alkylated using a strong non nucleophilic base, such as alkali hexamethyldisilazide or alkali diisopropylamide, such as lithium hexamethyldisilazide (LHMDS) or lithium diisopropylamide (LDA), under anhydrous conditions in a suitable solvent, e.g. tetrahydrofuran, and in the presence of ca. 1 equivalent of the appropriate alkylating agent $R^4$—X, wherein $R^4$ is as defined above but not hydrogen, X is halogen or $OSO_2R'$, wherein R' is lower alkyl, optionally substituted by 1-7 fluorine, or phenyl, optionally substituted by 1-2 halogen, nitro or lower alkyl, e.g. bromine, methylsulfonate, trifluoromethylsulfonate or tolylsulfonate, preferably bromine, or iodine. The reaction is carried out at low temperatures of −80° C. to room temperature. Optionally, this alkylation step can be repeated using similar conditions and an alkylation agent $R^5$—X, wherein $R^5$ is as defined above but not hydrogen, X is halogen or $OSO_2R'$, wherein R' is lower alkyl, optionally substituted by 1-7 fluorine, or phenyl, optionally substituted by 1-2 halogen, nitro or lower alkyl, e.g. bromine, iodine methylsulfonate, trifluoromethylsulfonate or tolylsulfonate, preferably bromine, or iodine. In case $R^5$ is hydrogen, intermediate XVIII is identical with intermediate XVII. Thereafter, the intermediate of formula XXII can be transformed into the intermediate of formula XXIV by reaction with amine $H_2NR^1$, wherein $R^1$ is as defined above, in the presence of a suitable base, such as trialkyl amine, e.g. diisopropylethyl amine, in a suitable polar solvent, e.g. tetrahydrofuran, at elevated temperatures of 30° C. to 100° C., preferably 50° C. to 80° C. The reaction takes place via intermediate of formula XXIII, that can not be isolated but cyclises immediately under some reaction conditions. In some cases, the intermediate of formula XXIII can be isolated. In these cases, the cyclisation to the intermediate of formula XXIV can be achieved by treatment with an appropriate strong non nucleophilic base, such as alkali bis(trialkylsilyl)amide or alkali diisopropylamide, e.g. lithium bis(trimethylsilyl)amide, in a suitable polar aprotic solvent, e.g. tetrahydrofuran, under anhydrous conditions. The resulting oxindole (intermediate of formula XXIV) can then be reduced to give the desired intermediate of formula VII (n=1) by reaction with an appropriate reducing agent, such as a borane, e.g. borane tetrahydrofuran complex, in a suitable polar, aprotic solvent, e.g. tetrahydrofuran, under anhydrous conditions, and at temperatures between 0° C. and 100° C. Preferably, the addition of the borane is done at lower temperatures, whereas the reaction is best carried out at higher temperatures.

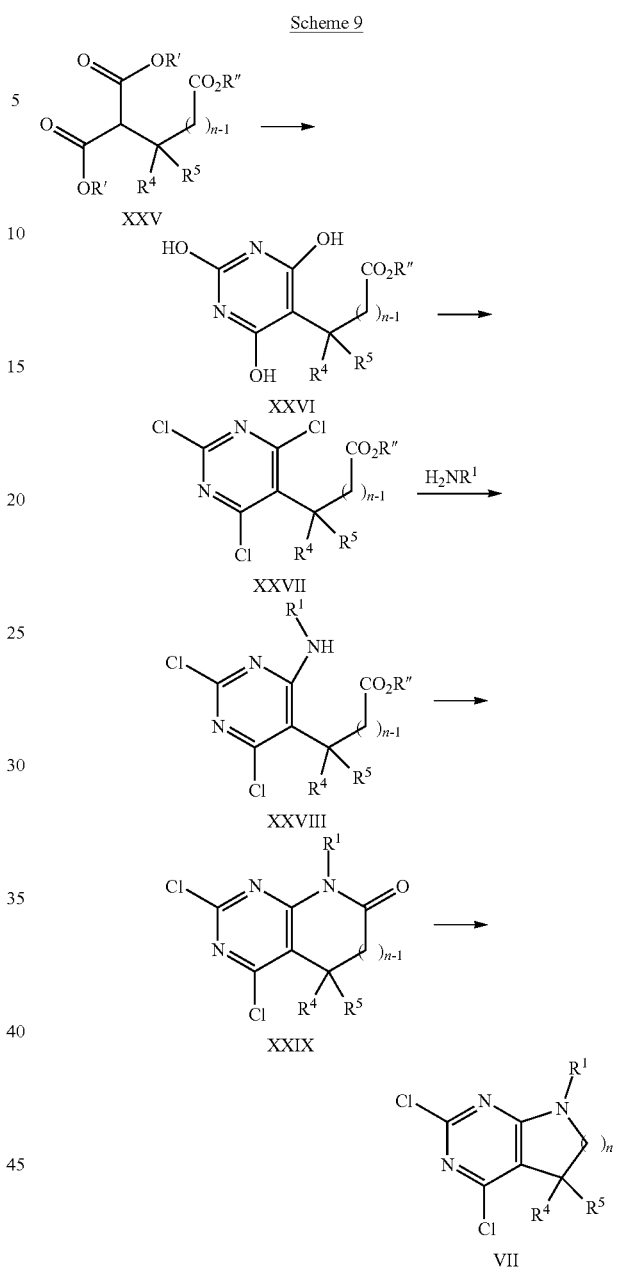

Scheme 9

Alternatively, a more general route to intermediates of formula VII is depicted in Scheme 9. In analogy to the sequence described in Scheme 8, an intermediate of formula XXV, that is either commercially available or can be synthesised by methods known in the art, can be transformed into an intermediate of formula VII via the same sequence of urea condensation, chlorination, amine substitution, cyclisation and reduction, that is described above and using similar methods, respectively, or other methods known in the art.

In case of $R^4$ is not the same as $R^5$, a pair of enantiomers exists for all compounds that contain $R^4$ and $R^5$. The two enantiomers can be separated either as final compounds of formula I or at the stage of an intermediate of formulas II to XXIX, preferably an advanced intermediate, e.g. an intermediate of formula II or VII, by means known in the art, e.g.

by chromatography on a stationary phase that consists of chiral material (preparative chiral chromatography).

Scheme 10

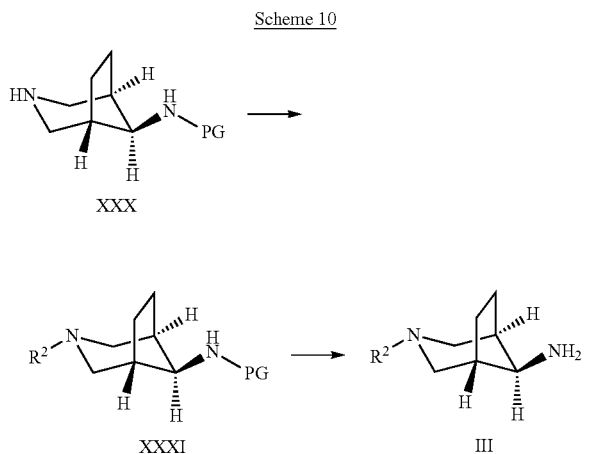

XXX

XXXI    III

Intermediates of formula III, wherein R² is as defined above, are either commercially available or can be synthesized by methods known in the art, e.g. as described in WO2012/116965. Alternatively, they can be accessed according to the general route depicted in Scheme 10. A compound of formula XXX, wherein PG is a suitable protecting group, e.g. tertbutoxycarbonyl (Boc), and that can be synthesized (for PG=Boc) according to procedures described in WO2012/116965, can be reacted with a reagent of formula R²—X, wherein R² is as defined above and X is halogen, in the presence of a suitable base, such as trialkyl amine, e.g. triethyl amine, in an appropriate polar protic or aprotic solvent, e.g. ethanol, at elevated temperatures of 70° C. to 150° C., preferably 90° C. to 130° C.

Alternatively, compounds of formula XXX can be reacted with halides of formula R²—X, wherein R² and X are as defined above, in the presence of catalytic or stoichiometric amounts of a suitable transition metal complex, e.g. bis (dibenzylideneacetone)palladium(0) or tris(dibenzylideneacetone)dipalladium(0), or palladium(II)acetate and, respectively, catalytic or stoichiometric amounts of a suitable phosphine ligand, e.g. dicyclohexyl[2',4',6'-tris(1-methylethyl)[1,1'-biphenyl]-2-yl]phosphine ("X-Phos") or 2,2'-bis(diphenylphosphanyl)-1,1'-binaphthyl ("BINAP"), and, furthermore, in the presence of a suitable base, e.g. alkali carbonate, alkali tertbutoxide, or alkaliphosphate, e.g. cesium carbonate or sodium tertbutoxide. The reaction can be carried out in an aprotic solvent, e.g. N-methylpyrrolidinone, 1,4-dioxane or toluene, at temperatures between 80° C. and 130° C., preferably between 90° C. and 120° C., optionally under microwave radiation in a closed vial.

Next the protecting group can be cleaved to give the desired compounds of formula III using methods known in the art. In case PG is Boc, this transformation can be achieved by reaction with an excess of a strong acid, e.g. trifluoroacetic acid (TFA) or hydrochloric acid in a suitable solvent, e.g. dichloromethane, ethanol, or water, or mixtures thereof.

The halides of formula R²—X are either commercially available, known in the literature so they can be prepared by methods known in the art.

Scheme 11

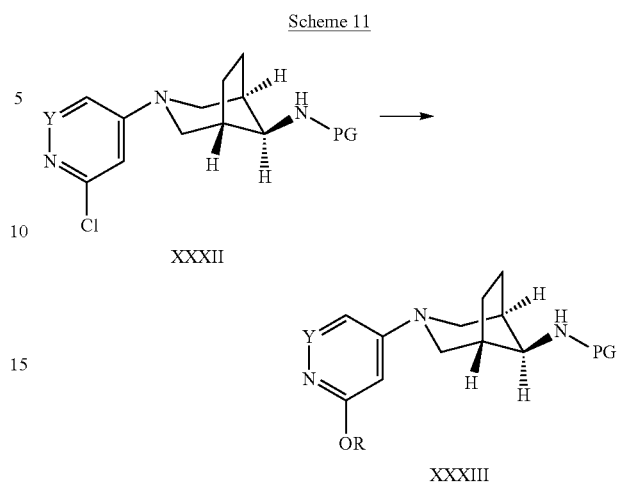

XXXII

XXXIII

Alternatively, certain compounds of formula III can be synthesized via intermediates depicted in Scheme 11. Likewise, a compound of formula XXXII, wherein PG is a suitable protecting group, e.g. Boc, and Y is N or CH, that is a special case of a compound of formula XXXI and that can be prepared according to the reaction shown in Scheme 10, can be reacted with alkoxides of formula MOR, wherein M is an alkali metal, e.g. sodium, and R is lower alkyl, e.g. methyl, in a suitable polar solvent, such as N-methylpyrrolidinone or an alcohol, preferably ROH, wherein R is the same as in the reagent MOR, at elevated temperatures of 50° C. to 120° C., preferably 80° C. to 90° C. The resulting intermediate of formula XXXIII is again a special case of the intermediate of formula XXXI and can be deprotected to give compounds of formula III, as outined in Scheme 10.

The compounds were investigated in accordance with the test given hereinafter.

Description of γ-Secretase Assay

Cellular γ-Secretase Assay

Human neuroglioma H4 cells overexpressing human APP695 with the Swedish double mutation (K595N/M596L) were plated at 30,000 cells/well/100 μl in 96-well plates in IMDM media containing 10% FCS, 0.2 mg/l Hygromycin B and incubated at 37° C., 5% $CO_2$.

3-4 hr post plating, compounds are a diluted in media and 50 μl is added as 1.5-fold concentrate to achieve the final concentration. Compound incubation is performed for 24 hr. Final doses typically range from 4 μM down to 0.0013 μM in half-log steps resulting in a eight point dose response curve. Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat # AL203C, Perkin Elmer). 20 μl of the cell culture supernatant was transferred to an assay plate. Then 10 μl of a mixture of the AlphaLisa coupled capture antibody and the biotinylated detection antibody was added and incubated for 3 hours at room temperature while softly shaking the assay plate. After a further addition of 20 μl of the Donor beads the assay plate was incubated for 30 min at room temperature and constant shaking without exposure to direct light. The assay plate was then read on a Paradigm AlphaLisa Reader using the build-in program with excitation at 680 nm and emission at 570 nm.

The measured signals were then used to calculate $IC_{50}$ values for inhibition of Aβ42 secretion by nonlinear regression fit analysis using XLfit 5.3 software (IDBS).

The table below shows the data for all compounds for the inhibition of Aβ42 secretion (nM):

| Example No. | $EC_{50}$ Aβ42 (nM) | Example No. | $EC_{50}$ Aβ42 (nM) |
|---|---|---|---|
| 1 | 14 | 2 | 34 |
| 3 | 12 | 4 | 23 |
| 5 | 31 | 6 | 46 |
| 7 | 11 | 8 | 33 |
| 9 | 24 | 10 | 12 |
| 11 | 16 | 12 | 19 |
| 13 | 36 | 14 | 104 |
| 15 | 14 | 16 | 31 |
| 17 | 111 | 18 | 53 |
| 19 | 9 | 20 | 12 |
| 21 | 9 | 22 | 35 |
| 23 | 24 | 24 | 9 |
| 25p | 16 | 25q | 17 |
| 26 | 6 | 27 | 10 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL PART

The following examples are provided for illustration of the invention. They should not be considered as limiting the scope of the invention, but merely as being representative thereof.

General
Analytical Methods
HPLC (method LCMS_fastgradient)
Column: Agilent Zorbax Eclipse Plus C18, Rapid Resolution HT, 2.1×30 mm, 1.8 μm, Part. no. 959731-902

Solvent A: Water 0.01% Formic Acid; Solvent B: acetonitrile (MeCN) Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

Abbreviations

The following abbreviations were used in the experimental part:
THF=tetrahydrofurane;
TBME=methyl-tert-butylether;
DMF=dimethylformamide;
TLC=thin layer chromatography;
RT=room temperature, 20-25° C.

Intermediates

Int-5: 2-Chloro-7-(4-fluorophenyl)-N,5,5-trimethyl-6,7-dihydro-5H-pyrrolo[2,3-d]pyrimidin-4-amine

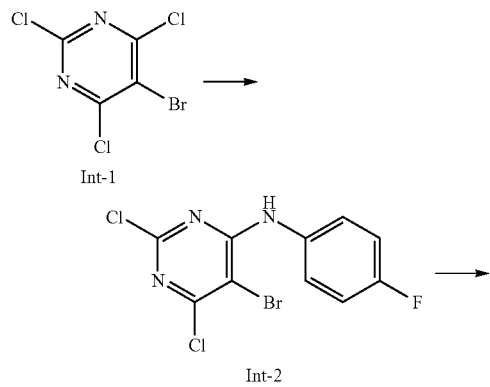

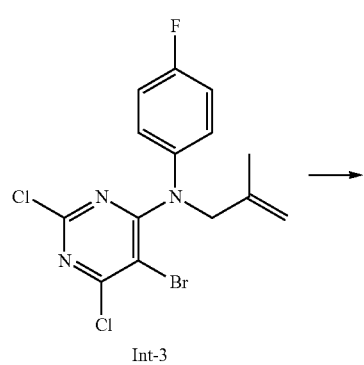

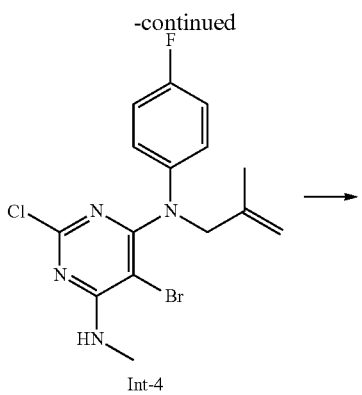

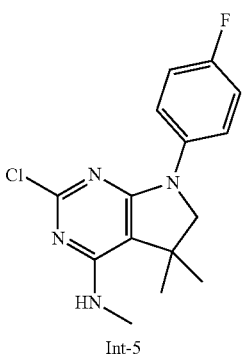

Step 1: 5-Bromo-2,6-dichloro-N-(4-fluorophenyl)pyrimidin-4-amine (Int-2)

5-Bromo-2,4,6-trichloropyrimidine (1.880 g, 6.81 mmol) was dissolved in THF (11 mL) and water (5 mL), and sodium acetate (1.68 g, 20.4 mmol), followed by 4-fluoroaniline (787 mg, 0.68 mL, 6.87 mmol) were added. The mixture was stirred at room temperature for 18 h. After that, a saturated aqueous solution of sodium hydrogencarbonate (15 mL) was added and the resulting mixture was extracted with ethyl acetate (2×150 mL). The combined organic layers were dried (sodium sulfate) and concentrated in vacuo. The crude was purified by column chromatography (silica gel, 40 g, eluting with ethyl acetate/n-heptane, gradient 0:100 to 10:90) to afford, after drying in vacuo (40° C., 5 mbar), the title compound as a light brown solid (2.07 g, 90%). HPLC (method LCMS_fastgradient) $t_R$=1.36 min. $^1$H NMR (CDCl$_3$, 300 MHz): δ 7.12 (dd, J=8.3, 9.1 Hz, 2H), 7.43 (br s, 1H), 7.52 (dd, J=4.6, 8.9 Hz, 2H). MS (ES+) m/z 335.9, 337.9, 339.9 [M+H, Br & 2 Cl isotopes].

Step 2: 5-Bromo-2,6-dichloro-N-(4-fluorophenyl)-N-(2-methylallyl)pyrimidin-4-amine (Int-3)

5-Bromo-2,6-dichloro-N-(4-fluorophenyl)pyrimidin-4-amine (Int-2, 1.45 g, 4.3 mmol) was dissolved in dimethylformamide (14 mL) and sodium hydride (60% dispersion in mineral oil, 239 mg, 5.98 mmol) was added carefully (gas evolution). The mixture was stirred at room temperature for 1 h. Then, 3-bromo-2-methylprop-1-ene (964 mg, 6.93 mmol) was added and the resulting mixture was stirred for 18 h at room temperature. After that, water (20 mL) was added, the mixture was extracted with methyltertbutyl ether (2×150 mL), the organic phases were washed with water (3×20 mL) and brine (20 mL), combined, dried (sodium sulfate), and concentrated in vacuo. The crude product was purified by column chromatography (silica gel, 120 g, eluting with ethyl acetate/n-heptane, gradient 0:100 to 5:95) to give the title compound as yellow oil (1.294 g, 69%). HPLC (method LCMS_fastgradient) $t_R$=1.63 min. $^1$H NMR (CDCl$_3$, 300 MHz): δ 1.80 (s, 3H), 4.58 (s, 2H), 4.85-4.93 (m, 2H), 7.00-7.09 (m, 4H). MS (ES+) m/z 390.0, 392.0, 394.0 [M+H, Br & 2 Cl isotopes].

Step 3: 5-Bromo-2-chloro-N4-(4-fluorophenyl)-N6-methyl-N4-(2-methylallyl)-pyrimidine-4,6-diamine (Int-4)

5-Bromo-2,6-dichloro-N-(4-fluorophenyl)-N-(2-methylallyl)pyrimidin-4-amine (Int-3, 0.830 g, 1.91 mmol) was dissolved in tetrahydrofuran (1.9 mL) and a solution of methylamine in tetrahydrofuran (2.0 M, 3.8 mL, 7.6 mmol) was added dropwise. The mixture was stirred at room temperature for 18 h. After that, water (10 mL) was added, the mixture was extracted with ethyl acetate (2×90 mL), the organic layers were washed with brine (50 mL), combined, dried (sodium sulfate) and concentrated in vacuo. The crude product was purified by column chromatography (silica gel, 40 g, eluting with ethyl acetate/n-heptane, gradient 0:100 to 5:95) to afford the title compound as an off-white solid (396 mg, 51%). HPLC (method LCMS_fastgradient) $t_R$=1.55 min. $^1$H NMR (CDCl$_3$, 300 MHz): δ 1.78 (s, 3H), 3.05 (d, J=5.0 Hz, 3H), 4.52 (s, 2H), 4.84-4.89 (m, 1H), 4.91-4.95 (m, 1H), 5.48-5.56 (m, 1H), 6.94-7.00 (m, 4H). MS (ES+) m/z 385.0, 387.0, 389.0 [M+H, Br & Cl isotopes].

Step 4: 2-Chloro-7-(4-fluorophenyl)-N,5,5-trimethyl-6,7-dihydro-5H-pyrrolo[2,3-d]pyrimidin-4-amine (Int-5)

5-Bromo-2-chloro-N4-(4-fluorophenyl)-N6-methyl-N4-(2-methylallyl)pyrimidine-4,6-diamine (Int-4, 390 mg, 1.01 mmol), sodium formate (73 mg, 1.07 mmol), tetrabutylammonium chloride (287 mg, 1.03 mmol) and palladium (II) acetate (52 mg, 0.232 mmol) were charged under argon in a 25 mL round bottomed flask. Dimethylformamide (3.2 mL), followed by triethylamine (261 mg, 2.58 mmol) were added and the flask was evacuated carefully and backfilled with argon. The resulting mixture was stirred at 80° C. for 18 h. After cooling, water (5 mL) was added, the mixture was extracted with methyltertbutyl ether (2×60 mL), the organic layers were washed with water (3×10 mL) and brine (1×10 mL), combined, dried (sodium sulfate) and concentrated in vacuo. The crude product was purified by column chromatography (silica gel, 25 g, eluting with ethyl acetate/n-heptane, gradient 0:100 to 20:80) to afford the title compound as a yellow solid (259 mg, 83%). HPLC (method LCMS_fastgradient) $t_R$=1.41 min. $^1$H NMR (CDCl$_3$, 300 MHz): δ 1.42 (s, 6H), 3.07 (d, J=4.8 Hz, 3H), 3.71 (s, 2H), 4.25-4.34 (m, 1H), 7.06 (dd, J=8.5, 9.3 Hz, 2H), 7.58 (dd, J=4.6, 9.3 Hz, 2H). MS (ES+) m/z 307.1, 309.1 [M+H, Cl isotopes].

Int-9: 2-Chloro-7-(3,4-difluorophenyl)-N,5,5-trimethyl-6,7-dihydro-5H-pyrrolo[2,3-d]pyrimidin-4-amine

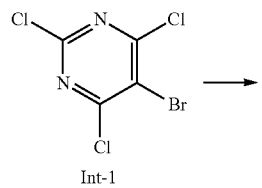

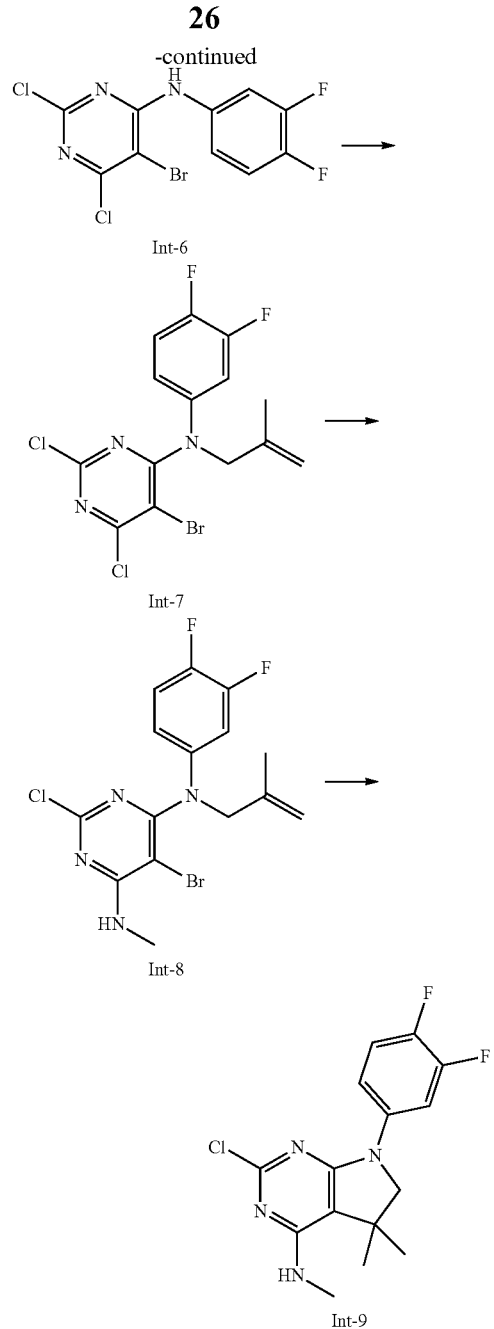

Step 1: 5-Bromo-2,6-dichloro-N-(3,4-difluorophenyl)pyrimidin-4-amine (Int-6)

5-Bromo-2,4,6-trichloropyrimidine (3.00 g, 10.9 mmol) was dissolved in THF (18 mL) and water (9 mL), and sodium acetate (2.67 g, 32.6 mmol), followed by 3,4-difluoroaniline (1.43 g, 1.10 mL, 11.1 mmol) were added. The mixture was stirred at room temperature for 18 h. After that, a saturated aqueous solution of sodium hydrogencarbonate (30 mL) was added and the resulting mixture was extracted with ethyl acetate (2×150 mL). The combined organic layers were dried (sodium sulfate) and concentrated in vacuo. The crude was purified by column chromatography (silica gel, 120 g, eluting with ethyl acetate/n-heptane, gradient 0:100 to 10:90) to afford, after drying in vacuo (40° C., 5 mbar), the title compound as a light yellow solid (3.32 g, 86%). HPLC (method LCMS_fastgradient) $t_R$=1.37 min. $^1$H NMR (CDCl$_3$, 300 MHz): δ 7.17-7.24 (m, 2H), 7.43 (br s, 1H), 7.59-7.68 (m, 1H). MS (ES+) m/z 353.9, 355.9, 357.8 [M+H, Br & 2 Cl isotopes].

Step 2: 5-Bromo-2,6-dichloro-N-(3,4-difluorophenyl)-N-(2-methylallyl)pyrimidin-4-amine (Int-7)

5-Bromo-2,6-dichloro-N-(3,4-difluorophenyl)pyrimidin-4-amine (Int-6, 3.32 g, 9.35 mmol) was dissolved in dimethylformamide (30 mL) and sodium hydride (60% dispersion in mineral oil, 520 mg, 13 mmol) was added carefully (gas evolution). The mixture was stirred at room temperature for 1 h. Then, 3-bromo-2-methylprop-1-ene (2.14 mg, 15.4 mmol) was added and the resulting mixture was stirred for 4.5 h at room temperature, followed by 16 h at 60° C. After that, water (20 mL) was added, the mixture was extracted with methyltertbutyl ether (2×150 mL), the organic phases were washed with water (3×20 mL) and brine (20 mL), combined, dried (sodium sulfate), and concentrated in vacuo. The crude product was purified by column chromatography (silica gel, 120 g, eluting with ethyl acetate/n-heptane, gradient 0:100 to 5:95) to give the title compound as a light yellow oil (3.54 g, 83%). HPLC (method LCMS_fastgradient) $t_R$=1.59 min. $^1$H NMR (CDCl$_3$, 300 MHz): δ 1.79 (d, J=0.6 Hz, 3H), 4.59 (s, 2H), 4.86-4.89 (m, 1H), 4.91-4.95 (m, 1H), 6.76-6.83 (m, 1H), 6.97 (ddd, J=2.7, 6.8, 11.0 Hz, 1H), 7.08-7.19 (m, 1H). MS (ES+) m/z 408.0, 410.0, 411.9 [M+H, Br & 2 Cl isotopes].

Step 3: 5-Bromo-2-chloro-N4-(3,4-difluorophenyl)-N6-methyl-N4-(2-methylallyl)-pyrimidine-4,6-diamine (Int-8)

5-Bromo-2,6-dichloro-N-(3,4-difluorophenyl)-N-(2-methylallyl)pyrimidin-4-amine (Int-7, 3.53 g, 7.77 mmol) was dissolved in tetrahydrofuran (15 mL) and a solution of methylamine in tetrahydrofuran (2.0 M, 15.0 mL, 30.0 mmol) was added dropwise. The mixture was stirred at room temperature for 18 h. After that, water (20 mL) was added, the mixture was extracted with ethyl acetate (2×120 mL), the organic layers were washed with brine (20 mL), combined, dried (sodium sulfate) and concentrated in vacuo. The crude product was purified by column chromatography (silica gel, 120 g, eluting with ethyl acetate/n-heptane, gradient 0:100 to 5:95) to afford the title compound as an off-white solid (1.52 g, 48%). HPLC (method LCMS_fastgradient) $t_R$=1.56 min. $^1$H NMR (CDCl$_3$, 300 MHz): δ 1.78 (d, J=0.6 Hz, 3H), 3.06 (d, J=4.8 Hz, 3H), 4.52 (s, 2H), 4.87-4.90 (m, 1H), 4.93-4.96 (m, 1H), 5.52-5.63 (m, 1H), 6.66-6.73 (m, 1H), 6.84 (ddd, J=2.6, 6.8, 11.7 Hz, 1H), 6.98-7.09 (m, 1H). MS (ES+) m/z 403.1, 405.1, 407.0 [M+H, Br & Cl isotopes].

Step 4: 2-Chloro-7-(3,4-difluorophenyl)-N,5,5-trimethyl-6,7-dihydro-5H-pyrrolo[2,3-d]pyrimidin-4-amine (Int-9)

5-Bromo-2-chloro-N4-(3,4-difluorophenyl)-N6-methyl-N4-(2-methylallyl)pyrimidine-4,6-diamine (Int-8, 1.50 g, 3.72 mmol), sodium formate (268 mg, 3.94 mmol), tetrabutylammonium chloride (1.05 g, 3.79 mmol) and palladium (II) acetate (191 mg, 851 µmol) were charged under argon in a 50 mL round bottomed flask. Dimethylformamide (11 mL), followed by triethylamine (944 mg, 9.33 mmol) were added and the flask was evacuated carefully and backfilled with argon. The resulting mixture was stirred at 80° C. for 18 h. After cooling, water (15 mL) was added, the mixture was extracted with methyltertbutyl ether (2×120 mL), the organic layers were washed with water (3×15 mL) and brine (1×15 mL), combined, dried (sodium sulfate) and concentrated in vacuo. The crude product was purified by column chromatography (silica gel, 80 g, eluting with ethyl acetate/n-heptane, gradient 0:100 to 30:70) to afford the title compound as a light yellow solid (839 mg, 69%). HPLC (method LCMS_fastgradient) $t_R$=1.45 min. $^1$H NMR (CDCl$_3$, 300 MHz): δ 1.42 (s, 6H), 3.08 (d, J=4.8 Hz, 3H), 3.69 (s, 2H), 4.28-4.39 (m, 1H), 7.07-7.18 (m, 1H), 7.23-7.30 (m, 1H), 7.67 (ddd, J=2.7, 7.0, 13.1 Hz, 1H). MS (ES+) m/z 325.0, 327.0 [M+H, Cl isotopes].

Int-13: 2-Chloro-7-(2,4-difluorophenyl)-N,5,5-trimethyl-6,7-dihydro-5H-pyrrolo[2,3-d]pyrimidin-4-amine

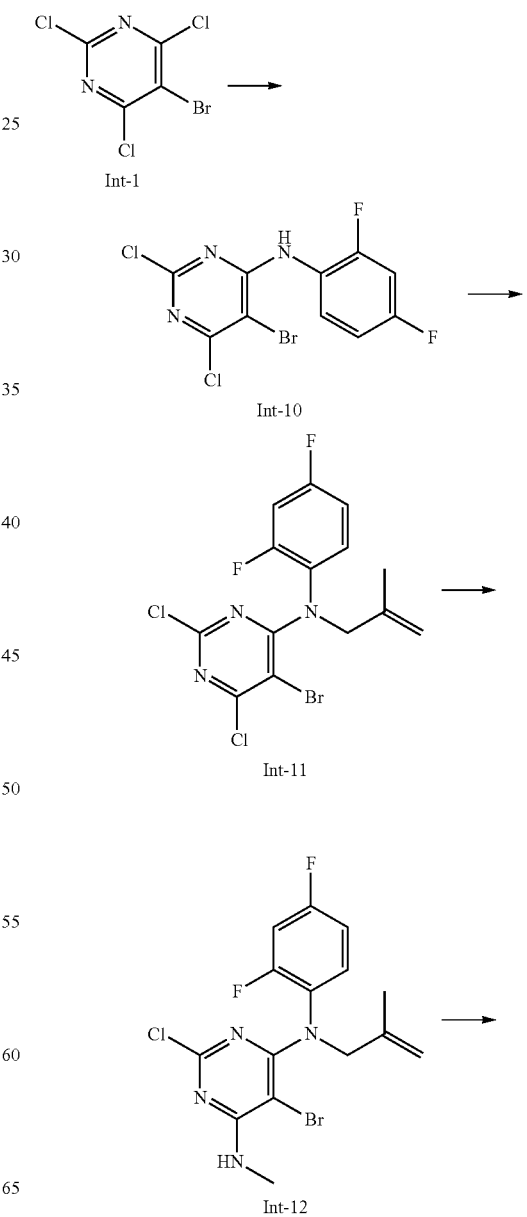

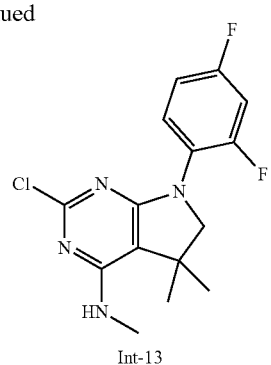

Int-13

Step 1: 5-Bromo-2,6-dichloro-N-(2,4-difluorophenyl)pyrimidin-4-amine (Int-10)

5-Bromo-2,4,6-trichloropyrimidine (2.50 g, 9.05 mmol) was dissolved in THF (16 mL) and water (8 mL), and sodium acetate (2.23 g, 27.2 mmol), followed by 2,4-difluoroaniline (1.18 g, 0.92 mL, 9.14 mmol) were added. The mixture was stirred at room temperature for 18 h. After that, a saturated aqueous solution of sodium hydrogencarbonate (30 mL) was added and the resulting mixture was extracted with ethyl acetate (2×150 mL). The combined organic layers were dried (sodium sulfate) and concentrated in vacuo. The crude was purified by column chromatography (silica gel, 120 g, eluting with ethyl acetate/n-heptane, gradient 0:100 to 5:95) to yield, after drying in vacuo (40° C., 5 mbar), the title compound as an off-white solid (2.22 g, 69%). HPLC (method LCMS_fastgradient) $t_R$=1.39 min. $^1$H NMR (CDCl$_3$, 300 MHz): δ 6.91-7.03 (m, 2H), 7.56 (br s, 1H), 8.16 (ddd, J=5.8, 9.7, 9.7 Hz, 1H). MS (ES+) m/z 353.9, 355.9, 357.9 [M+H, Br & 2 Cl isotopes].

Step 2: 5-Bromo-2,6-dichloro-N-(2,4-difluorophenyl)-N-(2-methylallyl)pyrimidin-4-amine (Int-11)

5-Bromo-2,6-dichloro-N-(2,4-difluorophenyl)pyrimidin-4-amine (Int-10, 2.22 g, 6.25 mmol) was dissolved in dimethylformamide (20 mL) and sodium hydride (60% dispersion in mineral oil, 348 mg, 8.7 mmol) was added carefully (gas evolution). The mixture was stirred at room temperature for 1.5 h. Then, 3-bromo-2-methylprop-1-ene (2.14 g, 15.4 mmol) was added and the resulting mixture was stirred for 16 h at 40° C. After that, water (20 mL) was added, the mixture was extracted with methyltertbutyl ether (2×100 mL), the organic phases were washed with water (3×20 mL) and brine (20 mL), combined, dried (sodium sulfate), and concentrated in vacuo. The crude product was purified by column chromatography (silica gel, 120 g, eluting with ethyl acetate/n-heptane, gradient 0:100 to 5:95) to afford the title compound as a yellow oil (1.55 g, 61%). HPLC (method LCMS_fastgradient) $t_R$=1.65 min. $^1$H NMR (CDCl$_3$, 300 MHz): δ 1.79 (s, 3H), 4.56 (s, 2H), 4.80-4.83 (m, 1H), 4.87-4.90 (m, 1H), 6.82-6.95 (m, 2H), 7.14-7.23 (m, 1H). MS (ES+) m/z 408.0, 410.0, 412.0 [M+H, Br & 2 Cl isotopes].

Step 3: 5-Bromo-2-chloro-N4-(2,4-difluorophenyl)-N6-methyl-N4-(2-methylallyl)-pyrimidine-4,6-diamine (Int-12)

5-Bromo-2,6-dichloro-N-(2,4-difluorophenyl)-N-(2-methylallyl)pyrimidin-4-amine (Int-11, 1.54 g, 3.76 mmol) was dissolved in tetrahydrofuran (7.5 mL) and a solution of methylamine in tetrahydrofuran (2.0 M, 6.5 mL, 13.0 mmol) was added dropwise. The mixture was stirred at room temperature for 45 min. After that, water (10 mL) was added, the mixture was extracted with ethyl acetate (2×90 mL), the organic layers were washed with brine (10 mL), combined, dried (sodium sulfate) and concentrated in vacuo. The crude product was purified by column chromatography (silica gel, 80 g, eluting with ethyl acetate/n-heptane, gradient 0:100 to 10:90) to obtain the title compound as a colorless oil (717 mg, 47%). HPLC (method LCMS_fastgradient) $t_R$=1.54 min. $^1$H NMR (CDCl$_3$, 300 MHz): δ 1.78 (s, 3H), 3.03 (d, J=4.8 Hz, 3H), 4.47 (s, 2H), 4.82-4.86 (m, 2H), 5.43-5.53 (m, 1H), 6.77-6.87 (m, 2H), 7.07-7.17 (m, 1H). MS (ES+) m/z 403.0, 404.8, 406.9 [M+H, Br & Cl isotopes].

Step 4: 2-Chloro-7-(2,4-difluorophenyl)-N,5,5-trimethyl-6,7-dihydro-5H-pyrrolo[2,3-d]pyrimidin-4-amine (Int-13)

5-Bromo-2-chloro-N4-(2,4-difluorophenyl)-N6-methyl-N4-(2-methylallyl)pyrimidine-4,6-diamine (Int-12, 710 mg, 1.76 mmol), sodium formate (127 mg, 1.86 mmol), tetrabutylammonium chloride (500 mg, 1.80 mmol) and palladium (II) acetate (90 mg, 401 μmol) were charged under argon in a 25 mL round bottomed flask. Dimethylformamide (5.4 mL), followed by triethylamine (457 mg, 4.52 mmol) were added and the flask was evacuated carefully and backfilled with argon. The resulting mixture was stirred at 80° C. for 18 h. After cooling, water (10 mL) was added, the mixture was extracted with methyltertbutyl ether (2×80 mL), the organic layers were washed with water (3×10 mL) and brine (1×10 mL), combined, dried (sodium sulfate) and concentrated in vacuo. The crude product was purified by column chromatography (silica gel, 25 g, eluting with ethyl acetate/n-heptane, gradient 0:100 to 20:80) to yield the title compound as a light yellow solid (491 mg, 86%). HPLC (method LCMS_fastgradient) $t_R$=1.32 min. $^1$H NMR (CDCl$_3$, 300 MHz): δ 1.41 (s, 6H), 3.07 (d, J=4.8 Hz, 3H), 3.67 (d, J=0.8 Hz, 2H), 4.26-4.37 (m, 1H), 6.83-6.94 (m, 2H), 7.45-7.55 (m, 1H). MS (ES+) m/z 325.0, 327.0 [M+H, Cl isotopes].

Int-17: 2-Chloro-7-(3,3-difluorocyclobutyl)-N,5,5-trimethyl-6,7-dihydro-5H-pyrrolo[2,3-d]pyrimidin-4-amine

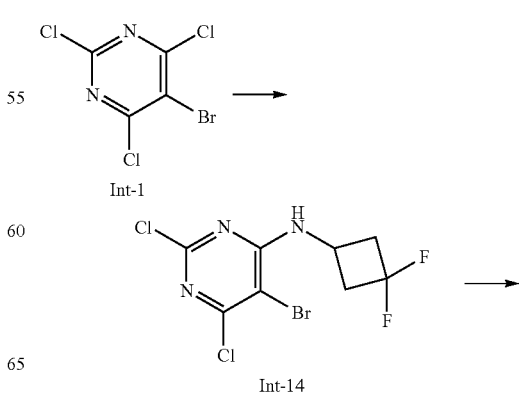

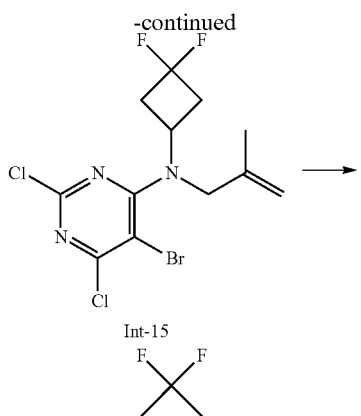

Int-15

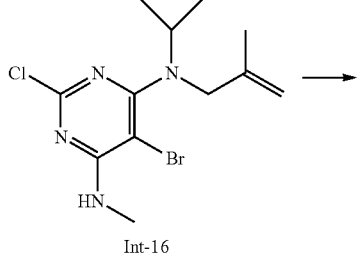

Int-16

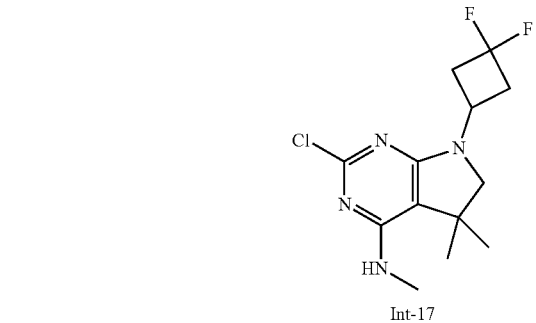

Int-17

Step 1: 5-Bromo-2,6-dichloro-N-(3,3-difluorocyclobutyl)pyrimidin-4-amine (Int-14)

5-Bromo-2,4,6-trichloropyrimidine (1.28 g, 4.88 mmol) and 3,3-difluorocyclobutan-amine hydrochloride (715 mg, 4.98 mmol) were suspended in acetonitrile (6 mL) and N,N-diisopropylethylamine (1.55 g, 2.1 mL, 12 mmol) was added at room temperature. The resulting yellow solution was stirred for 7 h at room temperature. After that, the reaction mixture was concentrated in vacuo and the residue was purified by column chromatography (silica gel, 80 g, eluting with ethyl acetate/n-heptane, gradient 0:100 to 10:90) to yield, after drying in vacuo (40° C., 5 mbar), the title compound as a pale yellow oil (1.188 g, 73%). HPLC (method LCMS_fastgradient) $t_R$=1.31 min. $^1$H NMR (CDCl$_3$, 300 MHz): δ 2.48-2.67 (m, 2H), 3.08-3.25 (m, 2H), 4.39-4.53 (m, 1H), 5.78-5.90 (m, 1H). MS (ES+) m/z 330.0, 332.0, 334.0 [M+H, Br & 2 Cl isotopes].

Step 2: 5-Bromo-2,6-dichloro-N-(3,3-difluorocyclobutyl)-N-(2-methylallyl)pyrimidin-4-amine (Int-15)

5-Bromo-2,6-dichloro-N-(3,3-difluorocyclobutyl)pyrimidin-4-amine (Int-14, 1.18 g, 3.54 mmol) was dissolved in dimethylformamide (12 mL) and sodium hydride (60% dispersion in mineral oil, 198 mg, 4.96 mmol) was added carefully (gas evolution). The mixture was stirred at room temperature for 1 h. Then, 3-bromo-2-methylprop-1-ene (844 mg, 6.06 mmol) was added and the resulting mixture was stirred for 18 h at room temperature. After that, water (15 mL) was added, the mixture was extracted with methyltertbutyl ether (2×100 mL), the organic phases were washed with water (3×15 mL) and brine (15 mL), combined, dried (sodium sulfate), and concentrated in vacuo. The crude product was purified by column chromatography (silica gel, 40 g, eluting with ethyl acetate/n-heptane, gradient 0:100 to 5:95) to give the title compound as colorless oil (965 mg, 70%). HPLC (method LCMS_fastgradient) $t_R$=1.55 min. $^1$H NMR (CDCl$_3$, 300 MHz): δ 1.61 (s, 3H), 2.45-2.67 (m, 2H), 2.89-3.07 (m, 2H), 4.19 (s, 2H), 4.21-4.35 (m, 1H), 4.82-4.86 (m, 1H), 4.94-4.98 (m, 1H). MS (ES+) m/z 385.9, 387.9, 389.8 [M+H, Br & 2 Cl isotopes].

Step 3: 5-Bromo-2-chloro-N4-(3,3-difluorocyclobutyl)-N6-methyl-N4-(2-methylallyl)-pyrimidine-4,6-diamine (Int-16)

5-Bromo-2,6-dichloro-N-(3,3-difluorocyclobutyl)-N-(2-methylallyl)pyrimidin-4-amine (Int-15, 0.960 g, 2.48 mmol) was dissolved in tetrahydrofuran (6 mL) and a solution of methylamine in tetrahydrofuran (2.0 M, 2.0 mL, 4.0 mmol) was added dropwise. The mixture was stirred at room temperature for 1.5 h. After that, water (10 mL) was added, the mixture was extracted with ethyl acetate (2×90 mL), the organic phases were washed with brine (10 mL), combined, dried (sodium sulfate), and concentrated in vacuo. The crude product was purified by column chromatography (silica gel, 40 g, eluting with ethyl acetate/n-heptane, gradient 0:100 to 10:90) to yield the title compound as an off-white solid (311 mg, 33%). HPLC (method LCMS_fastgradient) $t_R$=1.49 min. $^1$H NMR (CDCl$_3$, 300 MHz): δ 1.60 (s, 3H), 2.44-2.55 (m, 2H), 2.85-2.95 (m, 2H), 3.05 (d, J=4.8 Hz, 3H), 4.00 (s, 2H), 4.09-4.17 (m, 1H), 4.85 (br s, 1H), 4.88 (br s, 1H), 5.52-5.57 (m, 1H). MS (ES+) m/z 381.0, 382.9, 384.9 [M+H, Br & Cl isotopes].

Step 4: 2-Chloro-7-(3,3-difluorocyclobutyl)-N,5,5-trimethyl-6,7-dihydro-5H-pyrrolo[2,3-d]pyrimidin-4-amine (Int-17)

5-Bromo-2-chloro-N4-(3,3-difluorocyclobutyl)-N6-methyl-N4-(2-methylallyl)pyrimidine-4,6-diamine (Int-16, 300 mg, 0.786 mmol), sodium formate (57 mg, 0.838 mmol), tetrabutylammonium chloride (223 mg, 0.802 mmol) and palladium (II) acetate (39 mg, 0.174 mmol) were charged under argon in a 25 mL round bottomed flask. Dimethylformamide (2.4 mL), followed by triethylamine (203 mg, 2.01 mmol) were added and the flask was evacuated carefully and backfilled with argon. The resulting mixture was stirred at 80° C. for 18 h. After cooling, water (5 mL) was added, the mixture was extracted with methyltertbutyl ether (2×70 mL), the organic phases were washed with water (3×5 mL) and brine (5 mL), combined, dried (sodium sulfate), and concentrated in vacuo. The crude product was purified by column chromatography (silica gel, 25 g, eluting with ethyl acetate/n-heptane, gradient 0:100 to 30:70) to afford the title compound as a yellow solid (204 mg, 86%). HPLC (method LCMS_fastgradient) $t_R$=1.26 min. $^1$H NMR (CDCl$_3$, 300 MHz): δ 1.34 (s, 6H), 2.67-2.95 (m, 4H), 3.02 (d, J=4.8 Hz, 3H), 3.26 (s, 2H), 4.11-4.21 (m, 1H), 4.52-4.67 (m, 1H). MS (ES+) m/z 303.1, 305.0 [M+H, Cl isotopes].

Int-21: 2-Chloro-N,5,5-trimethyl-7-(3-(trifluoromethyl)bicyclo[1.1.1]pentan-1-yl)-6,7-dihydro-5H-pyrrolo[2,3-d]pyrimidin-4-amine

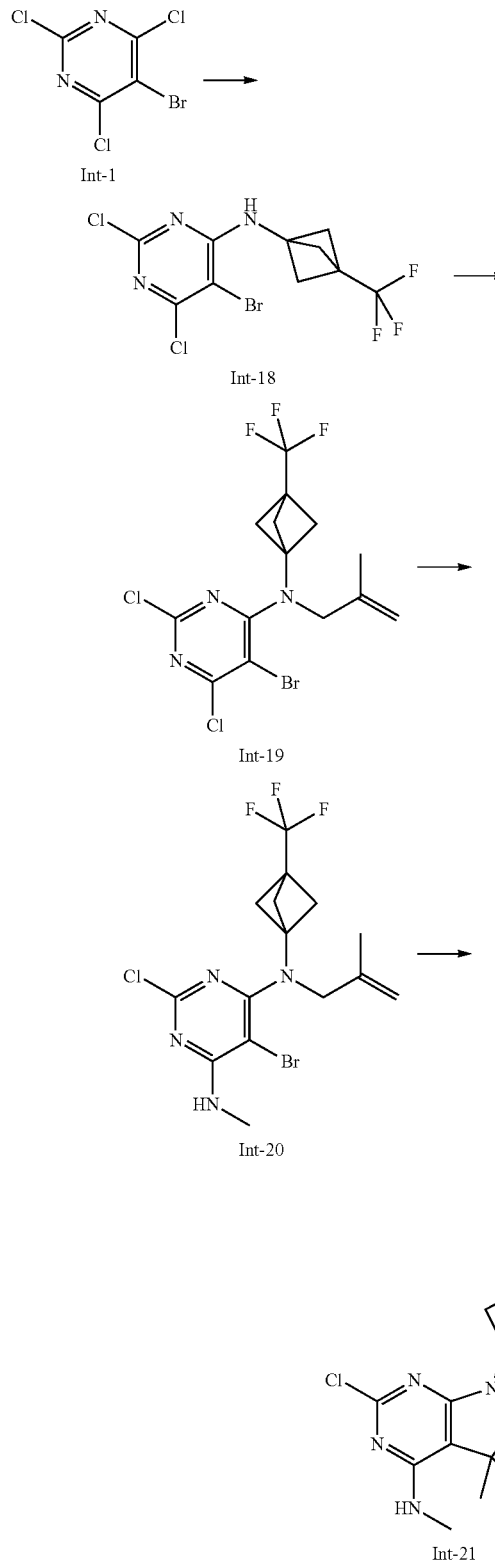

Step 1: 5-Bromo-2,6-dichloro-N-(3-(trifluoromethyl)bicyclo[1.1.1]pentan-1-yl)pyrimidin-4-amine (Int-18)

5-Bromo-2,4,6-trichloropyrimidine (1.30 g, 4.96 mmol) and 3-(trifluoromethyl)-bicyclo[1.1.1]pentan-1-amine hydrochloride (985 mg, 4.99 mmol) were suspended in acetonitrile (6.5 mL) and N,N-diisopropylethylamine (1.55 g, 2.1 mL, 12 mmol) was added at room temperature. The resulting yellow solution was stirred for 7 h at room temperature. After that, the reaction mixture was concentrated in vacuo and the residue was purified by column chromatography (silica gel, 80 g, eluting with ethyl acetate/n-heptane, gradient 0:100 to 10:90) to yield, after drying in vacuo (40° C., 5 mbar), the title compound as an off-white solid (1.487 g, 80%). HPLC (method LCMS_fastgradient) $t_R$=1.50 min. $^1$H NMR (CDCl$_3$, 300 MHz): δ 2.46 (s, 6H), 6.10 (br s, 1H). MS (ES+) m/z 375.9, 377.9, 379.8 [M+H, Br & 2 Cl isotopes].

Step 2: 5-Bromo-2,6-dichloro-N-(2-methylallyl)-N-(3-(trifluoromethyl)bicyclo[1.1.1]-pentan-1-yl)pyrimidin-4-amine (Int-19)

5-Bromo-2,6-dichloro-N-(3-(trifluoromethyl)bicyclo[1.1.1]pentan-1-yl)pyrimidin-4-amine (Int-18, 1.48 g, 3.93 mmol) was dissolved in dimethylformamide (13 mL) and sodium hydride (60% dispersion in mineral oil, 220 mg, 5.50 mmol) was added carefully (gas evolution). The mixture was stirred at room temperature for 1.5 h. Then, 3-bromo-2-methylprop-1-ene (937 mg, 6.73 mmol) was added and the resulting mixture was stirred for 5 h at room temperature, followed by 14 h at 40° C. After that, water (15 mL) was added, the mixture was extracted with methyltertbutyl ether (2×100 mL), the organic phases were washed with water (3×15 mL) and brine (15 mL), combined, dried (sodium sulfate), and concentrated in vacuo. The crude product was purified by column chromatography (silica gel, 80 g, eluting with ethyl acetate/n-heptane, gradient 0:100 to 5:95) to yield the title compound as colorless oil (1.372 g, 73%). HPLC (method LCMS_fastgradient) $t_R$=1.77 min. $^1$H NMR (CDCl$_3$, 300 MHz): δ 1.68 (s, 3H), 2.45 (s, 6H), 4.25 (s, 2H), 4.85-4.91 (m, 1H), 4.97-5.02 (m, 1H). MS (ES+) m/z 430.0, 432.0, 434.0 [M+H, Br & 2 Cl isotopes].

Step 3: 5-Bromo-2-chloro-N4-methyl-N6-(2-methylallyl)-N6-(3-(trifluoromethyl)bicyclo[1.1.1]pentan-1-yl)pyrimidine-4,6-diamine (Int-20)

5-Bromo-2,6-dichloro-N-(2-methylallyl)-N-(3-(trifluoromethyl)bicyclo[1.1.1]pentan-1-yl)pyrimidin-4-amine (Int-19, 1.37 g, 2.86 mmol) was dissolved in tetrahydrofuran (7.0 mL) and a solution of methylamine in tetrahydrofuran (2.0 M, 3.5 mL, 7.0 mmol) was added dropwise. The mixture was stirred at room temperature for 1.5 h. After that, water (10 mL) was added, the mixture was extracted with ethyl acetate (2×90 mL), the organic phases were washed with brine (10 mL), combined, dried (sodium sulfate), and concentrated in vacuo. The crude product was purified by column chromatography (silica gel, 40 g, eluting with ethyl acetate/n-heptane, gradient 0:100 to 10:90) to afford the title compound as a mixture of regioisomers (ratio ca. 2.7:1 by $^1$H nmr) and as an off-white solid (1.179 g, 97%). The isolated mixture was used in the next step without further purification. Major regioisomer (title compound): HPLC (method LCMS_fastgradient) $t_R$=1.69 min. MS (ES+) m/z 425.1, 427.1, 429.0 [M+H, Br & Cl isotopes]. Minor regioisomer (5-bromo-6-chloro-N2-methyl-N4-(2-methylallyl)-N4-(3-(trifluoromethyl)-bicyclo[1.1.1]pentan-1-yl)pyrimidine-2,4-diamine): HPLC (method LCMS_fastgradient) $t_R$=1.71 min. MS (ES+) m/z 425.1, 427.1, 429.0 [M+H, Br & Cl isotopes].

Step 4: 2-Chloro-N,5,5-trimethyl-7-(3-(trifluoromethyl)bicyclo[1.1.1]pentan-1-yl)-6,7-dihydro-5H-pyrrolo[2,3-d]pyrimidin-4-amine (Int-21)

5-Bromo-2-chloro-N4-methyl-N6-(2-methylallyl)-N6-(3-(trifluoromethyl)bicyclo[1.1.1]-pentan-1-yl)pyrimidine-4,6-diamine (Int-20, ca. 2.7:1 mixture of regioisomers, 1.17 g, 2.75 mmol), sodium formate (200 mg, 2.94 mmol), tetrabutylammonium chloride (779 mg, 2.80 mmol) and palladium (II) acetate (136 mg, 0.605 mmol) were charged under argon in a 50 mL round bottomed flask. Dimethylformamide (8.5 mL), followed by triethylamine (726 mg, 7.17 mmol) were added and the flask was evacuated carefully and backfilled with argon. The resulting mixture was stirred at 80° C. for 18 h. After cooling, water (10 mL) was added, the mixture was extracted with methyltertbutyl ether (2×90 mL), the organic phases were washed with water (3×10 mL) and brine (10 mL), combined, dried (sodium sulfate), and concentrated in vacuo. The crude product was purified by column chromatography (silica gel, 40 g, eluting with ethyl acetate/n-heptane, gradient 0:100 to 20:80) to afford the title compound as a yellow solid (584 mg, 61%). HPLC (method LCMS_fastgradient) $t_R$=1.53 min. $^1$H NMR (CDCl$_3$, 300 MHz): δ 1.32 (s, 6H), 2.34 (s, 6H), 3.02 (d, J=4.8 Hz, 3H), 3.17 (s, 2H), 4.11-4.22 (m, 1H). MS (ES+) m/z 347.0, 349.0 [M+H, Cl isotopes].

Int-23: 2-((2-Chloro-7-(4-fluorophenyl)-5,5-dimethyl-6,7-dihydro-5H-pyrrolo[2,3-d]pyrimidin-4-yl)amino)ethanol

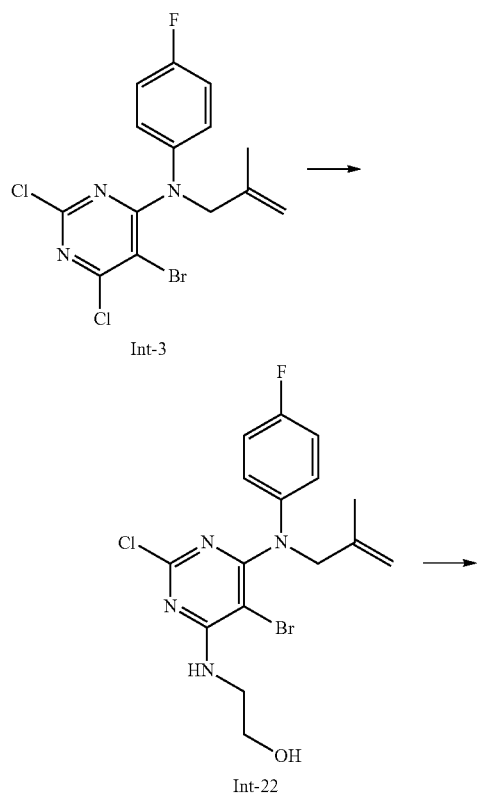

Int-3

Int-22

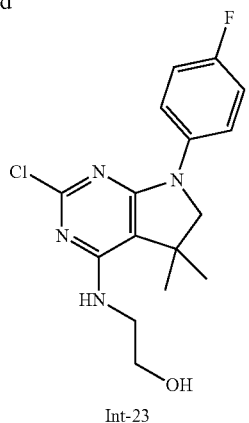

Int-23

Step 1: 2-((5-Bromo-2-chloro-6-((4-fluorophenyl)(2-methylallyl)amino)pyrimidin-4-yl)amino)ethanol (Int-22)

5-Bromo-2,6-dichloro-N-(3,4-difluorophenyl)-N-(2-methylallyl)pyrimidin-4-amine (Int-3, 1.30 g, 3.32 mmol) was dissolved in tetrahydrofuran (4 mL) and a solution of 2-aminoethanol (772 mg, 12.6 mmol) in tetrahydrofuran (4.3 mL) was added dropwise. The mixture was stirred at room temperature for 3.5 h. After that, water (10 mL) was added, the mixture was extracted with ethyl acetate (2×100 mL), the organic layers were washed with brine (10 mL), combined, dried (sodium sulfate) and concentrated in vacuo. The crude product was purified by column chromatography (silica gel, 80 g, eluting with ethyl acetate/n-heptane, gradient 0:100 to 30:70) to afford the title compound as a white solid (684 mg, 49%). HPLC (method LCMS_fastgradient) $t_R$=1.41 min. $^1$H NMR (CDCl$_3$, 300 MHz): δ 1.78 (s, 3H), 2.59 (s, 1H), 3.64-3.68 (m, 2H), 3.83 (t, J=4.9 Hz, 2H), 4.52 (s, 2H), 4.86-4.89 (m, 1H), 4.92 (s, 1H), 5.90 (t, J=5.0 Hz, 1H), 6.95-7.03 (m, 4H). MS (ES+) m/z 415.1, 417.1, 419.1 [M+H, Br & Cl isotopes].

Step 2: 2-((2-Chloro-7-(4-fluorophenyl)-5,5-dimethyl-6,7-dihydro-5H-pyrrolo[2,3-d]pyrimidin-4-yl)amino)ethanol (Int-23)

2-((5-Bromo-2-chloro-6-((4-fluorophenyl)(2-methylallyl)amino)pyrimidin-4-yl)amino)-ethanol (Int-22, 670 mg, 1.61 mmol), sodium formate (115 mg, 1.69 mmol), tetrabutylammonium chloride (457 mg, 1.64 mmol) and palladium (II) acetate (84 mg, 374 µmol) were charged under argon in a 50 mL round bottomed flask. Dimethylformamide (5 mL), followed by triethylamine (414 mg, 4.09 mmol) were added and the flask was evacuated carefully and backfilled with argon. The resulting mixture was stirred at 80° C. for 18 h. After cooling, water (5 mL) was added, the mixture was extracted with methyltertbutyl ether (2×100 mL), the organic layers were washed with water (3×5 mL) and brine (1×5 mL), combined, dried (sodium sulfate) and concentrated in vacuo. The crude product was purified by column chromatography (silica gel, 25 g, eluting with ethyl acetate/n-heptane, gradient 0:100 to 60:40) to afford the title compound as a brown solid (393 mg, 72%). HPLC (method LCMS_fastgradient) $t_R$=1.27 min. $^1$H NMR (CDCl$_3$, 300 MHz): δ 1.44 (s, 6H), 2.95 (t, J=4.9 Hz, 1H), 3.64-3.71 (m, 2H), 3.73 (s, 2H), 3.81-3.87 (m, 2H), 4.81 (t, J=5.3 Hz, 1H), 7.06 (dd, J=8.4, 9.4 Hz, 2H), 7.54-7.62 (m, 2H). MS (ES+) m/z 337.2, 339.2 [M+H, Cl isotopes].

Int-27: 2-Chloro-8-(4-fluorophenyl)-N,5,5-trimethyl-5,6,7,8-tetrahydropyrido[2,3-d]-pyrimidin-4-amine

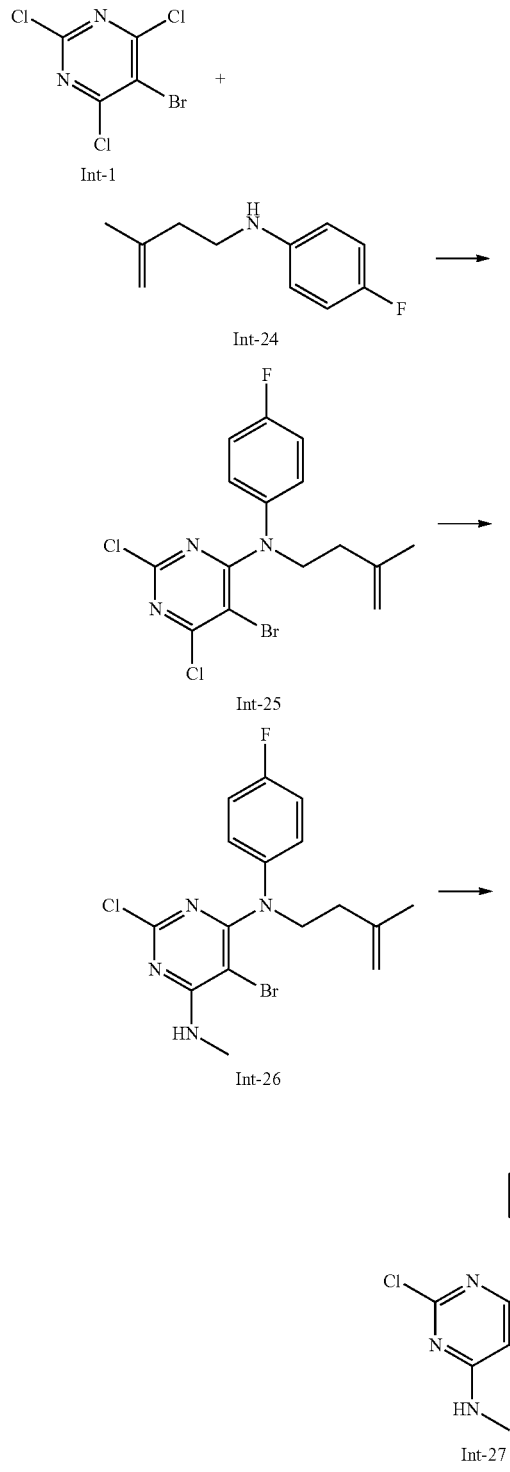

Step 1: 4-Fluoro-N-(3-methylbut-3-en-1-yl)aniline (Int-24)

4-Fluoroaniline (498 mg, 4.48 mmol) and potassium carbonate (1.03 g, 7.46 mmol) were suspended in DMF (9 mL). A solution of 4-bromo-2-methylbut-1-ene (556 mg, 3.73 mmol) in DMF (2 mL) was added dropwise and the reaction mixture was stirred at 80° C. for 18 h. After cooling to room temperature, water (10 mL) was added and the resulting mixture was extracted with tertbutylmethyl ether (2×80 mL), the organic layers were washed with water (3×10 mL) and brine (1×10 mL), combined, dried (sodium sulfate) and concentrated in vacuo. The crude product was purified by column chromatography (silica gel, 25 g, eluting with ethyl acetate/n-heptane, gradient 0:100 to 5:95) to afford the title compound as a yellow oil (384 mg, 57%). HPLC (method LCMS_fastgradient) $t_R$=1.15 min. $^1$H NMR (CDCl$_3$, 300 MHz): δ 1.77 (s, 3H), 2.31-2.39 (m, 2H), 3.13-3.23 (m, 2H), 3.53 (br s, 1H), 4.77-4.82 (m, 1H), 4.85-4.89 (m, 1H), 6.51-6.59 (m, 2H), 6.85-6.94 (m, 2H). MS (ES+) m/z 180.1 [M+H].

Step 2: 5-Bromo-2,6-dichloro-N-(4-fluorophenyl)-N-(3-methylbut-3-en-1-yl)pyrimidin-4-amine (Int-25)

4-Fluoro-N-(3-methylbut-3-en-1-yl)aniline (Int-24, 382 mg, 2.13 mmol) was dissolved in THF (4 mL) and water (2 mL), and sodium acetate (525 mg, 6.39 mmol), followed by 5-bromo-2,4,6-trichloropyrimidine (589 mg, 2.13 mmol) were added. The mixture was stirred at room temperature for 18 h. After that, a saturated aqueous solution of sodium hydrogencarbonate (10 mL) was added and the resulting mixture was extracted with ethyl acetate (2×80 mL). The combined organic layers were dried (sodium sulfate) and concentrated in vacuo. The crude was purified by column chromatography (silica gel, 40 g, eluting with ethyl acetate/n-heptane, gradient 0:100 to 5:95) to yield, after drying in vacuo (40° C., 5 mbar), the title compound as a yellow solid (527 mg, 61%). HPLC (method LCMS_fastgradient) $t_R$=1.70 min. $^1$H NMR (CDCl$_3$, 300 MHz): δ 1.79 (s, 3H), 2.32-2.40 (m, 2H), 4.01-4.08 (m, 2H), 4.67-4.71 (m, 1H), 4.78-4.82 (m, 1H), 7.06-7.11 (m, 4H). MS (ES+) m/z 404.1, 406.1, 408.1 [M+H, Br & 2 Cl isotopes].

Step 3: 5-Bromo-2-chloro-N4-(4-fluorophenyl)-N6-methyl-N4-(3-methylbut-3-en-1-yl)pyrimidine-4,6-diamine (Int-26)

5-Bromo-2,6-dichloro-N-(4-fluorophenyl)-N-(3-methylbut-3-en-1-yl)pyrimidin-4-amine (Int-25, 519 mg, 1.28 mmol) was dissolved in tetrahydrofuran (3 mL), the solution was cooled to 0-5° C. (ice bath) and a solution of methylamine in tetrahydrofuran (2.0 M, 2.4 mL, 4.8 mmol) was added dropwise. The mixture was stirred at 0-5° C. for 1 h, followed by 1 h at room temperature. After that, water (5 mL) was added, the mixture was extracted with ethyl acetate (2×40 mL), the organic layers were washed with brine (1×5 mL), combined, dried (sodium sulfate) and concentrated in vacuo. The crude product was purified by column chromatography (silica gel, 25 g, eluting with ethyl acetate/n-heptane, gradient 0:100 to 5:95) to afford the title compound as an off-white solid (274 mg, 53%). HPLC (method LCMS_ fastgradient) $t_R$=1.64 min. $^1$H NMR (CDCl$_3$, 300 MHz): δ 1.79 (s, 3H), 2.31-2.39 (m, 2H), 3.03 (d, J=4.8 Hz, 3H), 3.93-4.01 (m, 2H), 4.66-4.70 (m, 1H), 4.75-4.78 (m, 1H), 5.40-5.50 (m, 1H), 6.99-7.04 (m, 4H). MS (ES+) m/z 399.1, 401.1, 403.1 [M+H, Br & Cl isotopes].

Step 4: 2-Chloro-8-(4-fluorophenyl)-N,5,5-trimethyl-5,6,7,8-tetrahydropyrido[2,3-d]pyrimidin-4-amine (Int-27)

5-Bromo-2-chloro-N4-(4-fluorophenyl)-N6-methyl-N4-(3-methylbut-3-en-1-yl)pyrimidine-4,6-diamine (Int-26, 270 mg, 676 µmol), sodium formate (51 mg, 750 µmol), tetrabutylammonium chloride (188 mg, 676 µmol) and palladium (II) acetate (76 mg, 339 µmol) were charged under argon in a 25 mL round bottomed flask. Dimethylformamide (1.7 mL), followed by triethylamine (182 mg, 1.79 mmol) were added and the flask was evacuated carefully and backfilled with argon. The resulting mixture was stirred at 110° C. for 18 h. After cooling, water (5 mL) was added, the mixture was extracted with a mixture of methyltertbutyl ether/ethyl acetate (1:1 v/v, 2×40 mL), the organic layers were washed with water (3×5 mL) and brine (1×5 mL), combined, dried (sodium sulfate) and concentrated in vacuo. The crude product was purified by column chromatography (silica gel, 12 g, eluting with ethyl acetate/n-heptane, gradient 0:100 to 20:80) to yield the title compound as an off-white solid (104 mg, 48%). HPLC (method LCMS_fast-gradient) $t_R$=1.39 min. $^1$H NMR (CDCl$_3$, 300 MHz): δ 1.40 (s, 6H), 1.87-1.93 (m, 2H), 3.05 (d, J=4.6 Hz, 3H), 3.58-3.64 (m, 2H), 4.60-4.69 (m, 1H), 7.00-7.08 (m, 2H), 7.16-7.22 (m, 2H). MS (ES+) m/z 321.2, 323.2 [M+H, Cl isotopes].

Int-30: 2,4-Dichloro-7-(4-fluorophenyl)-6,7-dihydro-5H-pyrrolo[2,3-d]pyrimidine

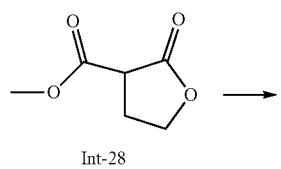

Int-28

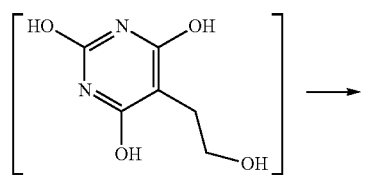

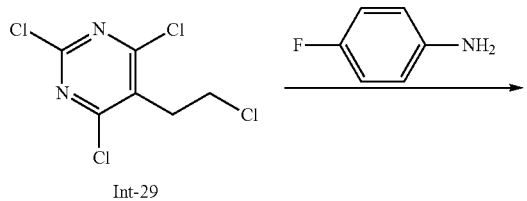

Int-29

Int-30

Step 1: 2,4,6-Trichloro-5-(2-chloroethyl)pyrimidine (Int-29)

Methyl 2-oxotetrahydrofuran-3-carboxylate (Int-28, 5.20 g, 36.1 mmol) was dissolved in ethanol (40 mL) and urea (2.17 g, 36.1 mmol) was added, followed by a solution of sodium ethoxide in ethanol (21% m/m, 24.3 g, 28 mL, 75 mmol). The resulting suspension was stirred at 75° C. for 18 h. After that, it was cooled to room temperature and concentrated in vacuo. The residue, a light brown solid (8.87 g), was added carefully in small portions to precooled (0-5° C., ice bath) phosphorus oxychloride (57.6 g, 35 mL). Strong fuming was observed. After that, N,N-dimethylaniline (5.74 g, 47.3 mmol) was added and the reaction mixture was stirred at 100° C. for 18 h. Then, it was cooled to room temperature, poured into ice water (480 g) and stirred for 1 h, until the ice was melted. The formed precipitate was filtered off, washed with water and dried in vacuo to afford the title compound as a dark brown solid (3.8 g, 43%), that was used without further purification in the next step. $^1$H NMR (DMSO-d6, 300 MHz): δ 3.31 (t, J=7.2 Hz, 2H), 3.86 (t, J=7.2 Hz, 2H).

Step 2: 2,4-Dichloro-7-(4-fluorophenyl)-6,7-dihydro-5H-pyrrolo[2,3-d]pyrimidine (Int-30)

2,4,6-Trichloro-5-(2-chloroethyl)pyrimidine (Int-29, 1.84 g, 7.48 mmol) was dissolved in acetonitrile (40 mL), and 4-fluoroaniline (833 mg, 7.5 mmol), followed by N,N-diisopropylethylamine (2.0 g, 2.7 mL, 15.5 mmol) were added dropwise. The mixture was stirred at room temperature for 7 h and at 50° C. for 18 h. Then, it was concentrated in vacuo and the resulting crude product was purified directly by column chromatography (silica gel, 80 g, eluting with dichloromethane/n-heptane, gradient 0:100 to 80:20) to give a yellow solid, which was further triturated with a mixture of ethyl acetate/n-heptane (1:4, v/v) to afford, after filtration and drying in vacuo, the title compound as an off-white solid (893 mg, 42%). HPLC (method LCMS_fast-gradient) $t_R$=1.37 min. $^1$H NMR (CDCl$_3$, 300 MHz): δ 3.19 (dd, J=8.3, 9.1 Hz, 2H), 4.20 (dd, J=8.3, 9.1 Hz, 2H), 7.12 (dd, J=8.1, 9.3 Hz, 2H), 7.67 (dd, J=4.6, 9.3 Hz, 2H). MS (ES+) m/z 284.1, 286.0 [M+H, 2 Cl isotopes].

Int-34: 2,4-Dichloro-7-(4-fluorophenyl)-5-methyl-6,7-dihydro-H-pyrrolo[2,3-d]pyrimidine

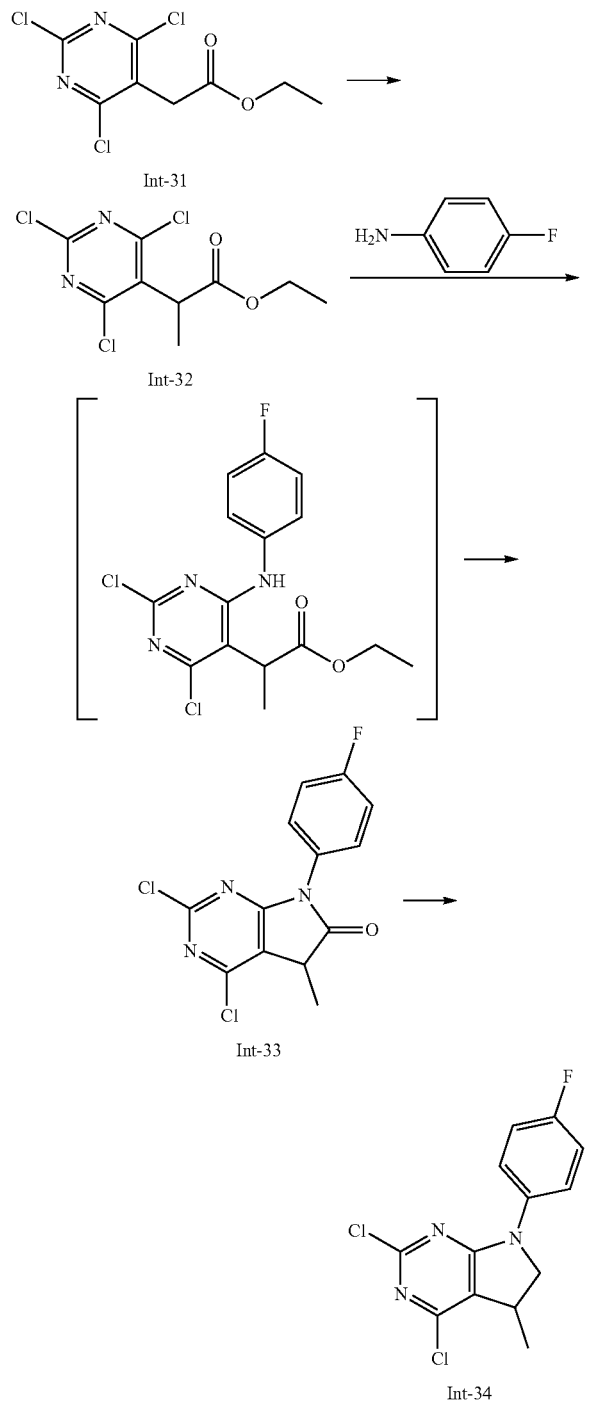

Step 1: Ethyl 2-(2,4,6-trichloropyrimidin-5-yl)propanoate (Int-32)

Ethyl 2-(2,4,6-trichloropyrimidin-5-yl)acetate (Int-31, prepared as described in WO20120928800, 3.3 g, 12.2 mmol) was dissolved in dry tetrahydrofuran (75 mL) and the solution was cooled to −76° C. (dry ice/acetone bath). A solution of lithium hexamethyldisilazide in tetrahydrofuran/ethylbenzene (1M, 12.2 mL, 12.2 mmol) was added over 10 min, and the resulting orange solution was stirred at −76° C. for 45 min. Then, a solution of iodomethane (2.09 g, 14.7 mmol) in dry tetrahydrofuran (6 mL) was added over 15 min at that temperature. The resulting mixture was stirred for 3 h at −23 to −16° C. (ice/ethanol bath). After that, a saturated aqueous solution of ammonium chloride (80 mL), followed by water (100 mL) was added, the resulting mixture was extracted with ethyl acetate (2×80 mL), the combined organic layers were washed with semi-saturated brine (1×100 mL), dried (sodium sulfate) and concentrated in vacuo. The crude product was purified by column chromatography (silica gel, 80 g, eluting with ethyl acetate/n-heptane, gradient 1:99 to 2:98) to afford the title compound as a colorless oil (2.88 g, 82%). HPLC (method LCMS_fastgradient) $t_R$=1.32 min. $^1$H NMR (CDCl$_3$, 300 MHz): δ 1.24 (t, J=7.1 Hz, 3H), 1.56 (d, J=7.2 Hz, 3H), 4.16-4.27 (m, 2H), 4.34 (q, J=7.2 Hz, 1H). MS (ES+) m/z 283.0, 285.0, 287.0 [M+H, 3 Cl isotopes].

Step 2: 2,4-Dichloro-7-(4-fluorophenyl)-5-methyl-5H-pyrrolo[2,3-d]pyrimidin-6(7H)-one (Int-33)

Ethyl 2-(2,4,6-trichloropyrimidin-5-yl)propanoate (Int-32, 8.9 g, 31.4 mmol) was dissolved in tetrahydrofuran (70 mL) and 4-fluoroaniline (3.84 g, 34.5 mmol) was added, followed by a solution of diisopropylethylamine (5.27 g, 40.8 mmol) in tetrahydrofuran (10 mL). The resulting solution was stirred for 4 h at 66° C. (reflux). After cooling, the solvent was distilled off and the crude product directly purified by column chromatography (silica gel, 220 g, eluting with ethyl acetate/n-heptane, gradient 1:99 to 15:85) to yield, after trituration with diethyl ether/n-heptane (1:4 v/v, 50 mL) and drying in vacuo (40° C., 5 mbar), the title compound as a yellow solid (2.1 g, 21%). HPLC (method LCMS_fastgradient) $t_R$=1.27 min. $^1$H NMR (CDCl$_3$, 300 MHz): δ 1.72 (d, J=7.7 Hz, 3H), 3.77 (q, J=7.7 Hz, 1H), 7.23 (dd, J=8.2, 9.2 Hz, 2H), 7.45 (dd, J=4.7, 9.2 Hz, 2H). MS (ES+) m/z 312.0, 314.0 [M+H, 2 Cl isotopes].

Step 3: 2,4-Dichloro-7-(4-fluorophenyl)-5-methyl-6,7-dihydro-5H-pyrrolo[2,3-d]pyrimidine (Int-34)

2,4-Dichloro-7-(4-fluorophenyl)-5-methyl-5H-pyrrolo[2,3-d]pyrimidin-6(7H)-one (Int-33, 1.83 g, 5.86 mmol) was dissolved in dry tetrahydrofuran (75 mL), the solution was cooled to 0-5° C. (ice bath) and a solution of borane-tetrahydrofuran complex in tetrahydrofuran (1.0 M, 14.7 mL, 14.7 mmol) was added over 15 min. The mixture was stirred at 75° C. for 16 h. After cooling to room temperature, methanol (5 mL) was added dropwise, followed by water (40 mL) and a 1M aqueous solution of hydrogen chloride (40 mL). The mixture was stirred for 30 min at room temperature. Then, the pH was adjusted to 6-7 by addition of solid sodium hydrogencarbonate. The aqueous layer was separated and extracted with ethyl acetate (60 mL), the combined organic layers were washed with brine (1×100 mL), dried (sodium sulfate) and concentrated in vacuo. The crude product was purified by column chromatography (silica gel, 80 g, eluting with ethyl acetate/n-heptane, gradient 3:97 to 20:80), followed by a second column chromatography (silica gel, 120 g, eluting with (ethyl acetate/dichloromethane 1:1 (v/v))/n-heptane, gradient 5:95 to 10:90) to afford the title compound as an white solid (471 mg, 27%). HPLC (method LCMS_fastgradient) $t_R$=1.44 min. $^1$H NMR (CDCl$_3$, 300 MHz): δ 1.44-1.51 (m, 3H), 3.48-3.62 (m, 1H), 3.68-3.77 (m, 1H), 4.29-4.39 (m, 1H), 7.08-7.18 (m, 2H), 7.63-7.72 (m, 2H). MS (ES+) m/z 298.0, 300.0 [M+H, 2 Cl isotopes].

Int-36: N2-((1R,5S,8s)-3-Azabicyclo[3.2.1]octan-8-yl)-7-(4-fluorophenyl)-N4,5,5-trimethyl-6,7-dihydro-5H-pyrrolo[2,3-d]pyrimidine-2,4-diamine

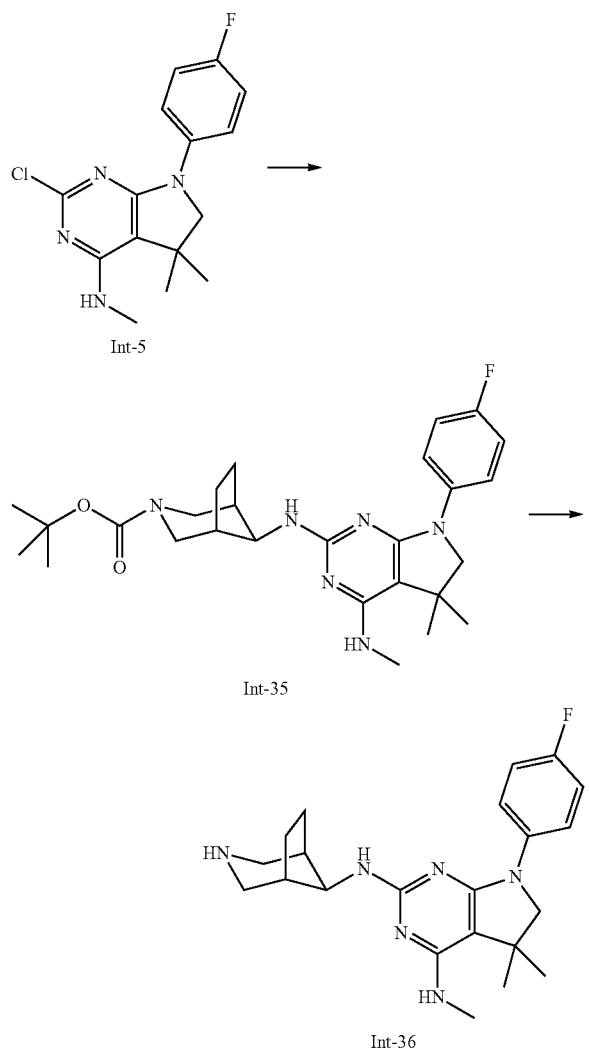

Step 1: (1R,5S,8s)-tert-Butyl 8-((7-(4-fluorophenyl)-5,5-dimethyl-4-(methylamino)-6,7-dihydro-5H-pyrrolo[2,3-d]pyrimidin-2-yl)amino)-3-azabicyclo[3.2.1]octane-3-carboxylate (Int-35)

In an 8 mL microwave vial, 2-chloro-7-(4-fluorophenyl)-N,5,5-trimethyl-6,7-dihydro-5H-pyrrolo[2,3-d]pyrimidin-4-amine (Int-5, 260 mg, 848 µmol) was dissolved in NMP (5.5 mL) and (1R,5S,8s)-tert-butyl 8-amino-3-azabicyclo[3.2.1]octane-3-carboxylate (288 mg, 1.27 mmol), cesium carbonate (552 mg, 1.70 mmol), 2-dicyclohexylphosphino-2'-(N,N-dimethyl-amino)biphenyl (68 mg, 173 µmol), and bis(dibenzylideneacetone)palladium(0) (89 mg, 155 µmol) were added subsequently. The vial was flushed with Argon and sealed. The reaction mixture was heated under microwave irradiation at 150° C. for 30 minutes. After that, water (10 mL) was added and the mixture was extracted with tertbutylmethyl ether (TBME, 2×90 mL). The combined organic layers were washed with water (5×20 mL) and brine (1×20 mL), dried (sodium sulfate) and concentrated in vacuo. The crude product was purified by column chromatography (silica gel, 40 g, eluting with ethyl acetate/n-heptane, gradient 0:100 to 50:50) to afford the title compound as a yellow oil (284 mg, 61%). HPLC (method LCMS_fastgradient) $t_R$=1.09 min. $^1$H NMR (CDCl$_3$, 300 MHz): δ 1.24-1.31 (m, 2H), 1.38 (s, 6H), 1.48 (s, 9H), 1.54-1.64 (m, 2H), 1.82-1.91 (m, 2H), 2.29-2.41 (m, 2H), 3.01 (d, J=4.8 Hz, 3H), 3.60 (s, 2H), 3.85-3.95 (m, 2H), 3.97-4.08 (m, 2H), 4.57 (d, J=5.8 Hz, 1H), 7.01 (dd, J=8.5, 9.3 Hz, 2H), 7.63-7.71 (m, 2H). MS (ES+) m/z 497.6.

Step 2: N2-((1R,5S,8s)-3-Azabicyclo[3.2.1]octan-8-yl)-7-(4-fluorophenyl)-N4,5,5-trimethyl-6,7-dihydro-5H-pyrrolo[2,3-d]pyrimidine-2,4-diamine (Int-36)

(1R,5 S,8s)-tert-Butyl 8-((7-(4-fluorophenyl)-5,5-dimethyl-4-(methylamino)-6,7-dihydro-5H-pyrrolo[2,3-d]pyrimidin-2-yl)amino)-3-azabicyclo[3.2.1]octane-3-carboxylate (Int-35, 280 mg, 564 µmol) was dissolved in dichloromethane (2 mL) and the yellow solution was cooled to 0-5° C. (ice bath). Trifluoroacetic acid (592 mg, 0.4 mL, 5.19 mmol) was carefully added at that temperature and the resulting mixture was allowed to warm to room temperature and stirred for 18 h. After that, it was concentrated in vacuo, the residue was redissolved in dichloromethane (10 mL), basified by careful addition of a saturated aqueous solution of sodium carbonate to pH (ca. 3 mL). It was extracted with dichloromethane (3×30 mL), the combined organic layers were dried (sodium sulfate) and concentrated in vacuo to give the title compound as an orange foam (233 mg, 94%), that was used without further purification in the next step. HPLC (method LCMS_fastgradient) $t_R$=0.71 min. $^1$H NMR (CDCl$_3$, 300 MHz): δ 1.38 (s, 6H), 1.40-1.45 (m, 2H), 1.82-1.93 (m, 2H), 2.01-2.12 (m, 2H), 2.45-2.52 (m, 2H), 3.01 (d, J=4.8 Hz, 3H), 3.13-3.18 (m, 2H), 3.62 (s, 2H), 4.02 (d, J=5.4 Hz, 1H), 4.05-4.13 (m, 1H), 4.56 (br s, 1H), 4.71 (br s, 1H), 7.02 (dd, J=8.4, 9.2 Hz, 2H), 7.59-7.66 (m, 2H). MS (ES+) m/z 397.3.

Int-34p: (−)-2,4-Dichloro-7-(4-fluorophenyl)-5-methyl-6,7-dihydro-5H-pyrrolo[2,3-d]pyrimidine and Int-34q: (+)-2,4-dichloro-7-(4-fluorophenyl)-5-methyl-6,7-dihydro-5H-pyrrolo[2,3-d]pyrimidine

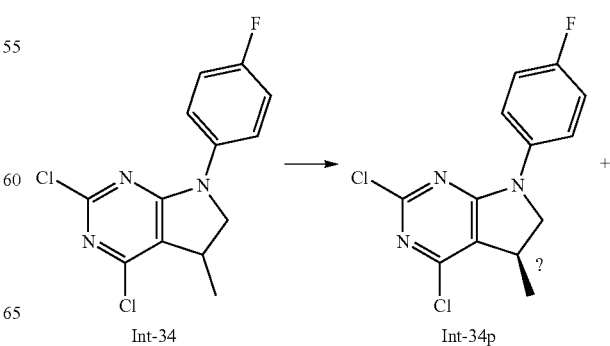

-continued

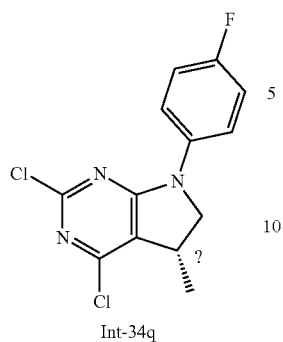

Int-34q

Racemic 2,4-dichloro-7-(4-fluorophenyl)-5-methyl-6,7-dihydro-5H-pyrrolo[2,3-d]pyrimidine (Int-34, 100 mg) was separated in the enantiomers using preparative chiral HPLC (Reprosil Chiral-NR, eluting with n-heptane/2-propanol 80:20 (v/v)) to yield, after concentration of the combined product containing fractions in vacuo, Int-34p as first eluting, (−)-rotating enantiomer (37 mg, 37%), and Int-34q as second eluting, (+)-rotating enantiomer (41 mg, 41%). The stereocenters in the chemical drawing above were assigned arbitrarily to clarify the presence of separated enantiomers. The unambigious enantiomer assignment is Int-34p-(−)-rotating, and Int-34q-(+)-rotating.

Int-38: 2-Chloro-7-(2,3-difluorophenyl)-N,5,5-trimethyl-6,7-dihydro-5H-pyrrolo[2,3-d]pyrimidin-4-amine

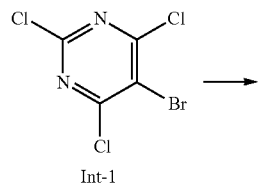

Int-1

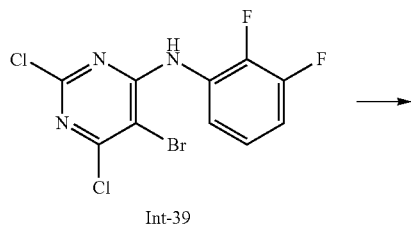

Int-39

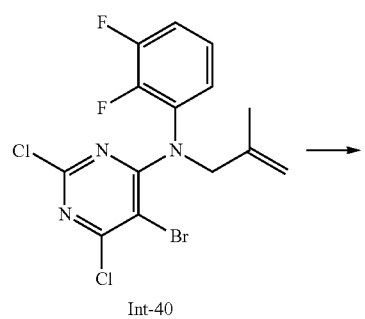

Int-40

-continued

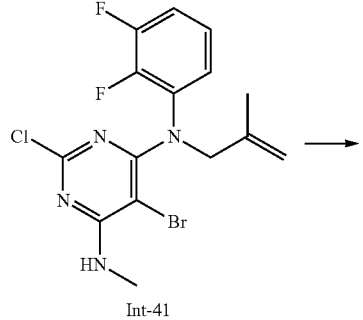

Int-41

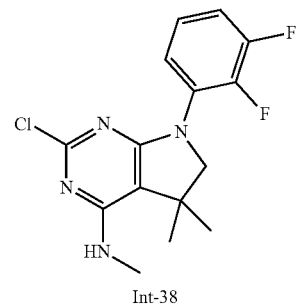

Int-38

Step 1: 5-Bromo-2,6-dichloro-N-(2,3-difluorophenyl)pyrimidin-4-amine (Int-39)

5-Bromo-2,4,6-trichloropyrimidine (2.30 g, 8.33 mmol) was dissolved in THF (14 mL) and water (7 mL), and sodium acetate (2.05 g, 25.0 mmol), followed by 2,3-difluoroaniline (1.15 g, 0.90 mL, 8.7 mmol) were added. The mixture was stirred at room temperature for 18 h. After that, a saturated aqueous solution of sodium hydrogencarbonate (20 mL) was added and the resulting mixture was extracted with ethyl acetate (2×100 mL). The combined organic layers were dried (sodium sulfate) and concentrated in vacuo. The crude was purified by column chromatography (silica gel, 80 g, eluting with ethyl acetate/n-heptane, gradient 0:100 to 10:90) to yield, after drying in vacuo (40° C., 5 mbar), the title compound as a light brown solid (1.23 g, 42%). HPLC (method LCMS_fastgradient) $t_R$=1.38 min. $^1$H NMR (CDCl$_3$, 300 MHz): δ 6.97-7.09 (m, 1H), 7.13-7.23 (m, 1H), 7.72 (br s, 1H), 8.03-8.11 (m, 1H). MS (ES+) m/z 353.8, 355.8, 357.8 [M+H, Br & 2 Cl isotopes].

Step 2: 5-Bromo-2,6-dichloro-N-(2,3-difluorophenyl)-N-(2-methylallyl)pyrimidin-4-amine (Int-40)

5-Bromo-2,6-dichloro-N-(2,3-difluorophenyl)pyrimidin-4-amine (Int-39, 1.23 g, 3.47 mmol) was dissolved in dimethylformamide (11 mL) and sodium hydride (60% dispersion in mineral oil, 193 mg, 4.82 mmol) was added carefully (gas evolution). The mixture was stirred at room temperature for 1 h. Then, 3-bromo-2-methylprop-1-ene (830 mg, 6.15 mmol) was added and the resulting mixture was stirred for 16 h at 50° C. After that, water (15 mL) was added, the mixture was extracted with methyltertbutyl ether (2×80 mL), the organic phases were washed with water (3×15 mL) and brine (15 mL), combined, dried (sodium sulfate), and concentrated in vacuo. The crude product was purified by column chromatography (silica gel, 80 g, eluting with ethyl acetate/n-heptane, gradient 0:100 to 5:95) to afford the title compound as a yellow oil (1.20 g, 76%).

HPLC (method LCMS_fastgradient) $t_R$=1.65 min. $^1$H NMR (CDCl$_3$, 300 MHz): δ 1.80 (s, 3H), 4.60 (s, 2H), 4.83-4.86 (m, 1H), 4.88-4.91 (m, 1H), 6.94-7.01 (m, 1H), 7.03-7.15 (m, 2H). MS (ES+) m/z 408.1, 410.1, 412.1 [M+H, Br & 2 Cl isotopes].

Step 3: 5-Bromo-2-chloro-N4-(2,3-difluorophenyl)-N6-methyl-N4-(2-methylallyl)-pyrimidine-4,6-diamine (Int-41)

5-Bromo-2,6-dichloro-N-(2,3-difluorophenyl)-N-(2-methylallyl)pyrimidin-4-amine (Int-40, 1.19 g, 2.62 mmol) was dissolved in tetrahydrofuran (6.5 mL), the solution was cooled to 0-5° C. (ice bath) and a solution of methylamine in tetrahydrofuran (2.0 M, 4.8 mL, 9.6 mmol) was added dropwise. The mixture was stirred at room temperature for 1.5 h. After that, water (10 mL) was added, the mixture was extracted with ethyl acetate (2×80 mL), the organic layers were washed with brine (10 mL), combined, dried (sodium sulfate) and concentrated in vacuo. The crude product was purified by column chromatography (silica gel, 40 g, eluting with ethyl acetate/n-heptane, gradient 0:100 to 5:95) to obtain the title compound as a colorless oil (578 mg, 55%). HPLC (method LCMS_fastgradient) $t_R$=1.56 min. $^1$H NMR (CDCl$_3$, 300 MHz): δ 1.78 (s, 3H), 3.05 (d, J=4.8 Hz, 3H), 4.53 (s, 2H), 4.83-4.87 (m, 1H), 4.87-4.90 (m, 1H), 5.45-5.56 (m, 1H), 6.87-6.94 (m, 1H), 6.95-7.03 (m, 2H). MS (ES+) m/z 402.9, 404.8, 406.9 [M+H, Br & Cl isotopes].

Step 4: 2-Chloro-7-(2,3-difluorophenyl)-N,5,5-trimethyl-6,7-dihydro-5H-pyrrolo[2,3-d]pyrimidin-4-amine (Int-38)

5-Bromo-2-chloro-N4-(2,3-difluorophenyl)-N6-methyl-N4-(2-methylallyl)pyrimidine-4,6-diamine (Int-41, 565 mg, 1.40 mmol), sodium formate (101 mg, 1.48 mmol), tetrabutylammonium chloride (397 mg, 1.43 mmol) and palladium (II) acetate (72 mg, 321 μmol) were charged under argon in a 25 mL round bottomed flask. Dimethylformamide (4.2 mL), followed by triethylamine (363 mg, 3.59 mmol) were added and the flask was evacuated carefully and backfilled with argon. The resulting mixture was stirred at 80° C. for 18 h. After cooling, water (5 mL) was added, the mixture was extracted with methyltertbutyl ether (2×70 mL), the organic layers were washed with water (3×5 mL) and brine (1×5 mL), combined, dried (sodium sulfate) and concentrated in vacuo. The crude product was purified by column chromatography (silica gel, 24 g, eluting with ethyl acetate/n-heptane, gradient 0:100 to 20:80) to yield the title compound as a light yellow solid (382 mg, 84%). HPLC (method LCMS_fastgradient) $t_R$=1.36 min. $^1$H NMR (CDCl$_3$, 300 MHz): δ 1.42 (s, 6H), 3.08 (d, J=4.8 Hz, 3H), 3.75 (d, J=1.6 Hz, 2H), 4.29-4.40 (m, 1H), 6.93-7.03 (m, 1H), 7.03-7.12 (m, 1H), 7.35-7.43 (m, 1H). MS (ES+) m/z 325.0, 327.0 [M+H, Cl isotopes].

Int-42: 2-Chloro-7-(2,4-difluorophenyl)-N,5,5-trimethyl-6,7-dihydro-5H-pyrrolo[2,3-d]pyrimidin-4-amine

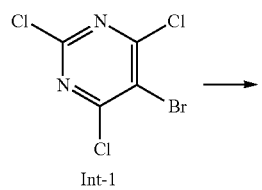

Int-1

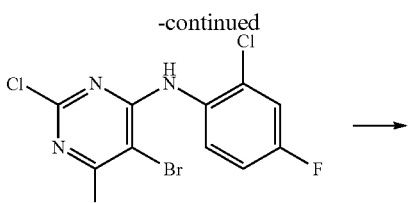

Int-43

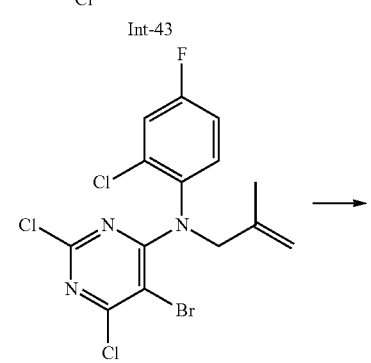

Int-44

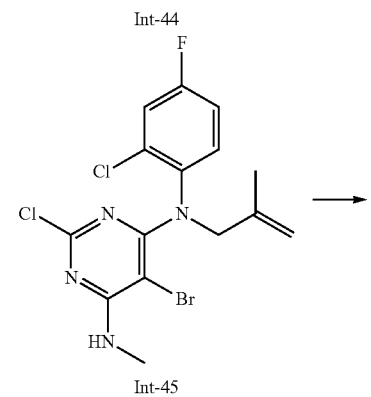

Int-45

Int-42

Step 1: 5-Bromo-2,6-dichloro-N-(2-chloro-4-fluorophenyl)pyrimidin-4-amine (Int-43)

2-Chloro-4-fluoroaniline (512 mg, 0.42 mL, 3.45 mmol) was dissolved in THF (10 mL), the solution was cooled to 0-5° C. (ice bath) and a solution of lithium bis(trimethylsilyl)amide in tetrahydrofuran/ethylbenzene (1.0 M, 3.4 mL, 3.4 mmol) was added. After stirring for 15 min at 0-5° C., a solution of 5-bromo-2,4,6-trichloropyrimidine (900 mg, 3.26 mmol) in tetrahydrofuran (7 mL) was added dropwise. The reaction mixture was stirred for 18 h at room temperature. During that period, two additional portions of a solution of lithium bis(trimethylsilyl)amide in tetrahydrofuran/ethylbenzene (1.0 M, 1.7 mL & 0.82 mL, 1.7 mmol & 0.82 mmol) were added at 0-5° C. after 45 min and 2 h, respectively. Then, water (10 mL) and a saturated aqueous solution of ammonium chloride (30 mL) were added and the resulting mixture was extracted with ethyl acetate (2×150 mL). The organic layers were washed with water (15 mL) and brine (15 mL), combined, dried (sodium sulfate) and concentrated in vacuo. The crude was purified by column chromatography (silica gel, 40 g, eluting with ethyl acetate/ n-heptane, gradient 0:100 to 5:95) to yield, after drying in vacuo (40° C., 5 mbar), the title compound as an off-white solid (956 mg, 79%). HPLC (method LCMS_fastgradient) $t_R$=1.47 min. $^1$H NMR (CDCl$_3$, 300 MHz): δ 7.08-7.16 (m, 1H), 7.24 (dd, J=2.8, 7.9 Hz, 1H), 7.99 (br s, 1H), 8.33 (dd, J=5.4, 9.3 Hz, 1H). MS (ES+) m/z 370.0, 372.0, 374.0 [M+H, Br & 3 Cl isotopes].

Step 2: 5-Bromo-2,6-dichloro-N-(2-chloro-4-fluoro-phenyl)-N-(2-methylallyl)pyrimidin-4-amine (Int-44)

5-Bromo-2,6-dichloro-N-(2-chloro-4-fluorophenyl)py-rimidin-4-amine (Int-43, 1.61 g, 4.33 mmol) was dissolved in dimethylformamide (14 mL) and sodium hydride (60% dispersion in mineral oil, 241 mg, 6.03 mmol) was added carefully (gas evolution). The mixture was stirred at room temperature for 1 h. Then, 3-bromo-2-methylprop-1-ene (1.00 g, 7.44 mmol) was added and the resulting mixture was stirred for 4.5 h at 60° C. After that, a second portion of sodium hydride (60% dispersion in mineral oil, 80 mg, 2.0 mmol) and 3-bromo-2-methylprop-1-ene (335 mg, 2.48 mmol) was added and the resulting mixture was stirred for 16 h at 60° C. After cooling to room temperature, water (15 mL) was added, the mixture was extracted with methyltert-butyl ether (2×80 mL), the organic phases were washed with water (3×15 mL) and brine (15 mL), combined, dried (sodium sulfate), and concentrated in vacuo. The crude product was purified by column chromatography (silica gel, 80 g, eluting with ethyl acetate/n-heptane, gradient 0:100 to 5:95) to afford the title compound as a light yellow oil (1.73 g, 84%). HPLC (method LCMS_fastgradient) $t_R$=1.71 min. $^1$H NMR (CDCl$_3$, 300 MHz): δ 1.82 (s, 3H), 4.32-4.62 (br s, exch., 2H), 4.77-4.82 (m, 1H), 4.88-4.92 (m, 1H), 6.98-7.06 (m, 1H), 7.16-7.26 (m, 2H). MS (ES+) m/z 423.8, 425.8, 427.8 [M+H, Br & 3 Cl isotopes].

Step 3: 5-Bromo-2-chloro-N4-(2-chloro-4-fluoro-phenyl)-N6-methyl-N4-(2-methylallyl)-pyrimidine-4,6-diamine (Int-45)

5-Bromo-2,6-dichloro-N-(2-chloro-4-fluorophenyl)-N-(2-methylallyl)pyrimidin-4-amine (Int-44, 1.73 g, 3.66 mmol) was dissolved in tetrahydrofuran (10 mL), the solution was cooled to 0-5° C. (ice bath) and a solution of methylamine in tetrahydrofuran (2.0 M, 6.75 mL, 13.5 mmol) was added dropwise. The mixture was stirred at room temperature for 1.5 h. After that, water (15 mL) was added, the mixture was extracted with ethyl acetate (2×110 mL), the organic layers were washed with brine (15 mL), combined, dried (sodium sulfate) and concentrated in vacuo. The crude product was purified by column chromatography (silica gel, 80 g, eluting with ethyl acetate/n-heptane, gradient 0:100 to 5:95) to obtain the title compound as a colorless oil (658 mg, 43%). HPLC (method LCMS_fastgradient) $t_R$=1.62 min. $^1$H NMR (CDCl$_3$, 300 MHz): δ 1.80 (s, 3H), 3.03 (d, J=4.8 Hz, 3H), 4.44 (s, 2H), 4.81-4.86 (m, 2H), 5.42-5.52 (m, 1H), 6.95 (ddd, J=2.8, 7.7, 8.9 Hz, 1H), 7.14 (dd, J=2.8, 8.3 Hz, 1H), 7.18 (dd, J=5.6, 8.9 Hz, 1H). MS (ES+) m/z 418.9, 420.8, 422.9 [M+H, Br & 2 Cl isotopes].

Step 4: 2-Chloro-7-(2-chloro-4-fluorophenyl)-N,5,5-trimethyl-6,7-dihydro-5H-pyrrolo[2,3-d]pyrimidin-4-amine (Int-42)

5-Bromo-2-chloro-N4-(2-chloro-4-fluorophenyl)-N6-methyl-N4-(2-methylallyl)-pyrimidine-4,6-diamine (Int-45, 645 mg, 1.54 mmol), sodium formate (111 mg, 1.63 mmol), tetrabutylammonium chloride (435 mg, 1.57 mmol) and palladium (II) acetate (79 mg, 352 μmol) were charged under argon in a 25 mL round bottomed flask. Dimethyl-formamide (4.6 mL), followed by triethylamine (399 mg, 3.95 mmol) were added and the flask was evacuated carefully and backfilled with argon. The resulting mixture was stirred at 80° C. for 18 h. After cooling, water (5 mL) was added, the mixture was extracted with methyltertbutyl ether (2×70 mL), the organic layers were washed with water (3×5 mL) and brine (1×5 mL), combined, dried (sodium sulfate) and concentrated in vacuo. The crude product was purified by column chromatography (silica gel, 40 g, eluting with ethyl acetate/n-heptane, gradient 0:100 to 20:80) to yield the title compound as a light yellow solid (344 mg, 66%). HPLC (method LCMS_fastgradient) $t_R$=1.39 min. $^1$H NMR (CDCl$_3$, 300 MHz): δ 1.43 (s, 6H), 3.07 (d, J=4.8 Hz, 3H), 3.61 (s, 2H), 4.26-4.35 (m, 1H), 7.03 (ddd, J=2.9, 7.8, 8.9 Hz, 1H), 7.19 (dd, J=2.8, 8.3 Hz, 1H), 7.35 (dd, J=5.4, 8.9 Hz, 1H). MS (ES+) m/z 341.2, 343.1 [M+H, 2 Cl isotopes].

tert-Butyl N-[(1R,5S,8s)-3-azabicyclo[3.2.1]octan-8-yl] carbamate (Int-47) was synthesized according to procedures described in WO2012/116965.

Int-49: (1R,5S,8s)-3-(5-Methyl-1,3,4-oxadiazol-2-yl)-3-azabicyclo[3.2.1]octan-8-amine

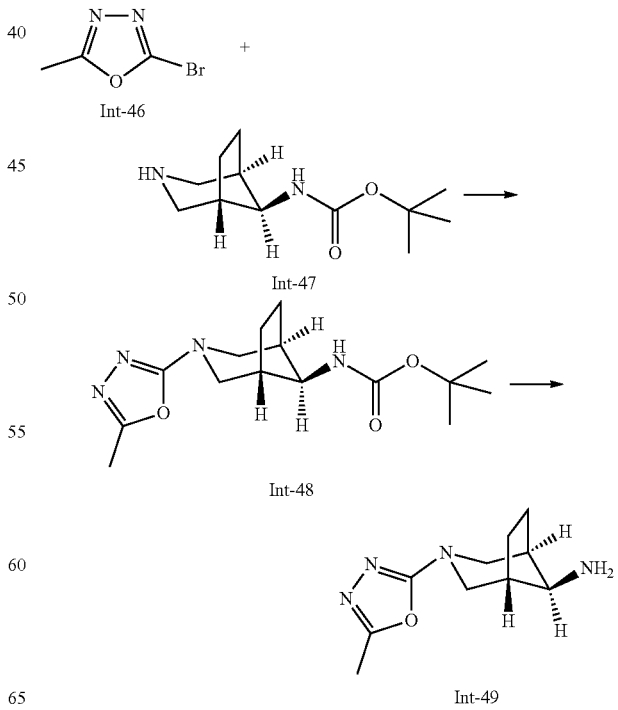

Step 1: tert-Butyl N-[(1R,5S,8s)-3-(5-methyl-1,3,4-oxadiazol-2-yl)-3-azabicyclo[3.2.1]octan-8-yl]carbamate (Int-48)

To a solution of tert-butyl N-[(1R,5S,8s)-3-azabicyclo[3.2.1]octan-8-yl]carbamate (Int-47, 50 mg, 0.2 mmol) in MeOH (1.3 mL) was added 2-bromo-5-methyl-1,3,4-oxadiazole (Int-46, 72 mg, 0.4 mmol) and triethylamine (0.1 ml, 0.8 mmol) in a sealed tube. The reaction was stirred at 130° C. for 16 h. After complete consumption of starting material (as monitored by TLC) reaction mixture was concentrated in vacuo followed by column chromatography (silica gel, eluting with EtOAc/n-hexane 60:40 v/v) to yield the title compound as white solid (50 mg, 73%). 10 $^1$H NMR (DMSO-d6, 400 MHz): 1.39 (s, 10H), 1.79-1.87 (m, 2H), 2.22 (s, 2H), 2.31 (s, 3H), 3.14 (d, J=11.5 Hz, 2H), 3.47-3.52 (m, 3H), 6.81 (br s, 1H). MS (ES+) m/z 309.0 [M+H].

Step 2: (1R,5S,8s)-3-(5-Methyl-1,3,4-oxadiazol-2-yl)-3-azabicyclo[3.2.1]octan-8-amine (Int-49)

To a solution of tert-butyl N-[(1R,5S,8s)-3-(5-methyl-1,3,4-oxadiazol-2-yl)-3-azabicyclo[3.2.1]octan-8-yl]carbamate (Int-48, 500 mg, 1.6 mmol) in dichloromethane (10 mL) was added trifluoroacetic acid (1.2 mL, 16.2 mmol) at 0° C. After 5 min reaction mixture was allowed to warm to 25° C. and continued the stirring at the same temperature for 2 h. The resulting mixture was concentrated under reduced pressure followed by azeotrope with toluene (3×5 mL) to afford the crude which was purified by column chromatography (amino modified silica gel, eluting with MeOH/dichloromethane 10:90 v/v) to yield the title compound as off-white solid (250 mg, 73%). $^1$H NMR (DMSO-d6, 400 MHz): 1.37 (d, J=7.6 Hz, 2H), 1.87-1.89 (m, 2H), 1.97 (s, 2H), 2.30 (s, 3H), 2.99 (s, 1H), 3.07 (d, J=11.5 Hz, 2H), 3.47 (d, J=11.5 Hz, 2H). MS (ES+) m/z 209.1 [M+H].

Int-52: (1R,5S,8s)-3-(2-Methoxy-4-pyridyl)-3-azabicyclo[3.2.1]octan-8-amine

Step 1: tert-Butyl N-[(1R,5S,8s)-3-(2-methoxy-4-pyridyl)-3-azabicyclo[3.2.1]octan-8-yl]carbamate (Int-51)

To a solution of tert-butyl N-[(1R,5S,8s)-3-azabicyclo[3.2.1]octan-8-yl]carbamate (Int-47, 50 mg, 0.2 mmol) and 4-bromo-2-methoxypyridine (Int-50, 41 mg, 0.2 mmol) in dry toluene (2.5 mL) in sealed tube was degassed with argon over a period of 5 min. To it then added sodium tertbutoxide (63.7 mg, 0.7 mmol) and 4,5-bis(diphenylphosphino)-9,9-dimethylxanthene ("Xantphos", CAS [161265-03-8], 1.3 mg, 0.0 mmol). The reaction mixture was again degassed with argon for 5 min followed by addition of tris(dibenzylideneacetone)dipalladium(0) ("Pd$_2$(dba)$_3$", CAS [51364-51-3], 4.0 mg, 0.0 mmol). The reaction mixture was stirred at 100° C. for 16 h. Reaction mixture was then concentrated under reduced pressure to get crude which was purified by column chromatography (silica gel, eluting with EtOAc/n-hexane 10:90 v/v) to yield the title compound as off white solid (30 mg, 40%). $^1$H NMR (DMSO-d6, 400 MHz): 1.39 (s, 9H), 1.81 (s, 2H), 2.26 (br s, 2H), 2.84 (d, J=11.2 Hz, 2H), 3.48 (br s, 1H), 3.56 (d, J=10.4 Hz, 2H), 3.74 (s, 3H), 5.97 (s, 1H), 6.45 (d, J=4.2 Hz, 1H), 6.79 (s, 1H), 7.74 (d, J=5.8 Hz, 1H). MS (ES+) m/z 334.2 [M+H].

Step 2: (1R,5S,8s)-3-(2-Methoxy-4-pyridyl)-3-azabicyclo[3.2.1]octan-8-amine (Int-52)

To a solution of tert-butyl N-[(1R,5S,8s)-3-(2-methoxy-4-pyridyl)-3-azabicyclo[3.2.1]octan-8-yl]carbamate (Int-51, 100 mg, 0.3 mmol) in dichloromethane (5.0 mL) was added trifluoroacetic acid (0.2 mL, 3.0 mmol) at 0° C. After 5 min reaction mixture was allowed to warm to 25° C. and continued the stirring at the same temperature for 4 h. The resulting mixture was concentrated under reduced pressure followed by dilution with saturated potassium carbonate solution (10 mL) and extraction with 10% MeOH in dichloromethane (6×20 mL). After drying the separated organic part, the solvent was evaporated to afford the title compound as yellow semi-solid (50 mg, crude). MS (ES+) m/z 234.3 [M+H].

Int-55: (1R,5S,8s)-3-(6-Methylpyrimidin-4-yl)-3-azabicyclo[3.2.1]octan-8-amine

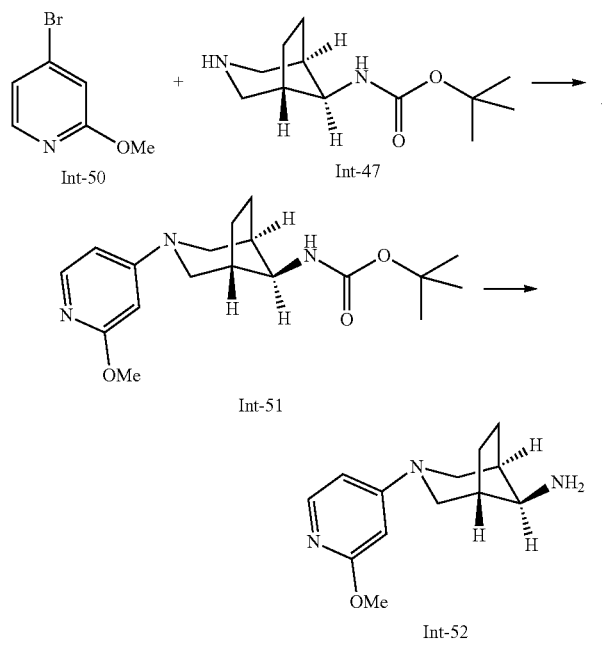

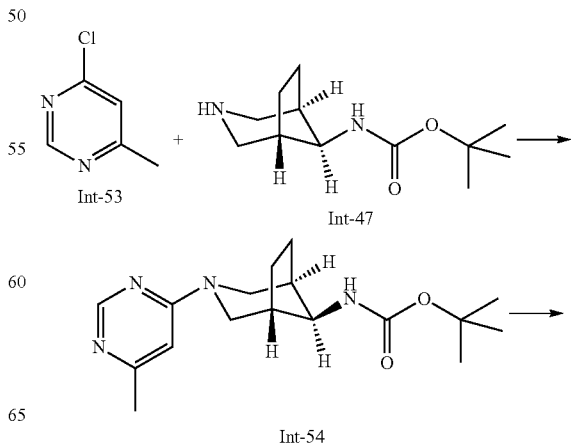

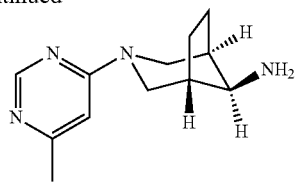

Int-55

Step 1: tert-Butyl N-[(1R,5S,8s)-3-(6-methylpyrimidin-4-yl)-3-azabicyclo[3.2.1]octan-8-yl]carbamate (Int-54)

In a sealed tube tert-butyl N-[(1R,5S,8s)-3-azabicyclo[3.2.1]octan-8-yl]carbamate (Int-47, 500 mg, 2.21 mmol) was dissolved in EtOH (10 mL) and 4-chloro-6-methylpyrimidine (869 mg, 6.63 mmol) was added followed by triethylamine (894 mg, 1.23 mL, 8.84 mmol). The reaction mixture was stirred at 130° C. overnight. The crude reaction mixture was concentrated in vacuum. The residue was diluted with 20 mL of $CH_2Cl_2$ and 20 mL of water. The organic phase was extracted with $CH_2Cl_2$ (3×20 mL), dried over $MgSO_4$ and concentrated in vacuum. The crude material was purified by flash chromatography (0% to 100% EtOAc in heptane) to afford the title compound as a yellow solid (496 mg, 71% yield). MS (ES+) m/z: 319.2 [M+H].

Step 2: (1R,5S,8s)-3-(6-Methylpyrimidin-4-yl)-3-azabicyclo[3.2.1]octan-8-amine (Int-55)

To a light yellow solution of tert-butyl N-[(1R,5S,8s)-3-(6-methylpyrimidin-4-yl)-3-azabicyclo[3.2.1]octan-8-yl]carbamate (Int-54, 260 mg, 817 µmol) in $CH_2Cl_2$ (8 mL) was added TFA (931 mg, 629 µl, 8.17 mmol). The reaction mixture was stirred at room temperature over night and concentrated in vacuum. The crude material was purified by Ion-exchange column (Si—SCX-2, 10 g, washed with MeOH and liberated with MeOH ($NH_3$ 2M)) to afford the title compound (195 mg, 804 µmol, 98.5% yield) that was used in the next step without further purification. MS (ES+) m/z: 219.2 [M+H].

Int-58: (1R,5S,8s)-3-(6-Methoxypyrimidin-4-yl)-3-azabicyclo[3.2.1]octan-8-amine

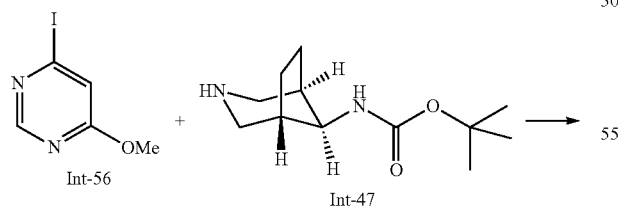

Int-56      Int-47

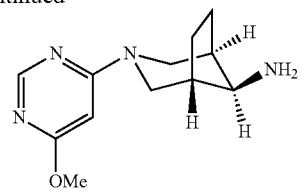

Int-58

Step 1: tert-Butyl N-[(1R,5S,8s)-3-(6-methoxypyrimidin-4-yl)-3-azabicyclo[3.2.1]octan-8-yl]carbamate (Int-57)

In analogy to the preparation of intermediate Int-54 from tert-butyl N-[(1R,5S,8s)-3-azabicyclo[3.2.1]octan-8-yl]carbamate (Int-47, 250 mg, 1.1 mmol) and 4-iodo-6-methoxypyrimidine (Int-56, 391 mg, 1.66 mmol) in a sealed tube at 100° C. using DMF as solvent in the presence of $K_2CO_3$ (458 mg, 3.31 mmol), the title compound (315 mg, 85% yield) was obtained as a white solid. MS (ES+) m/z: 335.2 [M+H].

Step 2: (1R,5S,8s)-3-(6-Methoxypyrimidin-4-yl)-3-azabicyclo[3.2.1]octan-8-amine (Int-58)

In analogy to the preparation of intermediate Int-55 from tert-butyl N-[(1R,5S,8s)-3-(6-methoxypyrimidin-4-yl)-3-azabicyclo[3.2.1]octan-8-yl]carbamate (Int-57, 330 mg, 987 µmol) in $CH_2Cl_2$ in the presence of TFA (1.13 g, 760 µl, 9.87 mmol), the title compound (222 mg, 96% yield) was obtained as a white solid and used directly in the next step without further purification. MS (ES+) m/z: 235.2 [M+H].

Int-62: (1R,5S,8s)-3-(6-Methoxypyridazin-4-yl)-3-azabicyclo[3.2.1]octan-8-amine

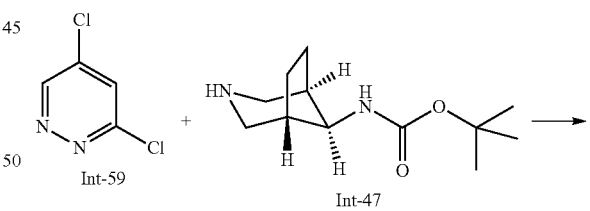

Int-59      Int-47

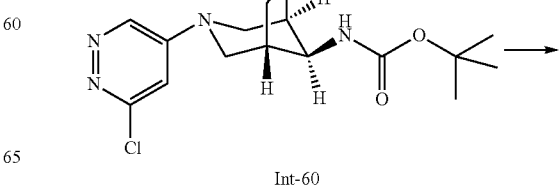

Int-60

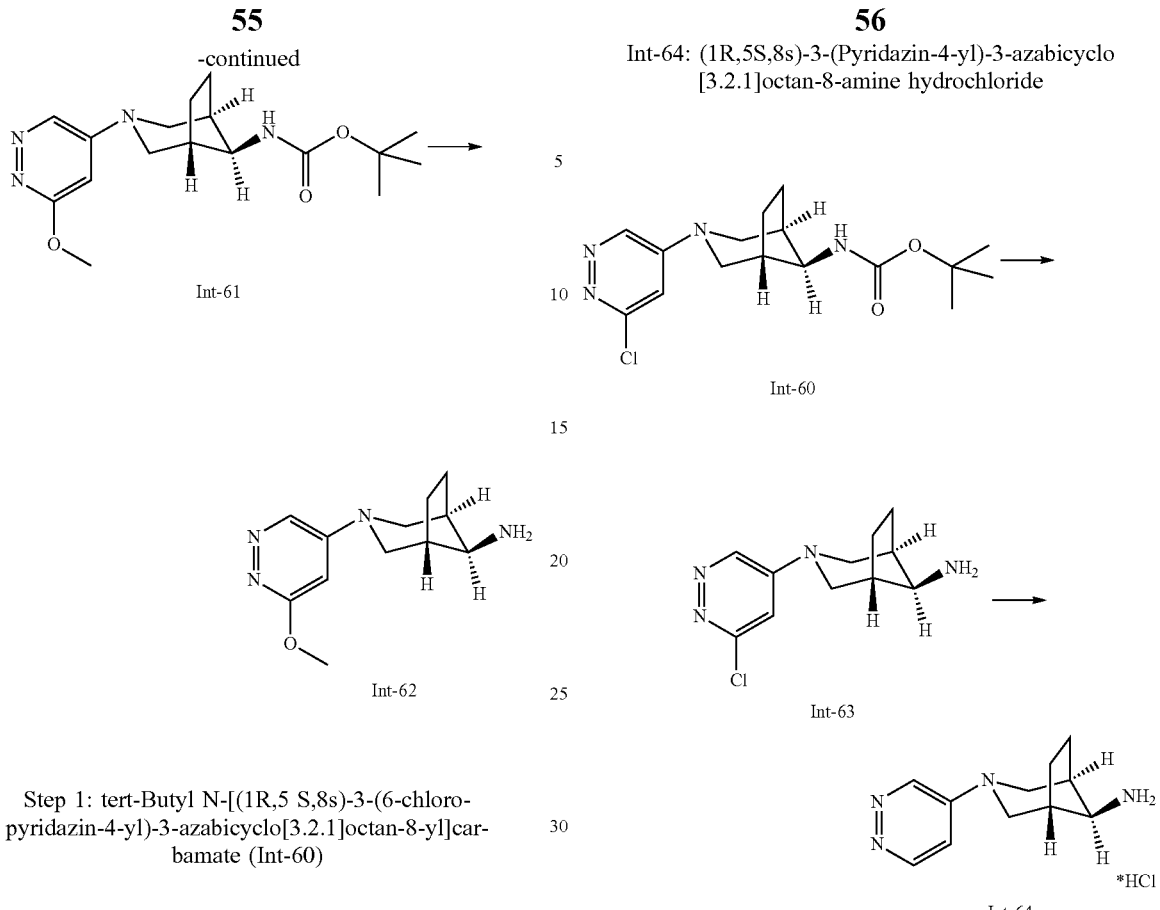

Int-64: (1R,5S,8s)-3-(Pyridazin-4-yl)-3-azabicyclo[3.2.1]octan-8-amine hydrochloride

Step 1: tert-Butyl N-[(1R,5 S,8s)-3-(6-chloro-pyridazin-4-yl)-3-azabicyclo[3.2.1]octan-8-yl]carbamate (Int-60)

In analogy to the preparation of the intermediate Int-54 from tert-butyl N-[(1R,5S,8s)-3-azabicyclo[3.2.1]octan-8-yl]carbamate (Int-47, 2.00 g, 8.84 mmol) and 3,5-dichloropyridazine (Int-59, 2.0 g, 13.4 mmol) in a sealed tube at 90° C. using EtOH as solvent in the presence of Et₃N (3.63 g, 5.0 mL, 35.9 mmol), the title compound (1.71 g, 54%) was obtained as a white solid. MS (ES+) m/z: 339.2 [M+H].

Step 2: tert-Butyl N-[(1R,5S,8s)-3-(6-methoxypyridazin-4-yl)-3-azabicyclo[3.2.1]octan-8-yl]carbamate (Int-61)

To a solution of tert-butyl N-[(1R,5S,8s)-3-(6-chloro-pyridazin-4-yl)-3-azabicyclo[3.2.1]octan-8-yl]carbamate (Int-60, 963 mg, 2.70 mmol) in MeOH (22 mL) in a sealed tube was added a solution of NaOMe in methanol (25%, 1.9 mL, 8.3 mmol). The reaction mixture was heated at 85° C. over night. The reaction mixture was adsorbed on Isolute HM-N and a column chromatography gave the title compound (362 mg, 38%) as a white solid. MS (ES+) m/z: 335.2 [M+H].

Step 3: (1R,5S,8s)-3-(6-Methoxypyridazin-4-yl)-3-azabicyclo[3.2.1]octan-8-amine (Int-62)

In analogy to the preparation of intermediate Int-55 from tert-butyl N-[(1R,5S,8s)-3-(6-methoxypyridazin-4-yl)-3-azabicyclo[3.2.1]octan-8-yl]carbamate (Int-61, 0.93 g, 2.72 mmol) in CH₂Cl₂ in the presence of TFA (1.12 g, 0.76 mL, 9.86 mmol), the title compound (225 mg, 96%) was obtained as a white solid and used directly in the next step without further purification. MS (ES+) m/z: 235.2 [M+H].

Step 1: (1R,5 S,8s)-3-(6-Chloropyridazin-4-yl)-3-azabicyclo[3.2.1]octan-8-amine (Int-63)

In analogy to the preparation of intermediate Int-55 from tert-butyl N-[(1R,5S,8s)-3-(6-chloropyridazin-4-yl)-3-azabicyclo[3.2.1]octan-8-yl]carbamate (Int-60, 0.93 g, 2.72 mmol) in CH₂Cl₂ in the presence of HCl 37% (1.61 g, 1.34 mL, 16.3 mmol), the title compound (0.65 g, 100%) was obtained as a white solid and used directly in the next step without further purification. MS (ES+) m/z: 239.1 [M+H].

Step 2: (1R,5S,8s)-3-(Pyridazin-4-yl)-3-azabicyclo[3.2.1]octan-8-amine hydrochloride (Int-64)

(1R,5S,8s)-3-(6-Chloropyridazin-4-yl)-3-azabicyclo[3.2.1]octan-8-amine (Int-63, 350 mg, 1.47 mmol) was dissolved in methanol (20 mL), Palladium on charcoal (10% m/m, 156 mg, 0.15 mmol) was added and the mixture was stirred for 2 h at room temperature under a hydrogen atmosphere (balloon). After that, it was filtered over a short plug of Celite, washed with methanol (40 mL) and the filtrate was concentrated in vacuo. The crude product, that was obtained as hydrochloride salt and as an off-white foam, was used in the next step without further purification (350 mg, 99%). MS (ES+) m/z: 205.1 [M+H].

EXAMPLES

Example 1

7-(4-Fluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine

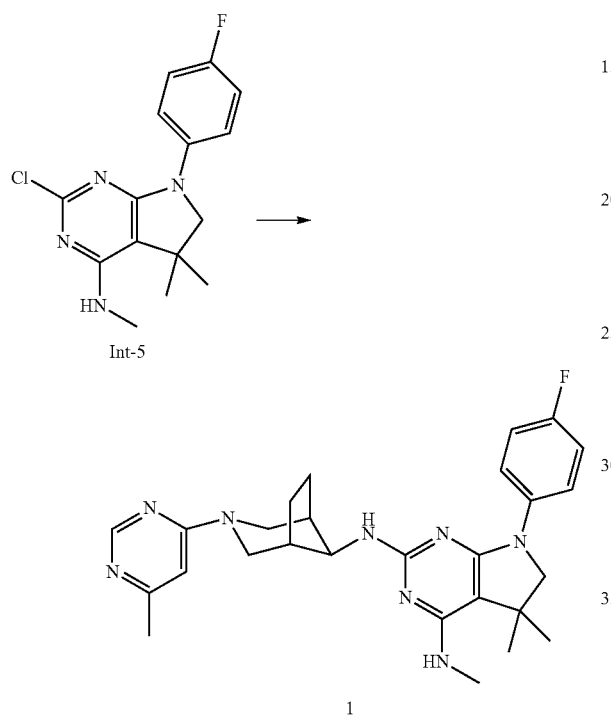

Example 2

7-(4-Fluorophenyl)-N4,5,5-trimethyl-N2-((1R,5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine

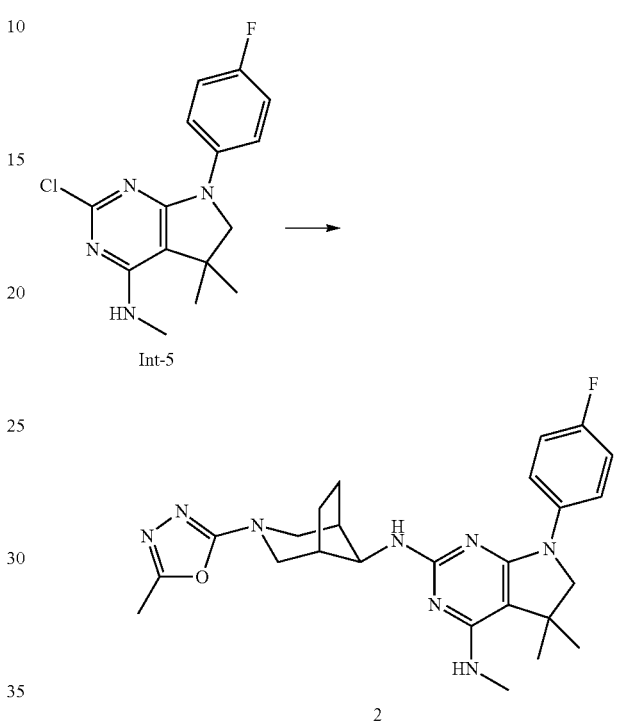

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 70 mg, 228 µmol) was dissolved in NMP (1.5 mL) and (1R,5S,8S)-3-(6-methylpyrimidin-4-yl)-3-azabicyclo[3.2.1]octan-8-amine (75 mg, 344 µmol), cesium carbonate (149 mg, 456 µmol), 2-dicyclohexylphosphino-2'-(N,N-dimethyl-amino)biphenyl (18 mg, 45.6 µmol), and bis(dibenzylideneacetone)palladium(0) (24 mg, 41.7 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as an off-white foam (38 mg, 32%). HPLC (method LCMS_fastgradient) $t_R$=0.80 min. $^1$H NMR (CDCl$_3$, 300 MHz): δ 1.39 (s, 6H), 1.55-1.62 (m, 2H), 1.89-1.99 (m, 2H), 2.38 (s, 3H), 2.51-2.58 (m, 2H), 3.02 (d, J=4.8 Hz, 3H), 3.14 (d, J=12.3 Hz, 2H), 3.62 (s, 2H), 4.03-4.25 (m, 4H), 4.64 (d, J=5.4 Hz, 1H), 6.38 (s, 1H), 7.02 (dd, J=8.5, 9.3 Hz, 2H), 7.68 (dd, J=4.8, 8.9 Hz, 2H), 8.53 (d, J=0.8 Hz, 1H). MS (ES+) m/z 489.3 [M+H].

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 55 mg, 179 µmol) was dissolved in NMP (1.2 mL) and (1R,5S,8S)-3-(5-methyl-1,3,4-oxadiazol-2-yl)-3-azabicyclo[3.2.1]octan-8-amine (56 mg, 269 µmol), cesium carbonate (117 mg, 359 µmol), 2-dicyclohexylphosphino-2'-(N,N-dimethyl-amino)biphenyl (15 mg, 38 µmol), and bis(dibenzylideneacetone)palladium(0) (19 mg, 33 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford the title compound as a light brown solid (31 mg, 34%). HPLC (method LCMS_fastgradient) $t_R$=0.94 min. $^1$H NMR (CDCl$_3$, 300 MHz): δ 1.38 (s, 6H), 1.63-1.73 (m, 2H), 1.92-2.01 (m, 2H), 2.41 (s, 3H), 2.46-2.53 (m, 2H), 3.01 (d, J=4.8 Hz, 3H), 3.32 (d, J=11.7 Hz, 2H), 3.61 (s, 2H), 3.77 (dd, J=3.2, 12.3 Hz, 2H), 4.01 (d, J=5.4 Hz, 1H), 4.03-4.10 (m, 1H), 4.61 (d, J=5.4 Hz, 1H), 7.01 (dd, J=8.5, 9.1 Hz, 2H), 7.66 (dd, J=4.6, 9.1 Hz, 2H). MS (ES+) m/z 479.3 [M+H].

Example 3

7-(4-Fluorophenyl)-N2-((1R,5S,8s)-3-(6-methoxy-pyridazin-4-yl)-3-azabicyclo[3.2.1]octan-8-yl)-N4,5,5-trimethyl-6,7-dihydro-5H-pyrrolo[2,3-d]pyrimidine-2,4-diamine

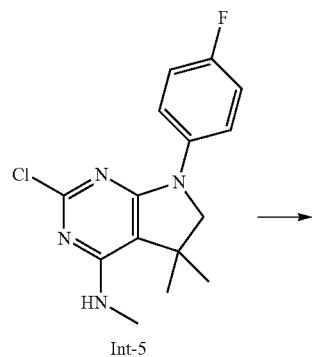

Int-5

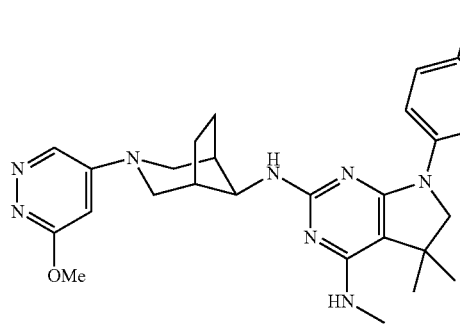

3

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 50 mg, 163 μmol) was dissolved in NMP (1.1 mL) and (1R,5S,8S)-3-(6-methoxypyridazin-4-yl)-3-azabicyclo[3.2.1]octan-8-amine (60 mg, 256 μmol), cesium carbonate (106 mg, 326 μmol), 2-dicyclohexylphosphino-2'-(N,N-dimethylamino)biphenyl (13 mg, 33 μmol), and bis(dibenzylideneacetone)palladium(0) (17 mg, 30 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light yellow foam (31 mg, 38%). HPLC (method LCMS_fastgradient) $t_R$=0.86 min. $^1$H NMR (CDCl$_3$, 300 MHz): δ 1.39 (s, 6H), 1.58-1.67 (m, 2H), 1.96-2.04 (m, 2H), 2.56-2.63 (m, 2H), 3.02 (d, J=5.0 Hz, 3H), 3.13-3.20 (m, 2H), 3.62 (s, 2H), 3.66 (dd, J=3.2, 11.7 Hz, 2H), 4.02-4.09 (m, 2H), 4.09 (s, 3H), 4.64 (d, J=5.4 Hz, 1H), 6.05 (d, J=2.6 Hz, 1H), 7.01 (dd, J=8.4, 9.2 Hz, 2H), 7.62-7.69 (m, 2H), 8.60 (d, J=2.6 Hz, 1H). MS (ES+) m/z 505.3 [M+H].

Example 4

7-(4-Fluorophenyl)-N2-((1R,5S,8s)-3-(2-methoxypyridin-4-yl)-3-azabicyclo[3.2.1]octan-8-yl)-N4,5,5-trimethyl-6,7-dihydro-5H-pyrrolo[2,3-d]pyrimidine-2,4-diamine

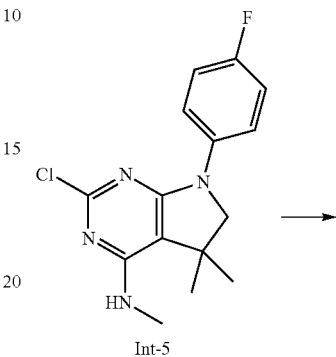

Int-5

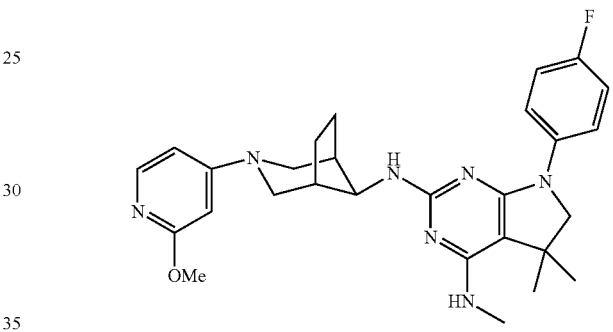

4

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 50 mg, 163 μmol) was dissolved in NMP (1.1 mL) and (1R,5S,8S)-3-(2-methoxypyridin-4-yl)-3-azabicyclo[3.2.1]octan-8-amine (54 mg, 231 μmol), cesium carbonate (106 mg, 326 μmol), 2-dicyclohexylphosphino-2'-(N,N-dimethyl-amino)biphenyl (13 mg, 33 μmol), and bis(dibenzylideneacetone)palladium(0) (17 mg, 30 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light yellow foam (32 mg, 37%). HPLC (method LCMS_fastgradient) $t_R$=0.78 min. $^1$H NMR (CDCl$_3$, 300 MHz): δ 1.38 (s, 6H), 1.60-1.68 (m, 2H), 1.92-2.01 (m, 2H), 2.51-2.58 (m, 2H), 3.02 (d, J=4.8 Hz, 3H), 3.06-3.13 (m, 2H), 3.60-3.67 (m, 2H), 3.61 (s, 2H), 3.91 (s, 3H), 4.00-4.09 (m, 2H), 4.65 (d, J=5.4 Hz, 1H), 6.03 (d, J=2.2 Hz, 1H), 6.38 (dd, J=2.4, 6.2 Hz, 1H), 7.01 (dd, J=8.4, 9.2 Hz, 2H), 7.63-7.71 (m, 2H), 7.89 (d, J=6.2 Hz, 1H). MS (ES+) m/z 504.3 [M+H].

Example 5

N2-((1R,5S,8s)-3-(6-Chloropyrimidin-4-yl)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine

Example 6

7-(4-Fluorophenyl)-N2-((1R,5S,8s)-3-(6-methoxypyrimidin-4-yl)-3-azabicyclo[3.2.1]octan-8-yl)-N4,5,5-trimethyl-6,7-dihydro-5H-pyrrolo[2,3-d]pyrimidine-2,4-diamine

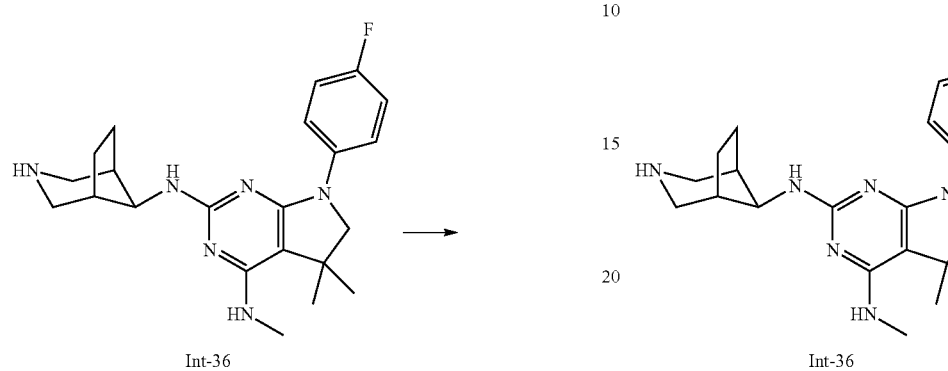

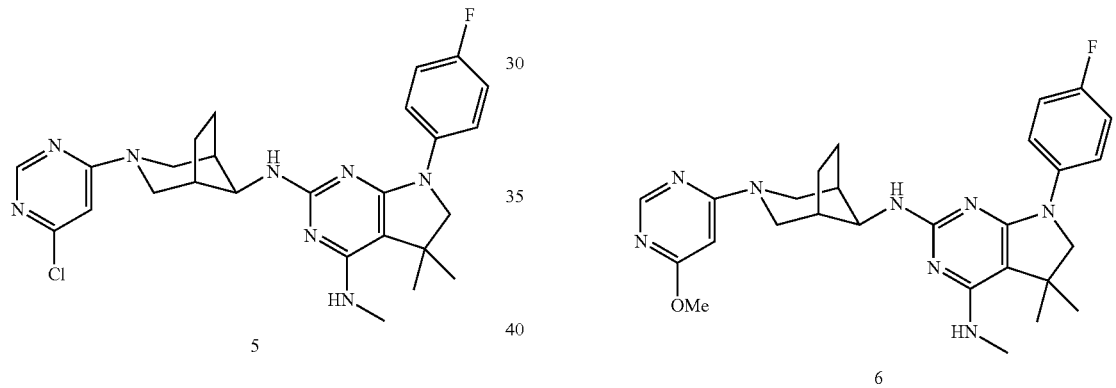

In a screw cap pressure vial, N2-((1R,5S,8s)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine (Int-36, 50 mg, 113 µmol) was suspended in ethanol (0.7 mL) and 4,6-dichloropyrimidine (26 mg, 175 µmol), followed by triethylamine (47.2 mg, 65 µL, 466 µmol) were added. The vial was flushed with Argon and closed. The reaction mixture was stirred at 90° C. for 18 h. After that, it was concentrated in vacuo and the residue was purified by column chromatography (silica gel, 12 g, eluting with ethylacetate/n-heptane, gradient 0:100 to 50:50) to yield the title compound as a light yellow solid (24 mg, 41%). HPLC (method LCMS_fastgradient) $t_R$=1.04 min. $^1$H NMR (CDCl$_3$, 300 MHz): δ 1.39 (s, 6H), 1.51-1.61 (m, 2H), 1.91-2.01 (m, 2H), 2.52-2.60 (m, 2H), 3.02 (d, J=4.8 Hz, 3H), 3.18 (d, J=12.5 Hz, 2H), 3.62 (s, 2H), 3.81-4.50 (br s, 2H), 4.05-4.11 (m, 2H), 4.63 (d, J=5.2 Hz, 1H), 6.52 (d, J=0.8 Hz, 1H), 7.02 (dd, J=8.4, 9.2 Hz, 2H), 7.67 (dd, J=4.7, 9.0 Hz, 2H), 8.40 (d, J=0.8 Hz, 1H). MS (ES+) m/z 509.3 & 511.2 [M+H, Cl isotopes].

In a screw cap pressure vial, N2-((1R,5S,8s)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine (Int-36, 50 mg, 113 µmol) was suspended in ethanol (0.7 mL) and 4-chloro-6-methoxypyrimidine (25 mg, 173 µmol), followed by triethylamine (47.2 mg, 65 µL, 466 µmol) were added. The vial was flushed with Argon and closed. The reaction mixture was stirred at 90° C. for 18 h. After that, it was concentrated in vacuo and the residue was purified by column chromatography (silica gel, 12 g, eluting with ethylacetate/n-heptane, gradient 0:100 to 50:50) to afford the title compound as a light yellow solid (31 mg, 54%). HPLC (method LCMS_fastgradient) $t_R$=0.99 min. $^1$H NMR (CDCl$_3$, 300 MHz): δ 1.38 (s, 6H), 1.54-1.63 (m, 2H), 1.89-1.98 (m, 2H), 2.49-2.57 (m, 2H), 3.01 (d, J=4.8 Hz, 3H), 3.12 (d, J=12.1 Hz, 2H), 3.61 (s, 2H), 3.93 (s, 3H), 4.02-4.15 (m, 4H), 4.64 (d, J=5.4 Hz, 1H), 5.81 (d, J=0.6 Hz, 1H), 7.01 (dd, J=8.6, 9.2 Hz, 2H), 7.67 (dd, J=4.6, 8.9 Hz, 2H), 8.34 (d, J=0.8 Hz, 1H). MS (ES+) m/z 505.4 [M+H].

Example 7

N2-((1R,5S,8s)-3-(6-Chloropyridazin-4-yl)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine

Example 8

7-(3,4-Difluorophenyl)-N4,5,5-trimethyl-N2-((1R,5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine

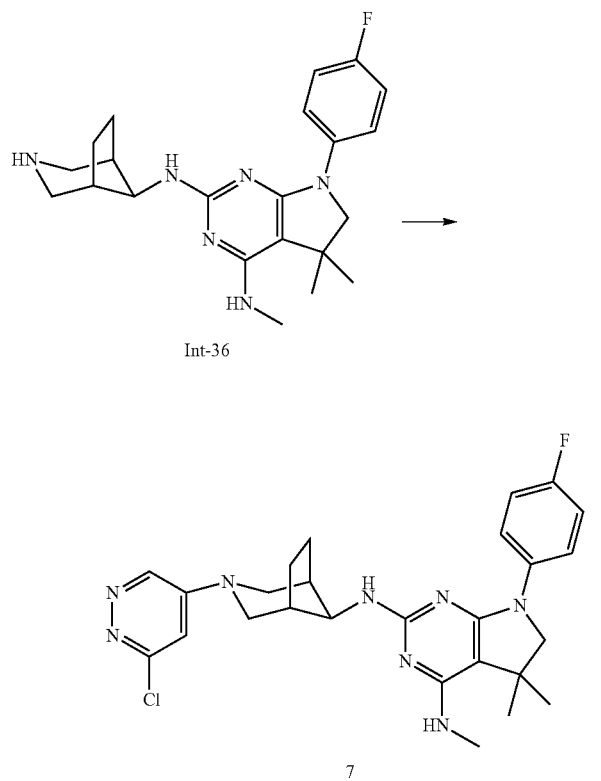 [SMILES: CNc1nc(NC2C3CCC2CNC3)nc2c1C(C)(C)CN2c1ccc(F)cc1 ; CNc1nc(NC2C3CCC2CN(c2cnnc(Cl)c2)C3)nc2c1C(C)(C)CN2c1ccc(F)cc1]

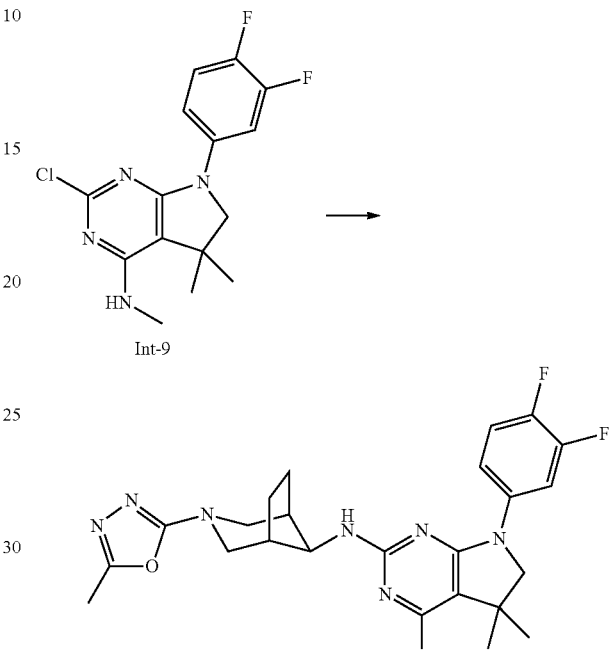

In a screw cap pressure vial, N2-((1R,5S,8s)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine (Int-36, 50 mg, 113 μmol) was suspended in ethanol (0.7 mL) and 3,5-dichloropyridazine (26 mg, 175 μmol), followed by triethylamine (47.2 mg, 65 μL, 466 μmol) were added. The vial was flushed with Argon and closed. The reaction mixture was stirred at 90° C. for 18 h. After that, it was concentrated in vacuo and the residue was purified by column chromatography (silica gel, 12 g, eluting with ethylacetate/n-heptane, gradient 0:100 to 100:0, followed by dichloromethane/methanol, gradient 100:0 to 95:5) to yield the title compound as a light yellow solid (10 mg, 17%). HPLC (method LCMS_fastgradient) $t_R$=0.95 min. $^1$H NMR (CDCl$_3$, 300 MHz): δ 1.39 (s, 6H), 1.58-1.66 (m, 2H), 2.00-2.08 (m, 2H), 2.60-2.66 (m, 2H), 3.02 (d, J=5.0 Hz, 3H), 3.24 (dd, J=1.4, 11.5 Hz, 2H), 3.62 (s, 2H), 3.70 (dd, J=3.0, 11.9 Hz, 2H), 4.06-4.12 (m, 2H), 4.63 (d, J=5.4 Hz, 1H), 6.66 (d, J=2.8 Hz, 1H), 7.01 (dd, J=8.4, 9.2 Hz, 2H), 7.65 (dd, J=4.7, 9.2 Hz, 2H), 8.75 (d, J=2.8 Hz, 1H). MS (ES+) m/z 509.3 & 511.2 [M+H, Cl isotopes].

In a 2 mL microwave vial, 2-chloro-7-(3,4-difluorophenyl)-N,5,5-trimethyl-6,7-dihydro-5H-pyrrolo[2,3-d]pyrimidin-4-amine (Int-9, 60 mg, 185 μmol) was dissolved in NMP (1.2 mL) and (1R,5S,8s)-3-(5-methyl-1,3,4-oxadiazol-2-yl)-3-azabicyclo[3.2.1]octan-8-amine (60 mg, 288 μmol), cesium carbonate (125 mg, 384 μmol), 2-dicyclohexylphosphino-2'-(N,N-dimethyl-amino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford the title compound as a light yellow solid (32 mg, 35%). HPLC (method LCMS_fastgradient) $t_R$=0.95 min. $^1$H NMR (CDCl$_3$, 300 MHz): δ 1.38 (s, 6H), 1.65-1.73 (m, 2H), 1.94-2.02 (m, 2H), 2.40 (s, 3H), 2.48-2.54 (m, 2H), 3.01 (d, J=4.8 Hz, 3H), 3.35 (d, J=11.7 Hz, 2H), 3.59 (s, 2H), 3.78 (dd, J=3.4, 12.3 Hz, 2H), 4.01 (d, J=5.4 Hz, 1H), 4.06-4.13 (m, 1H), 4.67 (d, J=5.2 Hz, 1H), 7.05-7.12 (m, 2H), 7.98-8.14 (m, 1H). MS (ES+) m/z 497.5 [M+H].

Example 9

7-(3,4-Difluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine

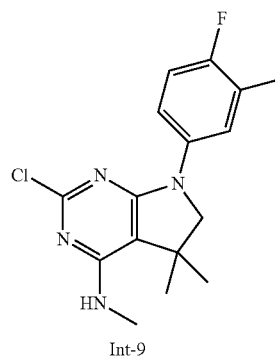

Int-9

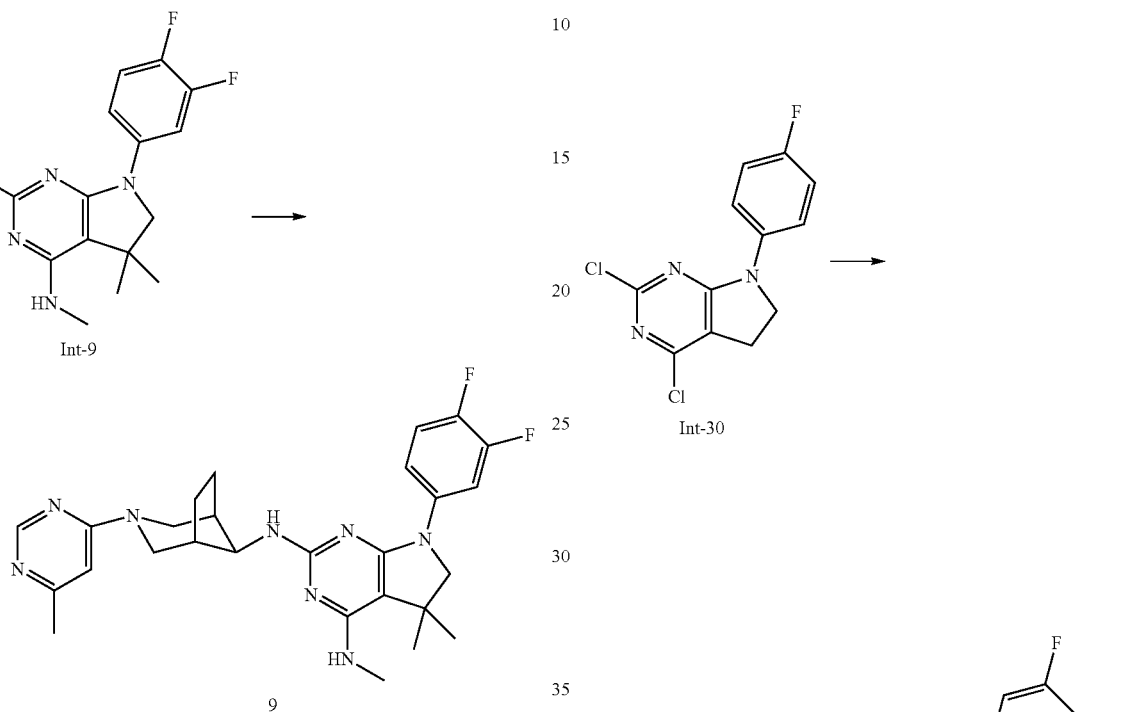

9

In a 2 mL microwave vial, 2-chloro-7-(3,4-difluorophenyl)-N,5,5-trimethyl-6,7-dihydro-5H-pyrrolo[2,3-d]pyrimidin-4-amine (Int-9, 60 mg, 185 μmol) was dissolved in NMP (1.2 mL) and (1R,5S,8s)-3-(6-methylpyrimidin-4-yl)-3-azabicyclo[3.2.1]octan-8-amine (65 mg, 298 μmol), cesium carbonate (125 mg, 384 μmol), 2-dicyclohexylphosphino-2'-(N,N-dimethyl-amino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a yellow foam (36 mg, 38%). HPLC (method LCMS_fastgradient) $t_R$=0.78 min. $^1$H NMR (CDCl$_3$, 300 MHz): δ 1.39 (s, 6H), 1.55-1.66 (m, 2H), 1.89-2.00 (m, 2H), 2.38 (s, 3H), 2.52-2.60 (m, 2H), 3.02 (d, J=4.8 Hz, 3H), 3.17 (d, J=12.5 Hz, 2H), 3.59 (s, 2H), 4.03-4.26 (m, 4H), 4.69 (d, J=5.0 Hz, 1H), 6.38 (s, 1H), 7.04-7.11 (m, 2H), 8.13 (br s, 1H), 8.53 (d, J=1.0 Hz, 1H). MS (ES+) m/z 507.3 [M+H].

Example 10

7-(4-Fluorophenyl)-N4-methyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine

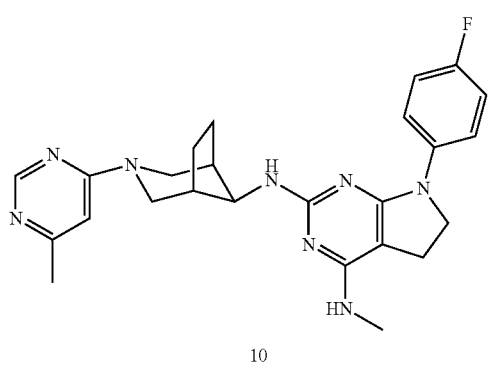

10

Step 1: 4-Chloro-7-(4-fluorophenyl)-N-((1R,5S,8s)-3-(6-methylpyrimidin-4-yl)-3-azabicyclo[3.2.1]octan-8-yl)-6,7-dihydro-5H-pyrrolo[2,3-d]pyrimidin-2-amine (Int-37)

In a screw-cap vial, 2,4-dichloro-7-(4-fluorophenyl)-6,7-dihydro-5H-pyrrolo[2,3-d]pyrimidine (Int-30, 90 mg, 317 μmol) was dissolved in ethanol (0.7 mL) and NMP (0.7 mL) and (1R,5S,8S)-3-(6-methylpyrimidin-4-yl)-3-azabicyclo[3.2.1]octan-8-amine (146 mg, 668 μmol) was added. The vial was flushed with Argon, closed and the mixture was stirred at 120° C. for 18 h. After cooling to room temperature, ethanol was distilled off, water (3 mL) was added and the mixture was extracted with tertbutylmethyl ether (TBME, 2×40 mL). The organic layers were washed with water (4×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to afford the title compound as an off-white solid (83 mg, 56%). HPLC (method LCMS_fastgradient) $t_R$=0.97 min. $^1$H NMR (CDCl$_3$, 300 MHz): δ 1.55-1.64 (m, 2H), 1.83-1.93 (m, 2H), 2.39 (s, 3H), 2.47-2.53 (m, 2H), 3.04-3.17 (m, 4H), 4.03-4.12 (m, 3H), 4.13-4.24 (m, 2H), 4.90-4.96 (m, 1H), 6.37 (s, 1H), 7.08 (dd, J=8.3, 9.3 Hz, 2H), 7.71-7.79 (m, 2H), 8.53 (s, 1H). MS (ES+) m/z 466.2, 468.2 [M+H, Cl isotopes].

Step 2: 7-(4-Fluorophenyl)-N4-methyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine (10)

In a screw-cap vial, 4-chloro-7-(4-fluorophenyl)-N-((1R,5S,8s)-3-(6-methylpyrimidin-4-yl)-3-azabicyclo[3.2.1]octan-8-yl)-6,7-dihydro-5H-pyrrolo[2,3-d]pyrimidin-2-amine (Int-37, 80 mg, 172 μmol) was suspended in ethanol (0.4 mL) and NMP (0.4 mL) and a solution of methylamine in ethanol (33% m/m, 302 mg, 0.4 mL, 3.21 mmol) was added. The vial was flushed with Argon and closed, the mixture was stirred at 110° C. for 18 h. Then a second portion of a solution of methylamine in ethanol (33% m/m, 302 mg, 0.4 mL, 3.21 mmol) was added. The vial was flushed again with Argon and closed, the mixture was stirred at 120° C. for 24 h. After cooling to room temperature, ethanol was distilled off, water (3 mL) was added and the mixture was extracted with tertbutylmethyl ether (TBME, 2×40 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as an off-white solid (34 mg, 41%). HPLC (method LCMS_fastgradient) $t_R$=1.41 min. $^1$H NMR (CDCl$_3$, 300 MHz): δ 1.55-1.63 (m, 2H), 1.90-1.98 (m, 2H), 2.38 (s, 3H), 2.51-2.57 (m, 2H), 2.86 (t, J=8.5 Hz, 2H), 3.02 (d, J=4.8 Hz, 3H), 3.11-3.19 (m, 2H), 3.94-4.02 (m, 3H), 4.08 (d, J=5.6 Hz, 1H), 4.10-4.23 (m, 2H), 4.61-4.67 (m, 1H), 6.38 (s, 1H), 7.02 (dd, J=8.4, 9.2 Hz, 2H), 7.67-7.76 (m, 2H), 8.53 (d, J=1.0 Hz, 1H). MS (ES+) m/z 461.2 [M+H].

Example 11

7-(3,4-Difluorophenyl)-N2-((1R,5S,8s)-3-(6-methoxypyridazin-4-yl)-3-azabicyclo[3.2.1]octan-8-yl)-N4,5,5-trimethyl-6,7-dihydro-5H-pyrrolo[2,3-d]pyrimidine-2,4-diamine

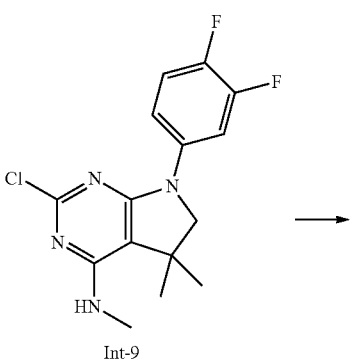

Int-9

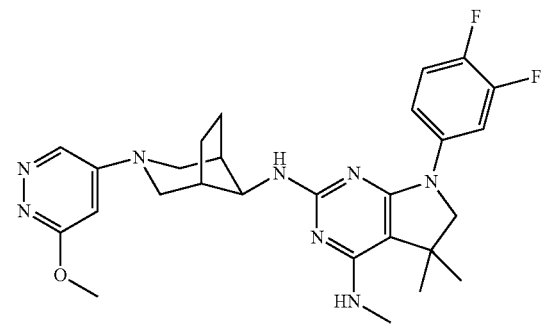

11

In a 2 mL microwave vial, 2-chloro-7-(3,4-difluorophenyl)-N,5,5-trimethyl-6,7-dihydro-5H-pyrrolo[2,3-d]pyrimidin-4-amine (Int-9, 60 mg, 185 μmol) was dissolved in NMP (1.2 mL) and (1R,5S,8s)-3-(6-methoxypyridazin-4-yl)-3-azabicyclo[3.2.1]octan-8-amine (65 mg, 277 μmol), cesium carbonate (120 mg, 368 μmol), 2-dicyclohexylphosphino-2'-(N,N-dimethyl-amino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to afford the title compound as an off-white foam (42 mg, 41%). HPLC (method LCMS_fastgradient) $t_R$=0.92 min. $^1$H NMR (CDCl$_3$, 300 MHz): δ 1.39 (s, 6H), 1.60-1.69 (m, 2H), 1.96-2.08 (m, 2H), 2.58-2.64 (m, 2H), 3.02 (d, J=4.8 Hz, 3H), 3.20 (d, J=11.5 Hz, 2H), 3.60 (s, 2H), 3.67 (dd, J=3.2, 11.7 Hz, 2H), 4.02-4.14 (m, 2H), 4.09 (s, 3H), 4.68 (d, J=5.4 Hz, 1H), 6.06 (d, J=2.6 Hz, 1H), 6.96-7.13 (m, 2H), 8.15 (br s, 1H), 8.60 (d, J=2.6 Hz, 1H). MS (ES+) m/z 523.4 [M+H].

Example 12

7-(4-Fluorophenyl)-N4,5,5-trimethyl-N2-((1R,5S,8s)-3-(pyridazin-4-yl)-3-azabicyclo[3.2.1]octan-8-yl)-6,7-dihydro-5H-pyrrolo[2,3-d]pyrimidine-2,4-diamine

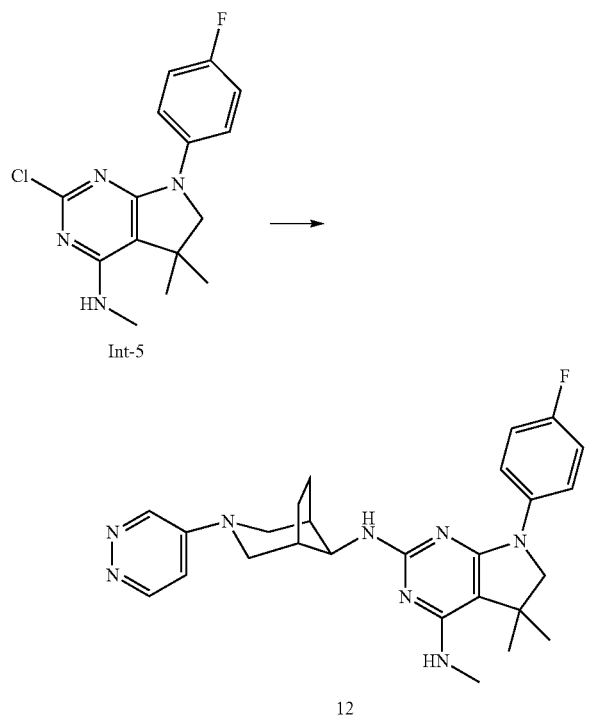

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 μmol) was dissolved in NMP (1.3 mL) and (1R,5S,8s)-3-(pyridazin-4-yl)-3-azabicyclo[3.2.1]octan-8-amine hydrochloride (60 mg, 249 μmol), cesium carbonate (200 mg, 614 μmol), 2-dicyclohexylphosphino-2'-(N,N-dimethyl-amino)biphenyl (16 mg, 41 μmol), and bis(dibenzylideneacetone)palladium(0) (20 mg, 35 μmol) were added subsequently. The vial was flushed with Argon and sealed. The reaction mixture was heated under microwave irradiation at 150° C. for 30 minutes. After that, second portions of 2-dicyclohexylphosphino-2'-(N,N-dimethyl-amino)biphenyl (16 mg, 41 μmol), and bis(dibenzylideneacetone)palladium(0) (20 mg, 35 μmol) were added and the mixture was stirred in an oil bath at 120° C. for 18 h. Then, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light yellow solid (16 mg, 16%). HPLC (method LCMS_fastgradient) $t_R$=0.76 min. $^1$H NMR (CDCl$_3$, 300 MHz): δ 1.39 (s, 6H), 1.58-1.68 (m, 2H), 1.98-2.07 (m, 2H), 2.59-2.66 (m, 2H), 3.02 (d, J=4.8 Hz, 3H), 3.16-3.23 (m, 2H), 3.62 (s, 2H), 3.72 (dd, J=3.0, 11.7 Hz, 2H), 4.04-4.12 (m, 2H), 4.65 (d, J=5.0 Hz, 1H), 6.63 (dd, J=3.4, 6.4 Hz, 1H), 7.01 (dd, J=8.4, 9.2 Hz, 2H), 7.66 (dd, J=4.7, 9.2 Hz, 2H), 8.70 (dd, J=0.7, 6.3 Hz, 1H), 8.85 (dd, J=0.6, 3.4 Hz, 1H). MS (ES+) m/z 475.2 [M+H].

Example 13

7-(3,3-Difluorocyclobutyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine

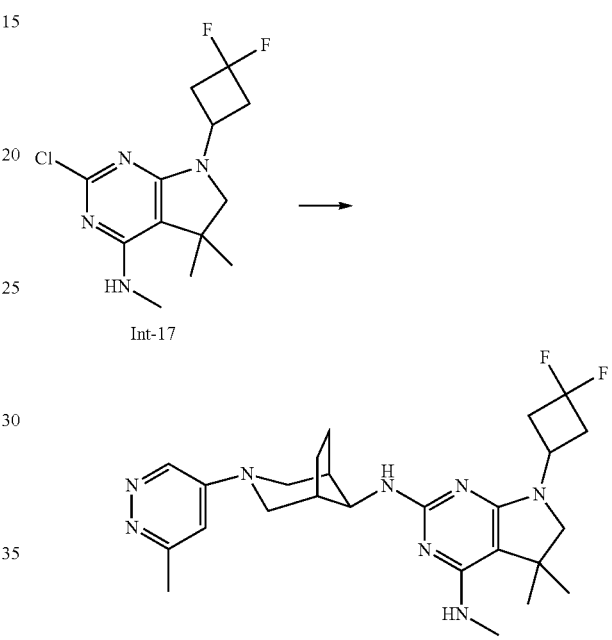

In a 2 mL microwave vial, 2-chloro-7-(3,3-difluorocyclobutyl)-N,5,5-trimethyl-6,7-dihydro-5H-pyrrolo[2,3-d]pyrimidin-4-amine (Int-17, 50 mg, 165 μmol) was dissolved in NMP (1.1 mL) and (1R,5S,8s)-3-(6-methylpyrimidin-4-yl)-3-azabicyclo[3.2.1]octan-8-amine (54 mg, 247 μmol), cesium carbonate (120 mg, 368 μmol), 2-dicyclohexylphosphino-2'-(N,N-dimethyl-amino)biphenyl (13 mg, 33 μmol), and bis(dibenzylideneacetone)palladium(0) (17 mg, 30 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light brown solid (31 mg, 39%). HPLC (method LCMS_fastgradient) $t_R$=0.74 min. $^1$H NMR (CDCl$_3$, 300 MHz): δ 1.30 (s, 6H), 1.52-1.61 (m, 2H), 1.87-1.98 (m, 2H), 2.37 (s, 3H), 2.45-2.52 (m, 2H), 2.73-2.94 (m, 4H), 2.97 (d, J=4.6 Hz, 3H), 3.08-3.16 (m, 4H), 3.90-3.99 (m, 2H), 4.03 (d, J=5.6 Hz, 1H), 4.25 (br s, 1H), 4.48-4.59 (m, 1H), 6.36 (s, 1H), 8.51 (d, J=0.8 Hz, 1H). MS (ES+) m/z 485.3 [M+H].

Example 14

7-(3,3-Difluorocyclobutyl)-N4,5,5-trimethyl-N2-((1R,5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine

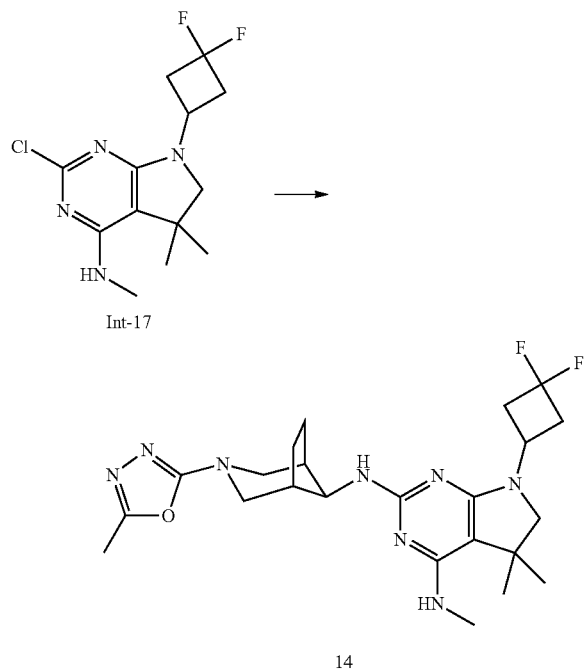

14

In a 2 mL microwave vial, 2-chloro-7-(3,3-difluorocyclobutyl)-N,5,5-trimethyl-6,7-dihydro-5H-pyrrolo[2,3-d]pyrimidin-4-amine (Int-17, 50 mg, 165 µmol) was dissolved in NMP (1.0 mL) and (1R,5S,8s)-3-(5-methyl-1,3,4-oxadiazol-2-yl)-3-azabicyclo[3.2.1]octan-8-amine (52 mg, 250 µmol), cesium carbonate (118 mg, 363 µmol), 2-dicyclohexylphosphino-2'-(N,N-dimethylamino)biphenyl (14 mg, 35.6 µmol), and bis(dibenzylideneacetone)palladium(0) (17 mg, 29.6 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford the title compound as an off-white foam (35 mg, 45%). HPLC (method LCMS_fastgradient) $t_R$=0.90 min. $^1$H NMR (CDCl$_3$, 300 MHz): δ 1.30 (s, 6H), 1.62-1.70 (m, 2H), 1.88-1.99 (m, 2H), 2.39 (s, 3H), 2.41-2.47 (m, 2H), 2.72-2.99 (m, 4H), 2.96 (d, J=4.8 Hz, 3H), 3.12 (s, 2H), 3.30 (d, J=11.7 Hz, 2H), 3.73 (dd, J=3.4, 12.3 Hz, 2H), 3.90-4.00 (m, 2H), 4.25 (br s, 1H), 4.50 (d, J=5.6 Hz, 1H). MS (ES+) m/z 475.3 [M+H].

Example 15

7-(2,4-Difluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine

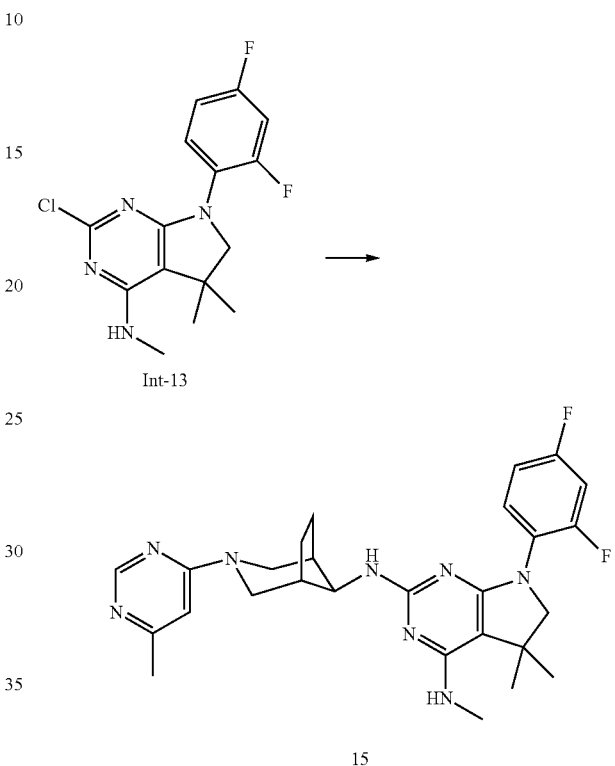

15

In a 2 mL microwave vial, 2-chloro-7-(2,4-difluorophenyl)-N,5,5-trimethyl-6,7-dihydro-5H-pyrrolo[2,3-d]pyrimidin-4-amine (Int-13, 55 mg, 169 µmol) was dissolved in NMP (1.1 mL) and (1R,5S,8s)-3-(6-methylpyrimidin-4-yl)-3-azabicyclo[3.2.1]octan-8-amine (56 mg, 257 µmol), cesium carbonate (120 mg, 368 µmol), 2-dicyclohexylphosphino-2'-(N,N-dimethyl-amino)biphenyl (14 mg, 35.6 µmol), and bis(dibenzylideneacetone)palladium(0) (18 mg, 31.3 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to afford the title compound as a light yellow foam (36 mg, 42%). HPLC (method LCMS_fastgradient) $t_R$=0.78 min. $^1$H NMR (CDCl$_3$, 300 MHz): δ 1.38 (s, 6H), 1.49-1.59 (m, 2H), 1.83-1.95 (m, 2H), 2.36 (s, 3H), 2.44-2.51 (m, 2H), 3.02 (d, J=4.8 Hz, 3H), 3.07 (d, J=12.5 Hz, 2H), 3.59 (d, J=1.0 Hz, 2H), 3.97-4.16 (m, 4H), 4.53-4.60 (m, 1H), 6.35 (s, 1H), 6.81-6.90 (m, 2H), 7.54-7.65 (m, 1H), 8.51 (d, J=0.8 Hz, 1H). MS (ES+) m/z 507.3 [M+H].

Example 16

7-(2,4-Difluorophenyl)-N4,5,5-trimethyl-N2-((1R,5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine

Example 17

N4,5,5-Trimethyl-N2-((1R,5S,8s)-3-(6-methylpyrimidin-4-yl)-3-azabicyclo[3.2.1]octan-8-yl)-7-(3-(trifluoromethyl)bicyclo[1.1.1]pentan-1-yl)-6,7-dihydro-5H-pyrrolo[2,3-d]pyrimidine-2,4-diamine

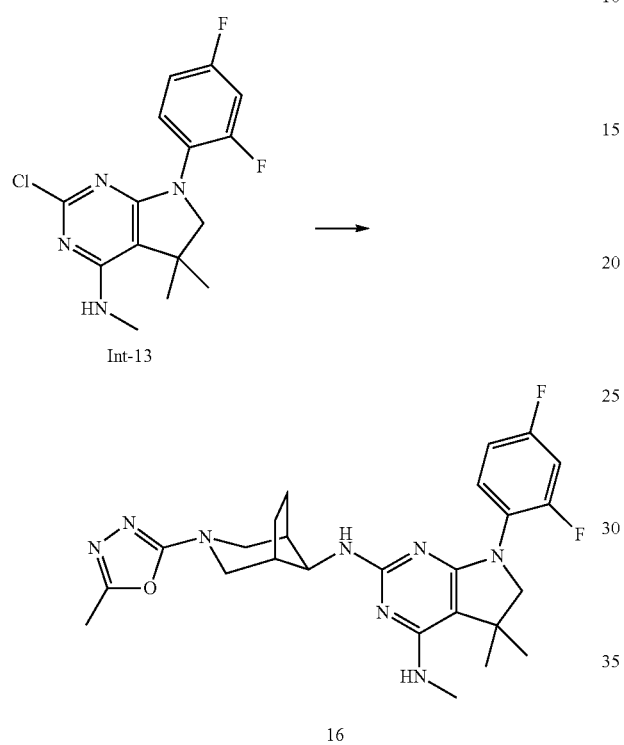

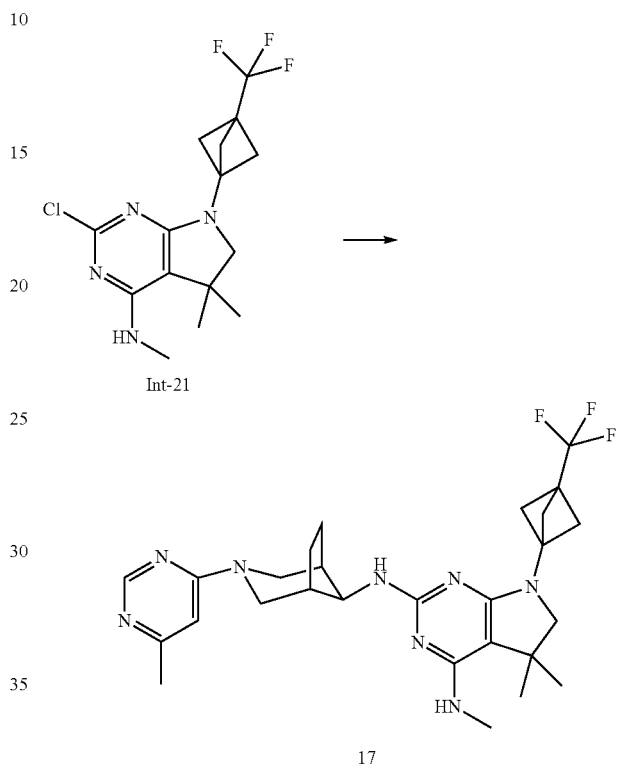

In a 2 mL microwave vial, 2-chloro-7-(2,4-difluorophenyl)-N,5,5-trimethyl-6,7-dihydro-5H-pyrrolo[2,3-d]pyrimidin-4-amine (Int-13, 60 mg, 185 μmol) was dissolved in NMP (1.2 mL) and (1R,5S,8s)-3-(5-methyl-1,3,4-oxadiazol-2-yl)-3-azabicyclo[3.2.1]octan-8-amine (58 mg, 278 μmol), cesium carbonate (130 mg, 399 μmol), 2-dicyclohexylphosphino-2'-(N,N-dimethyl-amino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to yield the title compound as a light yellow solid (44 mg, 46%). HPLC (method LCMS_fastgradient) $t_R$=0.93 min. $^1$H NMR (CDCl$_3$, 300 MHz): δ 1.38 (s, 6H), 1.58-1.68 (m, 2H), 1.87-1.95 (m, 2H), 2.39 (s, 3H), 2.40-2.46 (m, 2H), 3.01 (d, J=4.8 Hz, 3H), 3.25 (d, J=11.9 Hz, 2H), 3.59 (d, J=1.2 Hz, 2H), 3.71 (dd, J=3.3, 12.2 Hz, 2H), 3.92-3.97 (m, 1H), 4.04-4.12 (m, 1H), 4.53 (d, J=5.6 Hz, 1H), 6.80-6.90 (m, 2H), 7.53-7.63 (m, 1H). MS (ES+) m/z 497.3 [M+H].

In a 2 mL microwave vial, 2-chloro-N,5,5-trimethyl-7-(3-(trifluoromethyl)bicyclo-[1.1.1]pentan-1-yl)-6,7-dihydro-5H-pyrrolo[2,3-d]pyrimidin-4-amine (Int-21, 60 mg, 173 μmol) was dissolved in NMP (1.2 mL) and (1R,5S,8s)-3-(6-methylpyrimidin-4-yl)-3-azabicyclo[3.2.1]-octan-8-amine (57 mg, 261 μmol), cesium carbonate (124 mg, 381 μmol), 2-dicyclohexylphosphino-2'-(N,N-dimethylamino)biphenyl (14 mg, 36 μmol), and bis(dibenzylideneacetone)-palladium(0) (18 mg, 31 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light yellow foam (31 mg, 34%). HPLC (method LCMS_fastgradient) $t_R$=0.88 min. $^1$H NMR (CDCl$_3$, 300 MHz): δ 1.29 (s, 6H), 1.52-1.61 (m, 2H), 1.88-1.97 (m, 2H), 2.32 (s, 6H), 2.37 (s, 3H), 2.46-2.52 (m, 2H), 2.96 (d, J=4.8 Hz, 3H), 3.06-3.14 (m, 2H), 3.08 (s, 2H), 3.91-4.01 (m, 2H), 4.06-4.27 (m, 2H), 4.53 (d, J=5.0 Hz, 1H), 6.36 (s, 1H), 8.52 (d, J=0.8 Hz, 1H). MS (ES+) m/z 529.4 [M+H].

75

Example 18

N2-((1R,5S,8s)-3-(6-Methoxypyridazin-4-yl)-3-azabicyclo[3.2.1]octan-8-yl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine

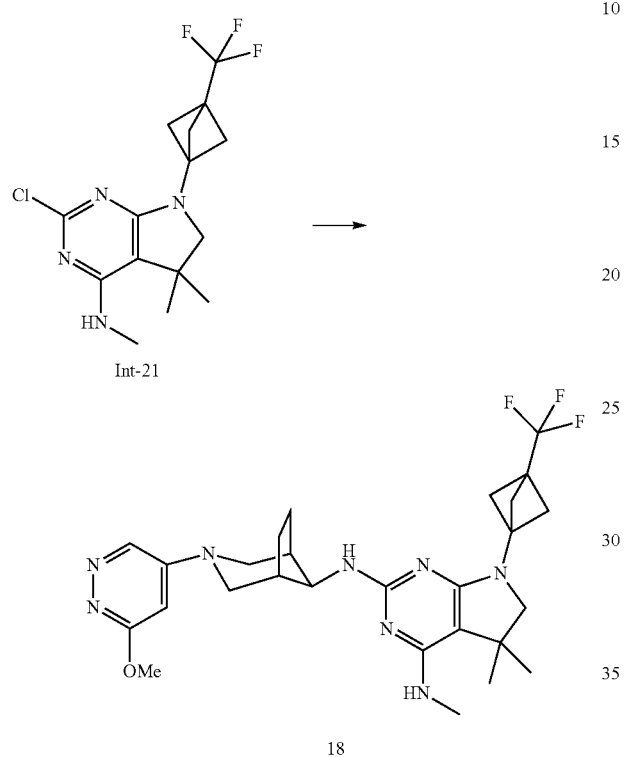

In a 2 mL microwave vial, 2-chloro-N,5,5-trimethyl-7-(3-(trifluoromethyl)bicycle-[1.1.1]pentan-1-yl)-6,7-dihydro-5H-pyrrolo[2,3-d]pyrimidin-4-amine (Int-21, 60 mg, 173 μmol) was dissolved in NMP (1.2 mL) and (1R,5S,8s)-3-(6-methoxypyridazin-4-yl)-3-azabicyclo[3.2.1]octan-8-amine (61 mg, 260 μmol), cesium carbonate (124 mg, 381 μmol), 2-dicyclohexylphosphino-2'-(N,N-dimethylamino)biphenyl (14 mg, 36 μmol), and bis(dibenzylideneacetone)palladium(0) (18 mg, 31 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light brown foam (21 mg, 22%). HPLC (method LCMS_fastgradient) $t_R$=0.95 min. $^1$H NMR (CDCl$_3$, 300 MHz): δ 1.29 (s, 6H), 1.58-1.65 (m, 2H), 1.94-2.04 (m, 2H), 2.32 (s, 6H), 2.50-2.57 (m, 2H), 2.96 (d, J=4.8 Hz, 3H), 3.08 (s, 2H), 3.09-3.16 (m, 2H), 3.65 (dd, J=3.0, 11.9 Hz, 2H), 3.92-3.98 (m, 2H), 4.08 (s, 3H), 4.52 (d, J=5.4 Hz, 1H), 6.03 (d, J=2.4 Hz, 1H), 8.58 (d, J=2.6 Hz, 1H). MS (ES+) m/z 545.4 [M+H].

76

Example 19

7-(2,4-Difluorophenyl)-N2-((1R,5S,8s)-3-(6-methoxypyridazin-4-yl)-3-azabicyclo[3.2.1]octan-8-yl)-N4,5,5-trimethyl-6,7-dihydro-5H-pyrrolo[2,3-d]pyrimidine-2,4-diamine In a 2 mL microwave vial, 2-chloro-7-(2,4-difluorophenyl)-N,5,5-trimethyl-6,7-dihydro-5H-pyrrolo[2,3-d]pyrimidin-4-amine (Int-5, 60 mg, 185 μmol) was dissolved in NMP (1.2 mL) and (1R,5S,8s)-3-(6-methoxypyridazin-4-yl)-3-azabicyclo[3.2.1]octan-8-amine (65 mg, 277 μmol), cesium carbonate (130 mg, 399 μmol), 2-dicyclohexylphosphino-2'-(N,N-dimethyl-amino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to afford the title compound as a light yellow foam (40 mg, 39%). HPLC (method LCMS_fastgradient) $t_R$=0.90 min. $^1$H NMR (CDCl$_3$, 300 MHz): δ 1.38 (s, 6H), 1.53-1.69 (m, 2H), 1.89-2.00 (m, 2H), 2.47-2.56 (m, 2H), 3.02 (d, J=4.8 Hz, 3H), 3.57-3.64 (m, 2H), 3.59 (d, J=1.0 Hz, 2H), 3.98 (d, J=5.4 Hz, 1H), 4.07-4.12 (m, 1H), 4.08 (s, 3H), 4.56 (d, J=5.4 Hz, 1H), 6.02 (d, J=2.6 Hz, 1H), 6.80-6.91 (m, 2H), 7.52-7.62 (m, 1H), 8.57 (d, J=2.4 Hz, 1H). MS (ES+) m/z 523.3 [M+H].

Example 20

2-((7-(4-Fluorophenyl)-5,5-dimethyl-2-(((1R,5S,8s)-3-(6-methylpyrimidin-4-yl)-3-azabicyclo[3.2.1]octan-8-yl)amino)-6,7-dihydro-5H-pyrrolo[2,3-d]pyrimidin-4-yl)amino)ethanol

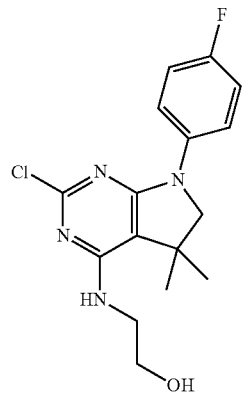

Int-23

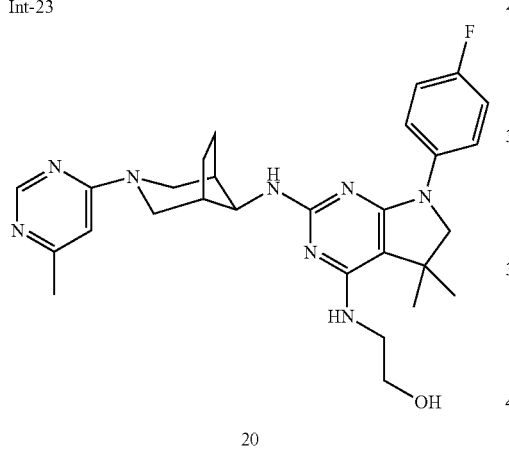

20

In a 2 mL microwave vial, 2-((2-chloro-7-(4-fluorophenyl)-5,5-dimethyl-6,7-dihydro-5H-pyrrolo[2,3-d]pyrimidin-4-yl)amino)ethanol (Int-23, 60 mg, 178 μmol) was dissolved in NMP (1.2 mL) and (1R,5S,8s)-3-(6-methylpyrimidin-4-yl)-3-azabicyclo[3.2.1]octan-8-amine (59 mg, 270 μmol), cesium carbonate (130 mg, 399 μmol), 2-dicyclohexylphosphino-2'-(N,N-dimethyl-amino)biphenyl (14 mg, 36 μmol), and bis(dibenzylideneacetone)palladium(0) (18 mg, 31 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to afford the title compound as a light brown foam (26 mg, 28%). HPLC (method LCMS_fastgradient) $t_R$=0.82 min. $^1$H NMR (CDCl$_3$, 300 MHz): δ 1.41 (s, 6H), 1.56-1.62 (m, 2H), 1.87-1.95 (m, 2H), 2.37 (s, 3H), 2.48-2.53 (m, 2H), 3.17 (d, J=12.5 Hz, 2H), 3.58-3.66 (m, 2H), 3.65 (s, 2H), 3.77-3.82 (m, 2H), 4.00 (d, J=5.8 Hz, 1H), 4.07-4.22 (m, 1H), 4.57-4.67 (m, 2H), 5.23 (br s, 1H), 6.37 (br s, 1H), 7.03 (dd, J=8.4, 9.2 Hz, 2H), 7.60-7.69 (m, 2H), 8.52 (d, J=0.8 Hz, 1H). MS (ES+) m/z 519.4 [M+H].

Example 21

2-((7-(4-Fluorophenyl)-2-(((1R,5S,8s)-3-(6-methoxypyridazin-4-yl)-3-azabicyclo[3.2.1]octan-8-yl)amino)-5,5-dimethyl-6,7-dihydro-5H-pyrrolo[2,3-d]pyrimidin-4-yl)amino)ethanol

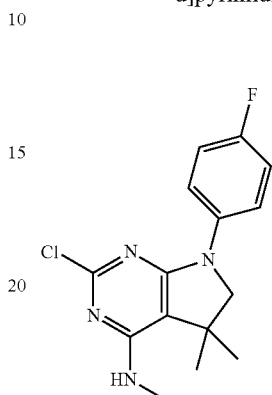

Int-23

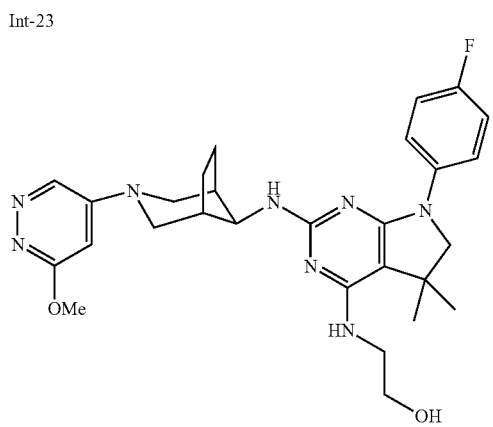

21

In a 2 mL microwave vial, 2-((2-chloro-7-(4-fluorophenyl)-5,5-dimethyl-6,7-dihydro-5H-pyrrolo[2,3-d]pyrimidin-4-yl)amino)ethanol (Int-23, 60 mg, 178 μmol) was dissolved in NMP (1.2 mL) and (1R,5S,8s)-3-(6-methoxypyridazin-4-yl)-3-azabicyclo[3.2.1]octan-8-amine (63 mg, 269 μmol), cesium carbonate (130 mg, 399 μmol), 2-dicyclohexylphosphino-2'-(N,N-dimethyl-amino)biphenyl (14 mg, 36 μmol), and bis(dibenzylideneacetone)palladium(0) (18 mg, 31 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to afford the title compound as a brown solid (19 mg, 20%). HPLC (method LCMS_fastgradient) $t_R$=0.85 min. $^1$H NMR (CDCl$_3$, 300 MHz): δ 1.41 (s, 6H), 1.59-1.68 (m, 2H), 1.92-2.01 (m, 2H), 2.51-2.57 (m, 2H), 3.20 (d, J=11.1 Hz, 2H), 3.59-3.68 (m, 6H), 3.79 (dd, J=3.7, 5.3 Hz, 2H), 3.98 (d, J=5.8 Hz, 1H), 4.08 (s, 3H), 4.57-4.67 (m, 2H), 5.25 (br s, 1H), 6.04 (d, J=2.4 Hz, 1H), 7.02 (dd, J=8.3, 9.1 Hz, 2H), 7.59-7.66 (m, 2H), 8.59 (d, J=2.6 Hz, 1H). MS (ES+) m/z 535.2 [M+H].

Example 22

8-(4-Fluorophenyl)-N4,5,5-trimethyl-N2-((1R,5S,8s)-3-(6-methylpyrimidin-4-yl)-3-azabicyclo[3.2.1]octan-8-yl)-5,6,7,8-tetrahydropyrido[2,3-d]pyrimidine-2,4-diamine

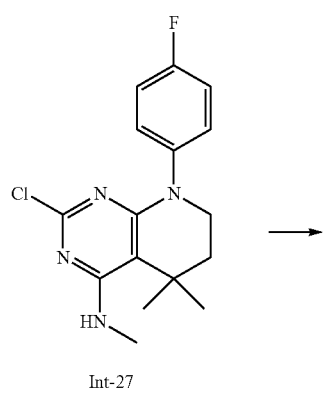

Int-27

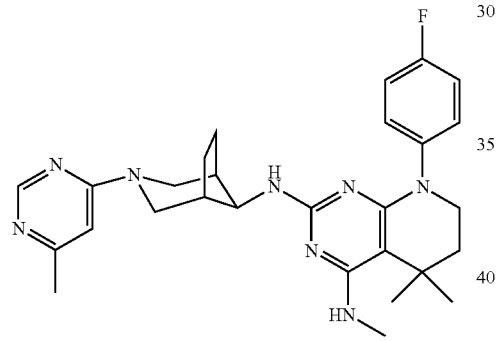

22

In a 2 mL microwave vial, 2-chloro-8-(4-fluorophenyl)-N,5,5-trimethyl-5,6,7,8-tetrahydropyrido[2,3-d]pyrimidin-4-amine (Int-27, 50 mg, 156 μmol) was suspended in NMP (1.0 mL) and (1R,5S,8S)-3-(6-methylpyrimidin-4-yl)-3-azabicyclo[3.2.1]octan-8-amine (40 mg, 183 μmol), cesium carbonate (112 mg, 343 μmol), 2-dicyclohexylphosphino-2'-(N,N-dimethyl-amino)biphenyl (13 mg, 33 μmol), and bis(dibenzylideneacetone)palladium(0) (16 mg, 27.8 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford the title compound as an off-white foam (33 mg, 42%). HPLC (method LCMS_fast-gradient) $t_R$=0.83 min. $^1$H NMR (CDCl$_3$, 300 MHz): δ 1.38 (s, 6H), 1.41-1.50 (m, 2H), 1.78-1.92 (m, 4H), 2.25-2.33 (m, 2H), 2.36 (s, 3H), 2.78-2.90 (m, 2H), 2.99 (d, J=4.4 Hz, 3H), 3.54-3.63 (m, 2H), 3.67 (br s, 1H), 3.89-4.09 (m, 2H), 4.22-4.48 (m, 2H), 6.30 (s, 1H), 6.97-7.06 (m, 2H), 7.18-7.25 (m, 2H), 8.50 (d, J=1.0 Hz, 1H). MS (ES+) m/z 503.4 [M+H].

Example 23

8-(4-Fluorophenyl)-N2-((1R,5S,8s)-3-(6-methoxypyridazin-4-yl)-3-azabicyclo[3.2.1]octan-8-yl)-N4,5,5-trimethyl-5,6,7,8-tetrahydropyrido[2,3-d]pyrimidine-2,4-diamine

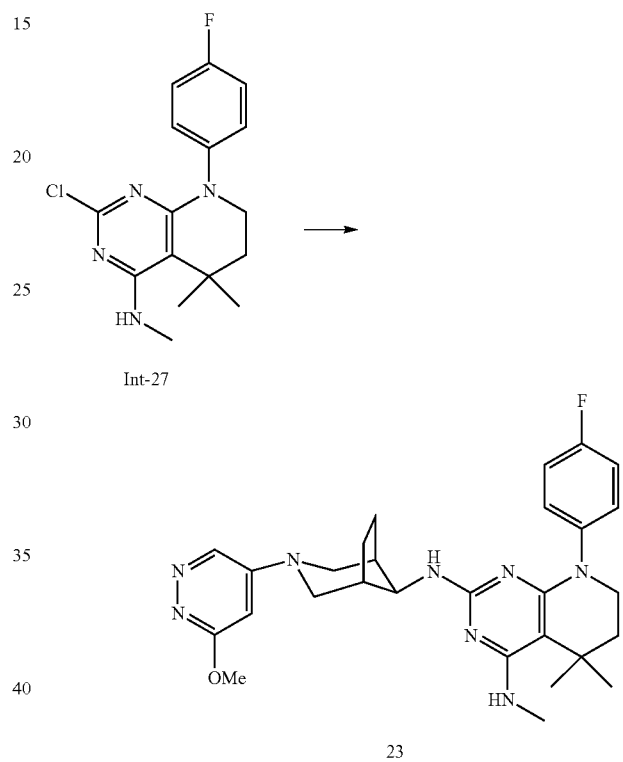

In a 2 mL microwave vial, 2-chloro-8-(4-fluorophenyl)-N,5,5-trimethyl-5,6,7,8-tetrahydropyrido[2,3-d]pyrimidin-4-amine (Int-27, 90 mg, 281 μmol) was suspended in NMP (1.8 mL) and (1R,5S,8S)-3-(6-methoxypyridazin-4-yl)-3-azabicyclo[3.2.1]octan-8-amine (80 mg, 341 μmol), cesium carbonate (200 mg, 614 μmol), 2-dicyclohexylphosphino-2'-(N,N-dimethylamino)biphenyl (22 mg, 56 μmol), and bis(dibenzylideneacetone)palladium(0) (29 mg, 50.5 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 24 g, eluting with methanol/dichloromethane, gradient 0:100 to 5:95) to yield the title compound as an off-white solid (31 mg, 21%). HPLC (method LCMS_fast-gradient) $t_R$=0.87 min. $^1$H NMR (CDCl$_3$, 300 MHz): δ 1.38 (s, 6H), 1.44-1.54 (m, 2H), 1.84-1.94 (m, 4H), 2.28-2.37 (m, 2H), 2.79-2.89 (m, 2H), 2.99 (d, J=4.6 Hz, 3H), 3.47 (dd, J=2.5, 11.6 Hz, 2H), 3.54-3.66 (m, 3H), 4.08 (s, 3H), 4.26 (d, J=4.8 Hz, 1H), 4.39-4.47 (m, 1H), 5.97 (d, J=2.4 Hz, 1H), 6.96-7.05 (m, 2H), 7.16-7.23 (m, 2H), 8.53 (d, J=2.6 Hz, 1H). MS (ES+) m/z 519.3 [M+H].

Example 24

7-(2,3-Difluorophenyl)-N4,5,5-trimethyl-N2-((1R, 5S,8s)-3-(6-methylpyrimidin-4-yl)-3-azabicyclo [3.2.1]octan-8-yl)-6,7-dihydro-5H-pyrrolo[2,3-d] pyrimidine-2,4-diamine

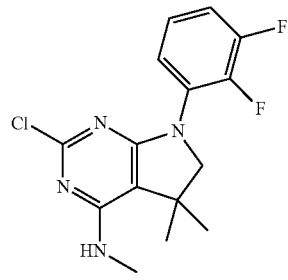

Int-38

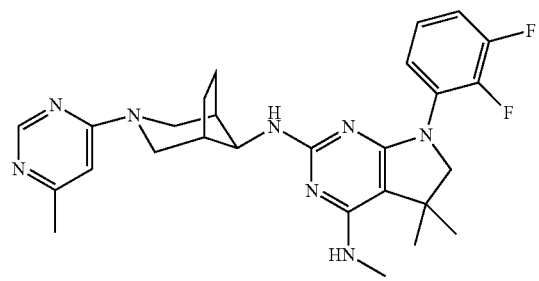

24

In a 2 mL microwave vial, 2-chloro-7-(2,3-difluorophenyl)-N,5,5-trimethyl-6,7-dihydro-5H-pyrrolo[2,3-d]pyrimidin-4-amine (Int-38, 60 mg, 185 μmol) was dissolved in NMP (1.2 mL) and (1R,5S,8s)-3-(6-methylpyrimidin-4-yl)-3-azabicyclo[3.2.1]octan-8-amine (57 mg, 261 μmol), cesium carbonate (140 mg, 430 μmol), 2-dicyclohexylphosphino-2'-(N,N-dimethyl-amino)biphenyl (15 mg, 38.1 μmol), and bis(dibenzylideneacetone)palladium(0) (19 mg, 33.0 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford the title compound as a light yellow foam (22 mg, 22%). HPLC (method LCMS_fastgradient) $t_R$=0.81 min. $^1$H NMR (CDCl$_3$, 300 MHz): δ 1.39 (s, 6H), 1.50-1.59 (m, 2H), 1.85-1.94 (m, 2H), 2.37 (s, 3H), 2.46-2.52 (m, 2H), 3.03 (d, J=4.8 Hz, 3H), 3.04-3.12 (m, 2H), 3.69 (d, J=1.8 Hz, 2H), 3.99-4.17 (m, 4H), 4.60 (d, J=5.4 Hz, 1H), 6.35 (s, 1H), 6.85-6.95 (m, 1H), 6.97-7.06 (m, 1H), 7.44-7.52 (m, 1H), 8.51 (d, J=0.8 Hz, 1H). MS (ES+) m/z 507.4 [M+H].

Example 25p (S)- or (R)-7-(4-Fluorophenyl)-N4,5-dimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine

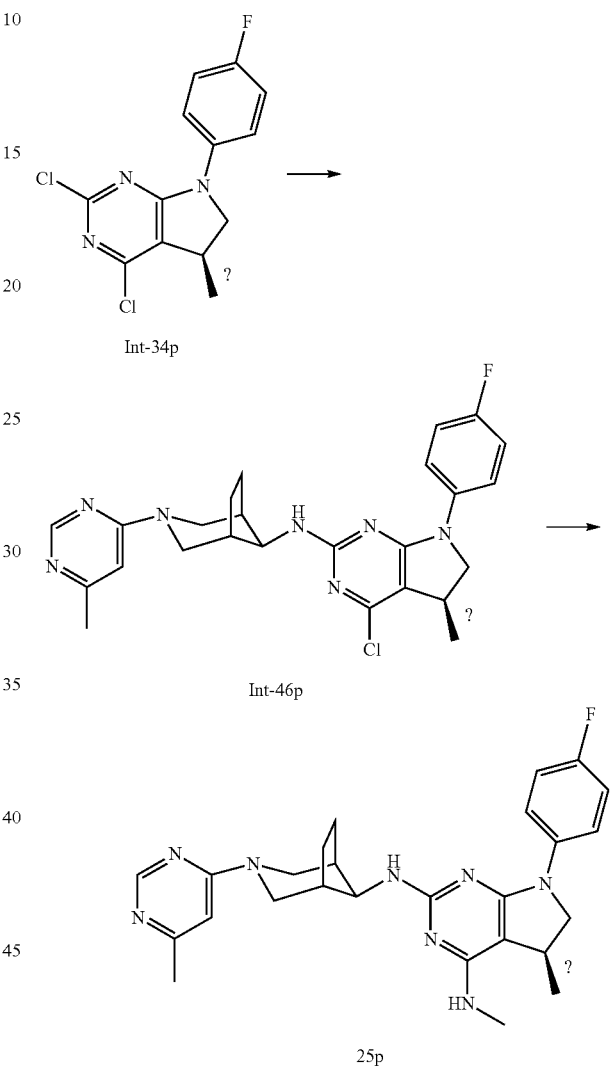

Step 1: (S)- or (R)-4-Chloro-7-(4-fluorophenyl)-5-methyl-N-((1R,5S,8s)-3-(6-methylpyrimidin-4-yl)-3-azabicyclo[3.2.1]octan-8-yl)-6,7-dihydro-5H-pyrrolo [2,3-d]pyrimidin-2-amine (Int-46p)

In a screw-cap vial, (−)-2,4-dichloro-7-(4-fluorophenyl)-5-methyl-6,7-dihydro-5H-pyrrolo[2,3-d]pyrimidine (Int-34 p, 35 mg, 117 μmol) was dissolved in NMP (1.3 mL) and (1R,5 S,8S)-3-(6-methylpyrimidin-4-yl)-3-azabicyclo[3.2. 1]octan-8-amine (33.3 mg, 153 μmol), followed by diisopropylethylamine (27.3 mg, 211 μmol) were added. The vial was flushed with Argon, closed and the mixture was stirred at 130° C. for 16 h. After cooling to room temperature, water (10 mL) was added and the mixture was extracted with tertbutylmethyl ether (TBME, 2×30 mL). The organic layers were washed with water (1×20 mL) and brine (1×20 mL), combined, dried (sodium sulfate) and concentrated in vacuo. The crude product was purified by column chromatography (silica gel, 12 g, eluting with methanol/dichloromethane, gradient 0:100 to 10:90) to afford the title compound a light brown foam (58 mg, 93%). HPLC (method LCMS_fastgradient) $t_R$=1.05 min. MS (ES+) m/z 480.8, 482.8 [M+H, Cl isotopes].

Step 2: (S)- or (R)-7-(4-Fluorophenyl)-N4,5-dimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine (25p)

In a screw-cap vial, (S)- or (R)-4-chloro-7-(4-fluorophenyl)-5-methyl-N-((1R,5S,8s)-3-(6-methylpyrimidin-4-yl)-3-azabicyclo[3.2.1]octan-8-yl)-6,7-dihydro-5H-pyrrolo[2,3-d]pyrimidin-2-amine (Int-46p, 58 mg, 121 µmol) was suspended in NMP (0.5 mL) and a solution of methylamine in ethanol (33% m/m, 752 µL, 6.04 mmol) was added. The vial was flushed with Argon and closed, the mixture was stirred at 120° C. for 48 h. After cooling to room temperature, water (10 mL) was added and the mixture was extracted with tertbutylmethyl ether (TBME, 2×30 mL). The organic layers were washed with water (1×20 mL) and brine (1×20 mL), combined, dried (sodium sulfate) and concentrated in vacuo. The crude product was purified by column chromatography (silica gel, 12 g, eluting with methanol/dichloromethane, gradient 0:100 to 10:90) to yield the title compound as an off-white foam (48 mg, 79%). HPLC (method LCMS_fastgradient) $t_R$=0.81 min. $^1$H NMR (CDCl$_3$, 300 MHz): δ 1.27 (d, J=6.6 Hz, 3H), 1.53-1.63 (m, 2H), 1.88-1.99 (m, 3H), 2.38 (s, 3H), 2.50-2.60 (m, 2H), 3.02 (d, J=5.0 Hz, 3H), 3.10-3.19 (m, 2H), 3.20-3.30 (m, 1H), 3.48 (dd, J=3.9, 9.6 Hz, 1H), 3.98-4.26 (m, 4H), 4.64-4.71 (m, 1H), 6.38 (s, 1H), 7.02 (dd, J=8.5, 9.1 Hz, 2H), 7.65-7.75 (m, 2H), 8.53 (d, J=0.8 Hz, 1H). MS (ES+) m/z 475.8 [M+H].

Example 25q (R)- or (S)-7-(4-Fluorophenyl)-N4,5-dimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine

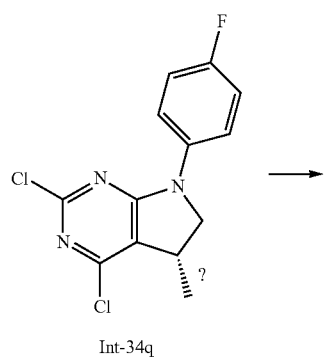

Int-34q

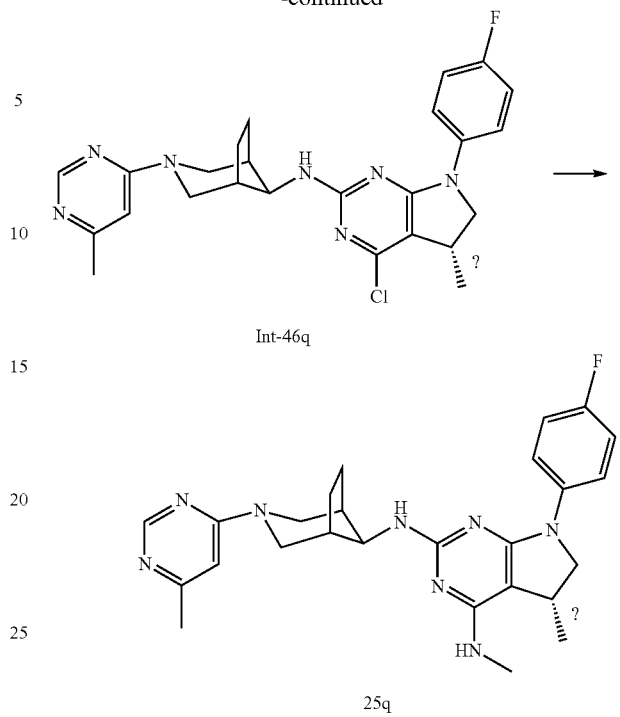

Step 1: (R)- or (S)-4-Chloro-7-(4-fluorophenyl)-5-methyl-N-((1R,5S,8s)-3-(6-methylpyrimidin-4-yl)-3-azabicyclo[3.2.1]octan-8-yl)-6,7-dihydro-5H-pyrrolo[2,3-d]pyrimidin-2-amine (Int-46q)

In a screw-cap vial, (+)-2,4-dichloro-7-(4-fluorophenyl)-5-methyl-6,7-dihydro-5H-pyrrolo[2,3-d]pyrimidine (Int-34 q, 36 mg, 121 µmol) was dissolved in NMP (1.3 mL) and (1R,5 S,8S)-3-(6-methylpyrimidin-4-yl)-3-azabicyclo[3.2.1]octan-8-amine (34.3 mg, 157 µmol), followed by diisopropylethylamine (28.1 mg, 217 µmol) were added. The vial was flushed with Argon, closed and the mixture was stirred at 130° C. for 16 h. After cooling to room temperature, water (10 mL) was added and the mixture was extracted with tertbutylmethyl ether (TBME, 2×30 mL). The organic layers were washed with water (1×20 mL) and brine (1×20 mL), combined, dried (sodium sulfate) and concentrated in vacuo. The crude product was purified by column chromatography (silica gel, 12 g, eluting with methanol/dichloromethane, gradient 0:100 to 10:90) to afford the title compound a light brown foam (56 mg, 97%). HPLC (method LCMS_fastgradient) $t_R$=1.05 min. MS (ES+) m/z 480.8, 482.8 [M+H, Cl isotopes].

Step 2: (R)- or (S)-7-(4-Fluorophenyl)-N4,5-dimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine (25q)

In a screw-cap vial, (R)- or (S)-4-chloro-7-(4-fluorophenyl)-5-methyl-N-((1R,5S,8s)-3-(6-methylpyrimidin-4-yl)-3-azabicyclo[3.2.1]octan-8-yl)-6,7-dihydro-5H-pyrrolo[2,3-d]pyrimidin-2-amine (Int-46q, 56 mg, 117 µmol) was suspended in NMP (0.5 mL) and a solution of methylamine in ethanol (33% m/m, 549 mg, 726 µL, 5.83 mmol) was added. The vial was flushed with Argon and closed, the mixture was stirred at 120° C. for 48 h. After cooling to room temperature, water (10 mL) was added and the mixture was extracted with tertbutylmethyl ether (TBME, 2×30 mL). The organic layers were washed with water (1×20 mL) and brine (1×20 mL), combined, dried (sodium sulfate) and concentrated in vacuo. The crude product was purified by column chromatography (silica gel, 12 g, eluting with methanol/dichloromethane, gradient 0:100 to 10:90) to yield the title compound as an off-white foam (41 mg, 74%). HPLC (method LCMS_fastgradient) $t_R$=0.79 min. $^1$H NMR (CDCl$_3$, 300 MHz): δ 1.27 (d, J=6.6 Hz, 3H), 1.53-1.63 (m, 2H), 1.88-1.99 (m, 3H), 2.38 (s, 3H), 2.50-2.60 (m, 2H), 3.02 (d, J=5.0 Hz, 3H), 3.10-3.19 (m, 2H), 3.20-3.30 (m, 1H), 3.48 (dd, J=3.9, 9.6 Hz, 1H), 3.98-4.26 (m, 4H), 4.64-4.71 (m, 1H), 6.38 (s, 1H), 7.02 (dd, J=8.5, 9.1 Hz, 2H), 7.65-7.75 (m, 2H), 8.53 (d, J=0.8 Hz, 1H). MS (ES+) m/z 475.9 [M+H].

Example 26

7-(2,3-Difluorophenyl)-N4,5,5-trimethyl-N2-((1R, 5S,8s)-3-(6-methoxypyridazin-4-yl)-3-azabicyclo [3.2.1]octan-8-yl)-6,7-dihydro-5H-pyrrolo[2,3-d] pyrimidine-2,4-diamine

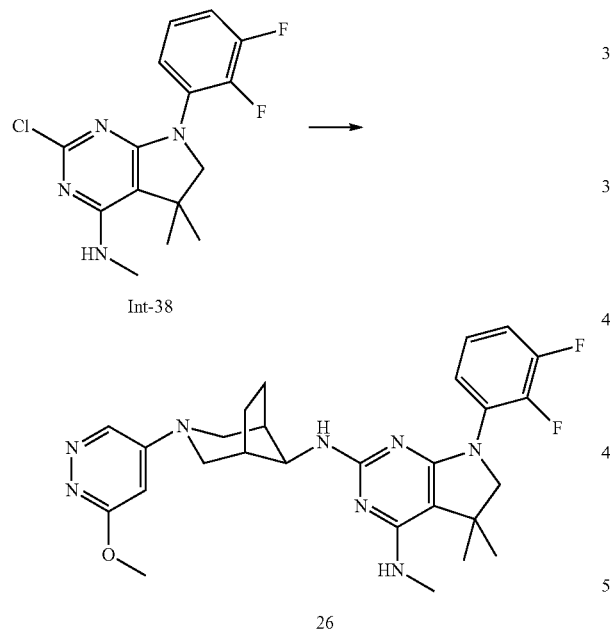

In a 2 mL microwave vial, 2-chloro-7-(2,3-difluorophenyl)-N,5,5-trimethyl-6,7-dihydro-5H-pyrrolo[2,3-d]pyrimidin-4-amine (Int-38, 60 mg, 185 μmol) was dissolved in NMP (1.2 mL) and (1R,5S,8s)-3-(6-methoxypyridazin-4-yl)-3-azabicyclo[3.2.1]octan-8-amine (65 mg, 277 μmol), cesium carbonate (126 mg, 388 μmol), 2-dicyclohexylphosphino-2'-(N,N-dimethyl-amino)biphenyl (15 mg, 38.1 μmol), and bis(dibenzylideneacetone)palladium(0) (19 mg, 33.0 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford the title compound as an off-white solid (23 mg, 24%). HPLC (method LCMS_fastgradient) $t_R$=0.89 min. $^1$H NMR (CDCl$_3$, 300 MHz): δ 1.39 (s, 6H), 1.54-1.64 (m, 2H), 1.91-2.01 (m, 2H), 2.50-2.57 (m, 2H), 3.02 (d, J=4.8 Hz, 3H), 3.06-3.14 (m, 2H), 3.61 (dd, J=3.0, 11.7 Hz, 2H), 3.68 (d, J=1.6 Hz, 2H), 3.95-4.01 (m, 1H), 4.08 (s, 3H), 4.08-4.15 (m, 1H), 4.60 (d, J=5.4 Hz, 1H), 6.02 (d, J=2.6 Hz, 1H), 6.86-7.05 (m, 2H), 7.41-7.49 (m, 1H), 8.57 (d, J=2.6 Hz, 1H). MS (ES+) m/z 523.3 [M+H].

Example 27

7-(2,3-Difluorophenyl)-N4,5,5-trimethyl-N2-((1R, 5S,8s)-3-(2-methoxypyridin-4-yl)-3-azabicyclo [3.2.1]octan-8-yl)-6,7-dihydro-5H-pyrrolo[2,3-d] pyrimidine-2,4-diamine

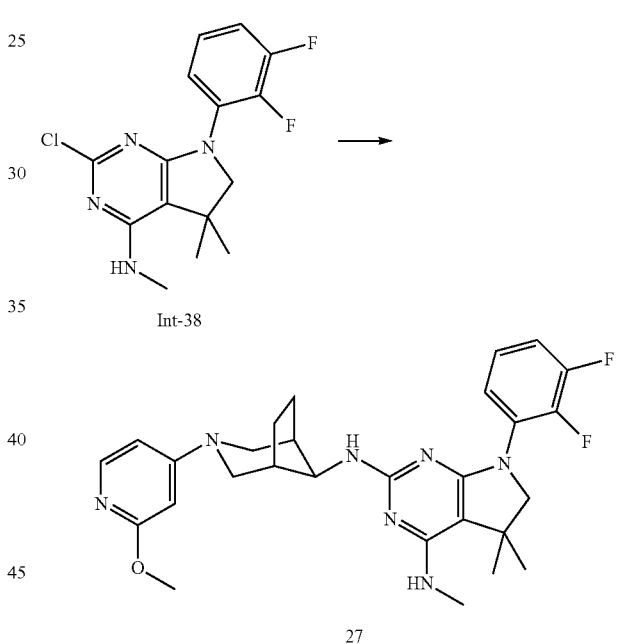

In a 2 mL microwave vial, 2-chloro-7-(2,3-difluorophenyl)-N,5,5-trimethyl-6,7-dihydro-5H-pyrrolo[2,3-d]pyrimidin-4-amine (Int-38, 52 mg, 160 μmol) was dissolved in NMP (1.1 mL) and (1R,5S,8s)-3-(2-methoxypyridin-4-yl)-3-azabicyclo[3.2.1]octan-8-amine (49 mg, 210 μmol), cesium carbonate (110 mg, 336 μmol), 2-dicyclohexylphosphino-2'-(N,N-dimethyl-amino)biphenyl (13 mg, 33 μmol), and bis(dibenzylideneacetone)palladium(0) (16 mg, 28 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95), followed by preparative HPLC (Gemini NX, 50×4.6 mm×3 μm, flow 1.4 mL/min, eluting with acetonitrile/(water+0.1% triethylamine), gradient 20:80 to 98:2 v/v) to afford the title compound as an off-white solid (13 mg, 16%). HPLC (method LCMS_fast-gradient) $t_R$=0.81 min. $^1$H NMR (CDCl$_3$, 300 MHz): δ 1.38 (s, 6H), 1.57-1.65 (m, 2H), 1.89-1.96 (m, 2H), 2.46-2.52 (m, 2H), 2.99-3.07 (m, 5H), 3.58 (dd, J=3.1, 11.8 Hz, 2H), 3.69 (d, J=1.8 Hz, 2H), 3.90 (s, 3H), 3.94-3.99 (m, 1H), 4.07-4.15 (m, 1H), 4.60 (d, J=5.0 Hz, 1H), 5.99 (d, J=2.2 Hz, 1H), 6.35 (dd, J=2.3, 6.1 Hz, 1H), 6.85-7.05 (m, 2H), 7.44-7.52 (m, 1H), 7.86 (d, J=6.2 Hz, 1H). MS (ES+) m/z 522.5 [M+H].

The invention claimed is:

1. A compound of formula I,

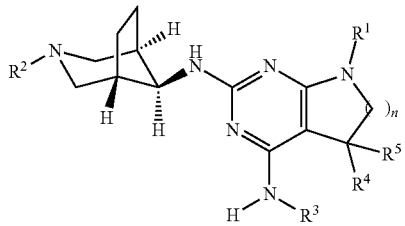

I wherein:

$R^1$ is phenyl, lower alkyl, $C_{3-6}$-cycloalkyl, —CH$_2$—$C_{3-6}$-cycloalkyl or bridged $C_{4-7}$-cycloalkyl, substituted by one, two or three halogen atoms, lower alkyl, or lower alkyl substituted by halogen;

$R^2$ is a substituted heteroaryl group, selected from

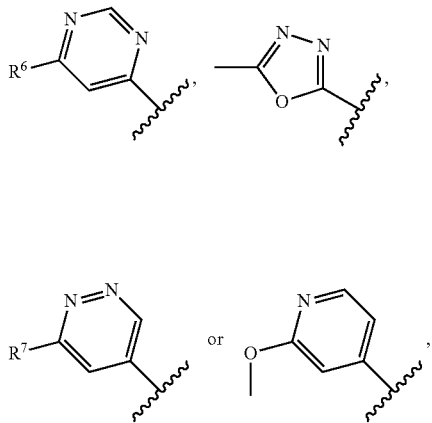

wherein:

$R^6$ is hydrogen, lower alkyl, halogen, or lower alkoxy; and $R^7$ is hydrogen, lower alkoxy, or halogen;

$R^3$ is lower alkyl, or lower alkyl substituted by hydroxy:

$R^4$ is hydrogen or lower alkyl;

$R^5$ is hydrogen or lower alkyl;

n is 1 or 2; and

-( )$_n$- is —CH$_2$— or —CH$_2$CH$_2$— when n is 1 or 2;

or an enantiomer, or a pharmaceutically acceptable salt thereof.

2. A compound of formula I-1,

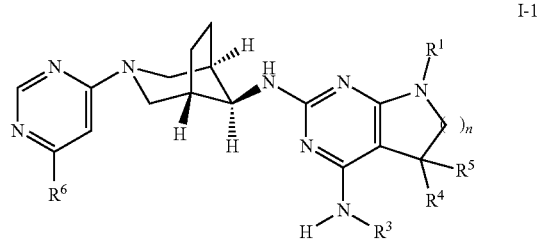

I-1 wherein:

$R^1$ is phenyl, lower alkyl, $C_{3-6}$-cycloalkyl, —CH$_2$—$C_{3-6}$-cycloalkyl or bridged $C_{4-7}$-cycloalkyl, substituted by one, two or three halogen atoms, lower alkyl, or lower alkyl substituted by halogen;

$R^3$ is lower alkyl or lower alkyl substituted by hydroxy:

$R^4$ is hydrogen or lower alkyl;

$R^5$ is hydrogen or lower alkyl;

$R^6$ is hydrogen, lower alkyl, halogen, or lower alkoxy; and n is 1 or 2; and

-( )$_n$- is —CH$_2$— or —CH$_2$CH$_2$— when n is 1 or 2;

or an enantiomer, or a pharmaceutically acceptable salt thereof.

3. A compound according to claim 2, or a pharmaceutically acceptable salt thereof, wherein the compound is selected from the group consisting of:

7-(4-Fluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine, N2-((1R,5S,8s)-3-(6-Chloropyrimidin-4-yl)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine, 7-(4-Fluorophenyl)-N2-((1R,5S,8s)-3-(6-methoxypyrimidin-4-yl)-3-azabicyclo[3.2.1]octan-8-yl)-N4,5,5-trimethyl-6,7-dihydro-5H-pyrrolo[2,3-d]pyrimidine-2,4-diamine, 7-(3,4-Difluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine, 7-(4-Fluorophenyl)-N4-methyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine, 7-(3,3-Difluorocyclobutyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine, 7-(2,4-Difluorophenyl)-N4,5,5-trimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine, N4,5,5-Trimethyl-N2-((1R,5S,8s)-3-(6-methylpyrimidin-4-yl)-3-azabicyclo[3.2.1]octan-8-yl)-7-(3-(trifluoromethyl)bicyclo[1.1.1]pentan-1-yl)-6,7-dihydro-5H-pyrrolo[2,3-d]pyrimidine-2,4-diamine, 2-((7-(4-Fluorophenyl)-5,5-dimethyl-2-(((1R,5S,8s)-3-(6-methylpyrimidin-4-yl)-3-azabicyclo[3.2.1]octan-8-yl)amino)-6,7-dihydro-5H-pyrrolo[2,3-d]pyrimidin-4-yl)amino)ethanol, 8-(4-Fluorophenyl)-N4,5,5-trimethyl-N2-((1R,5S,8s)-3-(6-methylpyrimidin-4-yl)-3-azabicyclo[3.2.1]octan-8-yl)-5,6,7,8-tetrahydropyrido[2,3-d]pyrimidine-2,4-diamine, 7-(2,3-Difluorophenyl)-N4,5,5-trimethyl-N2-((1R,5S, 8s)-3-(6-methylpyrimidin-4-yl)-3-azabicyclo[3.2.1]octan-8-yl)-6,7-dihydro-5H-pyrrolo[2,3-d]pyrimidine-2, 4-diamine, (R)-7-(4-Fluorophenyl)-N4,5-dimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine, and (S)-7-(4-Fluorophenyl)-N4,5-dimethyl-N2-((1R,5S,8s)-3-(6-methylpyrimidin-4-yl)-3-azabicyclo[3.2.1]octan-8-yl)-6,7-dihydro-5H-pyrrolo[2,3-d]pyrimidine-2,4-diamine.

4. A compound of formula I-2,

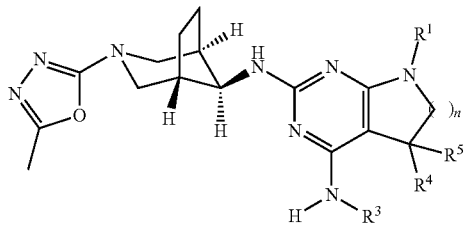

I-2 wherein:

R$^1$ is phenyl, lower alkyl, C$_{3-6}$-cycloalkyl, —CH$_2$—C$_{3-6}$-cycloalkyl or bridged C$_{4-7}$-cycloalkyl, substituted by one, two or three halogen atoms, lower alkyl, or lower alkyl substituted by halogen;

R$^3$ is lower alkyl or lower alkyl substituted by hydroxy;

R$^4$ is hydrogen or lower alkyl;

R$^5$ is hydrogen or lower alkyl;

n is 1 or 2;

-( )$_n$- is —CH$_2$— or —CH$_2$CH$_2$— when n is 1 or 2;

or an enantiomer, or a pharmaceutically acceptable salt thereof.

5. A compound according to claim 4, or a pharmaceutically acceptable salt thereof, wherein the compound is selected from the group consisting of:

7-(4-Fluorophenyl)-N4,5,5-trimethyl-N2-((1R,5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine, 7-(3,4-Difluorophenyl)-N4,5,5-trimethyl-N2-((1R,5S, 8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine, 7-(3,3-Difluorocyclobutyl)-N4,5,5-trimethyl-N2-((1R, 5S,8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine, and 7-(2,4-Difluorophenyl)-N4,5,5-trimethyl-N2-((1R,5S, 8s)-3-(5-methyl-1,3,4-oxadiazol-2-yl)-3-azabicyclo[3.2.1]octan-8-yl)-6,7-dihydro-5H-pyrrolo[2,3-d]pyrimidine-2,4-diamine.

6. A compound of formula I-3,

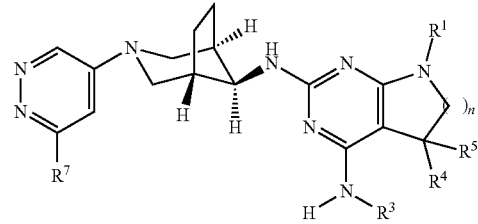

I-3 wherein:

R$^1$ is phenyl, lower alkyl, C$_{3-6}$-cycloalkyl, —CH$_2$—C$_{3-6}$-cycloalkyl or bridged C$_{4-7}$-cycloalkyl, substituted by one, two or three halogen atoms, lower alkyl, or lower alkyl substituted by halogen;

R$^3$ is lower alkyl or lower alkyl substituted by hydroxy;

R$^4$ is hydrogen or lower alkyl;

R$^5$ is hydrogen or lower alkyl;

R$^7$ is hydrogen, halogen or lower alkoxy; and n is 1 or 2;

-( )$_n$- is —CH$_2$— or —CH$_2$CH$_2$— when n is 1 or 2;

or an enantiomer, or a pharmaceutically acceptable salt thereof.

7. A compound according to claim 6, or a pharmaceutically acceptable salt thereof, wherein the compound is selected from the group consisting of:

7-(4-Fluorophenyl)-N2-((1R,5S,8s)-3-(6-methoxypyridazin-4-yl)-3-azabicyclo[3.2.1]octan-8-yl)-N4,5,5-trimethyl-6,7-dihydro-5H-pyrrolo[2,3-d]pyrimidine-2, 4-diamine, N2-((1R,5S,8s)-3-(6-Chloropyridazin-4-yl)-3-azabicyclo[3.2.1]octan-8-yl)-7-(4-fluorophenyl)-N4,5,5-trimethyl-6,7-dihydro-5H-pyrrolo[2,3-d]pyrimidine-2,4-diamine, 7-(3,4-Difluorophenyl)-N2-((1R,5S,8s)-3-(6-methoxypyridazin-4-yl)-3-azabicyclo[3.2.1]octan-8-yl)-N4,5,5-trimethyl-6,7-dihydro-5H-pyrrolo[2,3-d]pyrimidine-2, 4-diamine, 7-(4-Fluorophenyl)-N4,5,5-trimethyl-N2-((1R,5S,8s)-3-(pyridazin-4-yl)-3-azabicyclo[3.2.1]octan-8-yl)-6,7-dihydro-5H-pyrrolo[2,3-d]pyrimidine-2,4-diamine, N2-((1R,5S,8s)-3-(6-Methoxypyridazin-4-yl)-3-azabicyclo[3.2.1]octan-8-yl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine, 7-(2,4-Difluorophenyl)-N2-((1R,5S,8s)-3-(6-methoxypyridazin-4-yl)-3-azabicyclo[3.2.1]octan-8-yl)-N4,5,5-trimethyl-6,7-dihydro-5H-pyrrolo[2,3-d]pyrimidine-2, 4-diamine, 2-((7-(4-Fluorophenyl)-2-(((1R,5S,8s)-3-(6-methoxypyridazin-4-yl)-3-azabicyclo[3.2.1]octan-8-yl)amino)-5,5-dimethyl-6,7-dihydro-5H-pyrrolo[2,3-d]pyrimidin-4-yl)amino)ethanol, 8-(4-Fluorophenyl)-N2-((1R,5S,8s)-3-(6-methoxypyridazin-4-yl)-3-azabicyclo[3.2.1]octan-8-yl)-N4,5,5-trimethyl-5,6,7,8-tetrahydropyrido[2,3-d]pyrimidine-2,4-diamine, and 7-(2,3-Difluorophenyl)-N4,5,5-trimethyl-N2-((1R,5S, 8s)-3-(6-methoxypyridazin-4-yl)-3-azabicyclo[3.2.1] octan-8-yl)-6,7-dihydro-5H-pyrrolo[2,3-d]pyrimidine-2,4-diamine.

8. A compound of formula I-4,

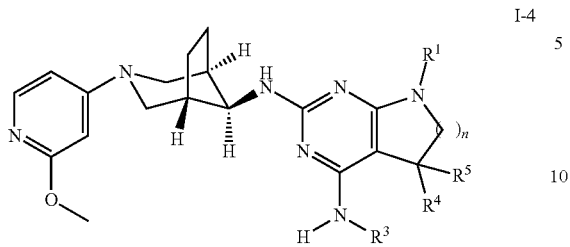

I-4 wherein:

R¹ is phenyl, lower alkyl, $C_{3-6}$-cycloalkyl, —CH$_2$—$C_{3-6}$-cycloalkyl or bridged $C_{4-7}$-cycloalkyl, substituted by one, two or three halogen atoms, lower alkyl, or lower alkyl substituted by halogen;

R³ is lower alkyl or lower alkyl substituted by hydroxy:

R⁴ is hydrogen or lower alkyl;

R⁵ is hydrogen or lower alkyl;

n is 1 or 2;

-( )$_n$- is —CH$_2$— or —CH$_2$CH$_2$— when n is 1 or 2;

or an enantiomer, or a pharmaceutically acceptable salt thereof.

9. A compound according to claim 8, or a pharmaceutically acceptable salt thereof, wherein the compound is selected from the group consisting of:

7-(4-Flurophenyl)-N2-((1R,5S,8s)-3-(2-methoxypyridin-4-yl)-3-azabicyclo[3.2.1]octan-8-yl)-N4,5,5-trimethyl-6,7-dihydro-5H-pyrrolo[2,3-d]pyrimidine-2,4-diamine, and 7-(2,3-Difluorophenyl)-N4,5,5-trimethyl-N2-((1R,5S,8s)-3-(2-methoxypyridin-4-yl)-3-azabicyclo[3.2.1]octan-8-yl)-6,7-dihydro-5H-pyrrolo[2,3-d]pyrimidine-2,4-diamine.

10. A process for preparing a compound of formula I of claim 1, which process comprises a) reacting a compound of formula II

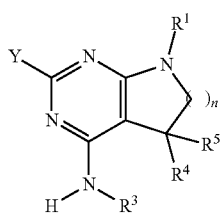

II with a compound of formula III

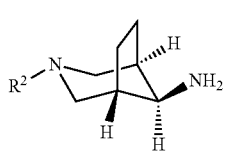

III to form a compound of formula I

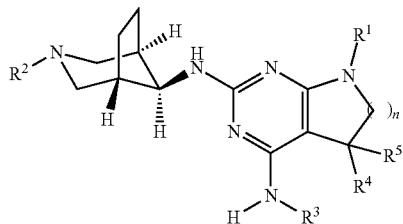

I wherein Y is halogen, and, optionally, converting the compounds obtained into pharmaceutically acceptable acid addition salts; or b) reacting a compound of formula VI

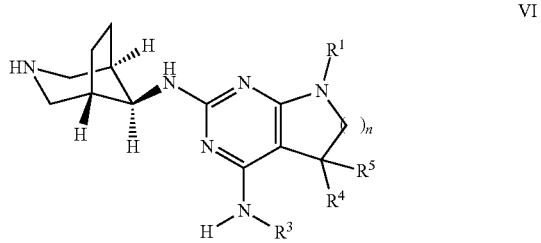

VI with a compound of formula R²—X to form a compound of formula I

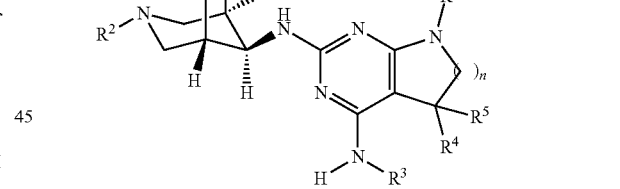

I wherein X is halogen, and optionally converting the compounds obtained into pharmaceutically acceptable acid addition salts, or c) reacting a compound of formula VIII

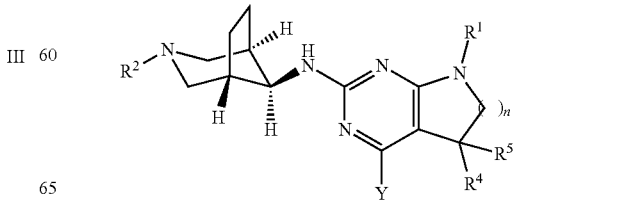

VIII with a compound of formula

H₂N—R³ to form a compound of formula

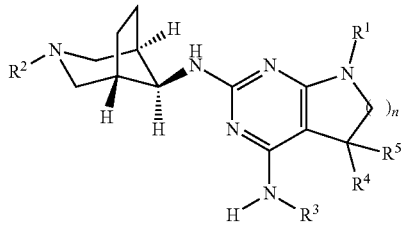

wherein Y is halogen, and optionally converting the compounds obtained into a pharmaceutically acceptable acid addition salt.

11. A compound prepared by a process according to claim 10.

12. A composition containing one or more compounds of claim 1, or pharmaceutically acceptable salts thereof, and one or more pharmaceutically acceptable excipients.

13. A method for treating a disease selected from: Alzheimer's disease; cerebral amyloid angiopathy; hereditary cerebral hemorrhage with amyloidosis, Dutch-type (HCHWA-D); multi-infarct dementia; dementia pugilistica; and Down syndrome, which method comprises administering an effective amount of a compound of claim 1, or a pharmaceutically acceptable salt thereof, to a patient in need thereof.

* * * * *